United States Patent [19]

Sing et al.

[11] Patent Number: 5,219,824

[45] Date of Patent: Jun. 15, 1993

[54] SUBSTITUTED 2,6-SUBSTITUTED PYRIDINE COMPOUNDS USEFUL AS HERBICIDES

[75] Inventors: Yuen-Lung L. Sing, St. Louis; Len F. Lee, St. Charles, both of Mo.

[73] Assignee: Monsanto Company, St. Louis, Mo.

[21] Appl. No.: 779,783

[22] Filed: Oct. 21, 1991

Related U.S. Application Data

[60] Division of Ser. No. 611,809, Nov. 13, 1990, Pat. No. 5,100,461, which is a division of Ser. No. 134,231, Dec. 24, 1987, Pat. No. 4,988,384, which is a continuation-in-part of Ser. No. 12,930, Feb. 9, 1987, abandoned.

[51] Int. Cl.$^5$ ....... C07D 413/04/417/04; A01N 43/32
[52] U.S. Cl. ..................... 504/221; 544/55; 544/96; 546/268; 546/277; 546/278; 546/280; 546/283; 504/225
[58] Field of Search ............ 544/96, 55; 71/92

[56] References Cited

U.S. PATENT DOCUMENTS

| 4,797,149 | 1/1989 | Lee et al. | 71/94 |
| 4,826,530 | 5/1989 | Lee | 71/94 |
| 4,826,532 | 5/1989 | Sing et al. | 71/94 |
| 4,835,279 | 5/1989 | Lee et al. | 546/315 |
| 4,885,026 | 12/1989 | Lee et al. | 71/94 |
| 4,988,384 | 1/1991 | Sing et al. | 71/94 |

*Primary Examiner*—Alan L. Rotman
*Attorney, Agent, or Firm*—Grace L. Bonner; Howard C. Stanley; James C. Bolding

[57] ABSTRACT

Disclosed herein are herbicidal pyridine compounds substituted at the 3- and/or 5-position with a carboxylic acid-derived heterocyclic moiety, as well as herbicidal compositions and use of these compounds.

34 Claims, No Drawings

SUBSTITUTED 2,6-SUBSTITUTED PYRIDINE COMPOUNDS USEFUL AS HERBICIDES

This is a division of application Ser. No. 611,809, filed Nov. 13, 1990, U.S. Pat. No. 5,100,461 which is a division of application Ser. No. 134,231 filed Dec. 24, 1987, now U.S. Pat. No. 4,988,384, which is a continuation-in-part of application Ser. No. 012,930, filed Feb. 9, 1987, now abandoned.

This invention relates to a new class of 2,6-substituted pyridinecarboxylic acid derivatives having a wide range of activity as herbicides.

Pyridine derivatives have, for many years, been investigated for use in the biological sciences. For example, 2,6-bis-(trifluoromethyl)-4-pyridinols have been found useful as herbicides and fungicides as disclosed in U.S. Pat. No. 3,748,334. Such compounds are characterized by substitution in the 4-position by a hydroxy radical. In addition to the hydroxy radical, the pyridine nucleus may also be substituted with bromo, chloro or iodo radicals. Trifluoromethyl pyridine derivatives have also been disclosed in U.S. Pat. Nos. 2,516,402 and 3,705,170 wherein the nucleus is further substituted by halogens as well as numerous other substituents. Some of these compounds are also noted to be useful as herbicides.

Also known because of their fungicidal activity are 4-substituted 2,6-dichloro-3,5-dicyanopyridines wherein the 4-position is substituted with alkyl, phenyl, naphthyl or pyridyl groups. Such compounds are disclosed in U.S. Pat. No. 3,284,293, while similar compounds are disclosed in U.S. Pat. No. 3,629,270 wherein the 4-position is substituted with a heterocyclic group wherein the hetero atom is oxygen or sulfur.

In EPO patent 44,262 there are disclosed 2,6-dialkyl-3-phenylcarbamyl-5-pyridinecarboxylates and 5-cyano-compounds useful as herbicides. There is no disclosure of the 2-haloalkyl radicals nor any substitution in the 4-position of the pyridine ring.

The pyridine derivatives have also received attention in the search for new herbicides and have been reported in U.S. Pat. Nos. 1,944,412, 3,637,716, and 3,651,070. All of these patents disclose polyhalo derivatives of dicarboxypyridines. All have in common the direct substitution on a ring carbon by a halogen in the 3- and 5-positions while the 2- and 6-positions are occupied by carboxylate groups. The 4-position is open to substitution by a wide range of materials including halogens, hydroxy radicals, alkoxy, and carboxyl groups. Such compounds have found utilization as herbicides, bactericides, and fungicides. When the 4 position is occupied by a silver salt, U.S. Pat. No. 1,944,412 discloses that such compounds have been utilized in the production of X-ray pictures with intravenous injection of such compounds.

Pyridinedicarboxylate compounds useful as herbicides are described in European Patent publication 133,612 published Feb. 27, 1985 which corresponds to U.S. application Ser. No. 602,021. These compounds have fluorinated methyl groups at the 2- and 6-positions and carboxylic acid derivative at the 3- and 5-positions.

Other pyridinedicarboxylate compounds including pyrazole amides are disclosed in European Patent publication 0182769, published May 28, 1986. This European publication corresponds to U.S. application Ser. No. 768,659.

BRIEF DESCRIPTION OF THE INVENTION

It is an object of this invention to provide herbicidal methods and compositions utilizing the novel pyridines of this invention.

The novel compounds of this invention are useful as herbicides or intermediates which can be converted to herbicides and are represented by the generic formula

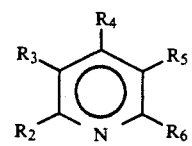

wherein:

$R_3$ is selected from the group consisting of 4,5-dihydro-2-oxazolyl; 2-oxazolyl; 2-thiazolyl; 4,5-dihydro-2-thiazolyl; 5,6-dihydro-4H-1,3-oxazin-2-yl; 5,6-dihydro-4H-1,3-thiazin-2-yl; 4,5-dihydro-1H-imidazol-2-yl; 2-oxazolidinyl; 1,3,4-oxadiazol-2-yl; 4,5-dihydro-1,3,4-oxadiazol-2-yl; 1,3-dithiolan-2-yl; 1,3-dithian-2-yl,2-thiazolidinyl; 1,3-dioxolan-2-yl; 1,3-dioxan-2-yl; 1,3-oxathiolan-2-yl; 5-tetrazolyl, 5-oxazolyl, and the above mentioned heterocycles substituted with one or more substituents selected from hydrogen, lower alkyl, alkoxy and trifluoroacetyl, and 1-amino-4,5-dihydro-1H-imidazolyl;

$R_4$ is selected from $C_1$-$C_4$ straight or branched chain alkyl, $C_3$-$C_4$ cycloalkyl, cycloalkylalkyl, alkylthioalkyl, and bis(alkylthio)alkyl;

$R_5$ is the same as $R_3$ or is

or —C≡N where $Z_1$ is O, S, or $NR_7$ where $R_7$ is lower alkyl, and $Z_2$ is selected from alkoxy, alkenoxy, alkynoxy, alkylthio, pyrazolyl, haloalkoxy, cyanoalkoxy, chloro, and —$NHR_8$ where $R_8$ is lower alkyl; and $R_2$ and $R_6$ are independently selected from fluorinated methyl, chlorofluorinated methyl, chlorinated methyl and lower alkyl, provided that one of $R_2$ and $R_6$ must be fluorinated or chlorofluorinated methyl;

provided that $R_3$ is not 4,5-dihydro-1-methyl-1H-imidazol-2-yl when $R_5$ is methylthiocarbonyl, and $R_3$ is nor an unsubstituted 4,5-dihydro-1H-imidazol-2-yl when $R_5$ is methoxycarbonyl.

The term "alkyl" means herein both straight and branched chain radicals which include, but are not limited to, ethyl, methyl, n-propyl, 1-ethylpropyl, 1-methylpropyl, n-butyl, 2,2-dimethylpropyl, pentyl, isobutyl, isopropyl.

The term "lower alkyl" herein means an alkyl radical having 1 to 7 carbon atoms. The terms "lower alkenyl" and "lower alkynyl" herein mean alkenyl and alkynyl groups having 3 to 7 carbon atoms. Examples of such alkenyl groups include 2-propenyl, 2-butenyl, 3-butenyl, 2-methyl-2-propenyl, and the like. Examples of such lower alkynyl groups include 2-propynyl, and so forth.

The term "cycloalkylalkyl" means a $C_1$-$C_2$ alkyl group substituted with a $C_3$-$C_6$ cycloalkyl group, such as cyclopropylmethyl, cyclopropylethyl, cyclobutylmethyl, cyclopentylethyl, and so forth.

The terms "fluorinated methyl", "chlorinated methyl", and "chlorofluorinated methyl" mean methyl radicals wherein one or more of the three hydrogen atoms have been replaced by a fluorine atom, a chlorine atom, or a fluorine atom and a chlorine atom, respectively.

DETAILED DESCRIPTION OF THE INVENTION

The novel herbicidal derivative and their compounds of this invention are readily prepared by reaction of a pyridinedicarboxylic acid mono ester, monoacid halide or a diacid halide with a γ-hydroxyamine having 2-3 carbon atoms or a hydrazine having one carbon atom to form the pyridinedicarboxylic acid amide, bis-amide, or hydrazide respectively. Steps 1-9 which follow set out in detail the preparation of three specific acid halides which are used as starting materials for the compounds of this invention. Other acid halides may be readily prepared using the procedures of Steps 1-9 by varying the ketoester and aldehyde used in Step 1 to obtain the desired substituents in the pyridinedicarboxylate product. Other suitable pyridinedicarboxylic acid halides as starting materials are shown in European Patent publication No. 133,612 and U.S. Pat. No. 4,692,184 in Examples 44-51 and 82-83 inclusive, and halide starting materials used herein are generally prepared using the techniques set out in that European Patent publication.

The following Steps 1-9 illustrate an example of the procedures for preparation of the acid halide compounds which are the starting materials for making the compounds of the present invention. In these steps, β-ketoester is reacted with an aldehyde preferably using piperidine as a catalyst to form a pyran (Step 1). The pyran is then reacted with ammonia to form a dihydroxypiperidine (Step 2), which is dehydrated to make a dihydropyridine compound (Step 3). The dihydropyridine is then oxidized or dehydrofluorinated to prepare a pyridinedicarboxylate compound (Step 4). In the dehydrofluorination step, an organic base such as DBU (hereinafter defined) is employed.

The ester groups of the pyridinedicarboxylate compound are the ester groups of the β-ketoester, and the 4-position of the pyridine is substituted with the aldehyde substituent.

When the pyridinedicarboxylate is substituted at the 2- or 6-position with a trifluoromethyl radical and at the other of these positions with a difluoromethyl hydrolysis of the pyridinedicarboxylate compound occurs selectively on the side having the $CF_2H$ group when one equivalent of a base such as KOH is employed in the hydrolysis (Step 8). When two equivalents of base or more are employed, the dicarboxylate is hydrolyzed to the diacid (Step 5). The diacid may be converted to the diacid chloride by treatment with a chlorinating agent such as $SOCl_2$ or $PCl_5$. Following this conversion, treatment with one equivalent of an alcohol selectively esterifies the diacid chloride on the chloride group adjacent the $CF_2H$ group.

The novel compounds of this invention wherein one of the $R_3$ or $R_5$ is a 2-oxazolidinyl, 2-thiazolidinyl, 1,3-dithiolan-2-yl, and 1,3-dithian-2-yl can be prepared from the corresponding 3- or 5-formyl derivatives. Step 10 and Step 11 set out in detail the preparation of the formyl derivatives.

STEP 1

Preparation of dimethyl 2,6-bis(trifluoromethyl)-2,6-dihydroxy-4-isobutyl-tetrahydro-3,5-pyrandicarboxylate To a mechanically stirred mixture of 280 g (2.0 mole) of 80% pure methyl trifluoroacetoacetate and 86 g (1.0 mole) of isovaleraldehyde is added 1 ml of piperidine. An exothermic reaction occurs and the temperature of the reaction mixture reaches 105° C. After 5 hours of stirring, the reaction mixture is triturated with 450 ml of hexane and 30 ml of ether and cooled with a dry ice bath to give 1.68 g of a first crop, m.p. 83°–87° C. and 14.51 g of a second crop, m.p. 67°–73° C.

The first crop is the desired product which contains a mixture of 5:1 cis and trans isomers. Anal. Calc'd for $C_{15}H_{20}F_6O_7$: C, 42.26; H, 4.73. Found: C, 42.54; H, 4.77

The second crop is a 2:1 mixture of cis and trans isomers. The mother liquor is concentrated to give 344 g of a residue which is a crude mixture of cis and trans isomer of the desired product.

STEP 2

Preparation of dimethyl 2,6-bis(trifluoromethyl)-2,6-dihydroxy-4-isobutyl-3,5-piperidinedicarboxylate To a solution of 344 g (0.920 mole) crude product from Step 1 in 500 ml of tetrahydrofuran (THF) is passed 58 g (3.41 mole) of gaseous ammonia for 3 hours. The reaction mixture is concentrated and the residue (332 g) is recrystallized from hexane-ether to give 53.7 g (13% yield from methyl trifluoroacetoacetate) of the desired product as a white solid, m.p. 102°–106° C.

Anal. Calc'd for $C_{15}H_{21}F_6N_1O_6$: C, 42.36; H, 5.00; N, 3.29. Found: C, 42,84; H, 4.94; N, 3.29

The mother liquor is concentrated to provide more of the crude desired product.

STEP 3

Preparation of a 2:1 mixture of dimethyl 2,6-bis(trifluoromethyl)-1,4-dihydro-4-isobutyl-3,5-pyridinedicarboxylate and its 3,4-dihydropyridine isomer Method A: To an ice water cooled mixture of 200 ml of concentrated sulfuric acid and 200 ml of methylene chloride is added 48.7 g (0.115 mole) of the product of Step 2 at once. The reaction mixture is stirred for 20 minutes and poured into 1 L. of ice water The methylene chloride layer is separated and washed once with 100 ml of saturated sodium bicarbonate, dried and concentrated to give 28.0 g (64.6%) of crude product. A portion (5.0 g) of this product is kugelrohr distilled at 0.5 torr (pot temperature at 120° C.) to give 4.8 g of the desired product, $n_D^{25}$ 1.4391.

Anal. Calc'd for $C_{15}H_{17}F_6N_1O_4$: C, 46.28; H, 4.40; N, 3.60; Found: C, 46.39; H, 4.44; N, 3.60

Method B: To a mechanically stirred mixture of 340.3 g (1.98 mol) of 98.9% pure methyl trifluoroacetoacetate (MTFAA), 100 mL of toluene and 0.86 g (0.01 mol) of piperidine was added 90.5 g (1.03 mol) of iso-valeraldehyde in 20 minutes. The reaction mixture exothermed causing a rise of temperature of 83° C. The reaction mixture was maintained at 80° C. for 3 hours. $^{19}F$ NMR showed that the reaction was 89% complete. Heat was removed, and the reaction mixture was diluted with 125 mL of toluene and stirred overnight (16 hours). Gaseous ammonia was passed through the reaction, the exotherm caused a rise of temperature to 68° C. in 50 minutes. A water cooling bath was applied to the reaction vessel to reduce the reaction temperature to 53° C. while ammonia was passed continuously. A total of 47.3 g (2.78 mol) of ammonia was passed in 1.5 hours. $^{19}F$ NMR indicated that dimethyl 2,6-bis(trifluoromethyl)-2,6-dihydroxy-4-isobutyl-3,5-piperidinedicarboxylate constituted 91% of the product mixture. The reaction mixture was diluted with 100 mL of toluene. A Claisen distillation head was attached to the reaction vessel.

Excess ammonia and parts of toluene were removed in vacuo (water aspirator) while temperature was maintained at 26° C. An additional 200 mL of toluene was added, and the distillation was continued to remove a total of 200 mL of distillate in 1.5 hours. The reaction mixture was diluted with 100 mL of toluene and cooled to 5° C. with an ice bath. Sulfuric acid (453 g, 4.53 mol) was added in 5 minutes. The exotherm caused the temperature to rise to 25° C. The temperature gradually subsided to 5° C. in 10 minutes and was maintained at 5° C. for 40 minutes. An additional 95 g (0.95 mol) of sulfuric acid was added, and the reaction mixture was stirred at 5° C. for 20 minutes before being poured into a mixture of 500 mL of toluene and 2 L of ice water. The toluene layer was separated and the aqueous layer was extracted once with 500 mL of toluene. The combined toluene extracts were washed successively with 500 mL of water, 500 mL of saturated aqueous NaHCO$_3$, 500 mL of brine and concentrated in vacuo to 363.6 g of an oil. GC area percentage analysis indicated that the oil contained 9% of dimethyl 2,6-bis(trifluoromethyl)-3,4-dihydro-4-isobutyl-3,5-pyridinedicarboxylate and 75.4% of dimethyl 2,6-bis(trifluoromethyl)-1,4-dihydro-4-isobutyl-3,5-pyridinedicarboxylate corresponding to an overall yield of 82.5% from MTFAA.

STEP 4

Preparation of dimethyl 2-(difluoromethyl)-6-(trifluoromethyl)-4-isobutyl-3,5-pyridinedicarboxylate (a) Reaction of the Product of Step 3 with DBU A mixture of 23.0 g (0.0591 mole) of the product of Step 3, 12.2 g (0.077 mole) of 96% pure DBU, and 100 ml of THF is held at reflux for 3 days and poured into 250 ml of 3N HCl. The oil precipitate is extracted into ether (2×100 ml). The ether extracts are dried (MgSO$_4$) and concentrated to give 14.4 g of an oil which, according to $^1H$ NMR, contained the desired product and acidic products. This oil is dissolved in ether and extracted with 100 ml of saturated sodium bicarbonate. The ether layer is dried (MgSO$_4$) and concentrated to give 8.9 g of an oil which is the desired product (71% pure by $^{19}F$ NMR).

The sodium bicarbonate extract is acidified with concentrated aqueous HCl to give an oil which is extracted into ether. The ether layer is dried (MgSO$_4$) and concentrated to give 4.8 g of a residue which contained monocarboxylic acid and dicarboxylic acid (9:1) derived from the desired product. This residue is treated with 3.0 g (0.0217 mole) of potassium carbonate, 20 ml of methyl iodide, and 50 ml of acetone. The mixture is held at reflux for 42 hours and concentrated. The residue is treated with water and extracted with ether (2×100 ml). The ether layer is dried and concentrated. The residue is kugelrohr distilled at 1 torr (pot temperature at 130° C.) to give 5.1 g (23.4% from Step 3) of the desired product as an oil, $n_D^{25}$ 1.4478. This product crystallizes after standing, m.p. 36°-37° C.

Anal. Calc'd for $C_{15}H_{16}F_5N_1O_4$: C, 48.79; H, 4.37; N, 3.79; Found: C, 48.75; H, 4.39; N, 3.77

The 71% pure desired product described previously was chromatographed by HPLC using 3% ethyl acetate/cyclohexane as eluent to give an earlier fraction (0.79 g, retention time 7-8.5 minutes) which was identified as methyl 6-(difluoromethyl)-4-(isobutyl)-2-(trifluoromethyl)-3-pyridinecarboxylate. The second fraction (retention time 8.5-18.5 minutes) is an additional 6.4 g (29.4%) of pure desired product, $n_D^{25}$ 1.4474.

(b) Reaction of the Product of Step 3 with Tributylamine

A mixture of 38.9 g of an 80% pure product of Step 3 and 20.5 g of tributylamine is heated to 155° C. in 30 minutes. The reaction mixture was cooled to 30° C. and diluted with 100 ml of toluene. The toluene solution is washed successively with 6N hydrochloric acid, saturated sodium bicarbonate, and brine, dried and concentrated to give 36.4 g of a 73% pure product which corresponds to an 86% yield. This reaction can also be carried out in excess of tributylamine (10 equivalent) giveing essentially similar results.

(c) Reaction of the Product of Step 3 with Tributylamine in Toluene

A mixture of 38.9 g of an 80% pure product of Step 1, 20.4 g of tributylamine and 30 ml of toluene is heated to 115° C. in 40 minutes and held at 115° C. for 1 hour and 40 minutes. The reaction mixture is cooled and worked up as in (b) above to give 36.3 g of a 76% pure product which corresponds to a 90% yield.

(d) Reaction of the Product of Step 3 with Triethylamine

A mixture of 11.8 g of an 80% pure product of Step 3 and 3.34 g of triethylamine is heated at 100° C. for 10 minutes, then at 125° C. for 10 minutes. The reaction mixture was cooled and worked up as in (b) above to give 8.14 g of a 76% pure product which corresponds to a 63% yield.

(e) Reaction of the Product of Step 3 with 2,6-Lutidine in the Presence of a Catalytic Amount of DBU A mixture of 5.0 g of product of Step 3 and 2.13 g of 2,6-lutidine is heated at 143° C. for 30 minutes. Two drops of DBU are added and the reaction mixture is heated for additional 1 hour and 30 minutes, cooled and worked up as in (b) above to give 4.23 g of the desired product. The reaction can also be carried out in excess of 2,6-lutidine and a catalytic amount of DBU without solvent or in the presence of toluene as solvent giving similar results.

STEP 5

Preparation of 2-(difluoromethyl)-6-(trifluoromethyl)-4-isobutyl-3,5-pyridinedicarboxylic acid A 5-liter flask was charged with 894 g (2.42 mol) of the compound of Step 4 and 1 liter of water. To this was added a solution of 574 g (8.7 mol) of KOH in 800 ml of water. The mixture was refluxed overnight, after which HPLC showed that the reaction was complete. The flask was cooled to room temperature, acidified with aqueous HCl, and stirred until the organic phase solidified. The solids were filtered, washed with water, and dried in a fluid bed dryer. The diacid was obtained (756 g, 91.6% yield) as a brown solid.

STEP 6

Preparation of 3,5-bis-chlorocarbonyl-2-difluoromethyl-4-isobutyl-6-trifluoromethyl-pyridine The diacid product of Step 5 (37.06 g, 0.108 mole) was refluxed with 150 ml $SOCl_2$ for three hours. At this time, $^{19}F$ NMR indicated the reaction was complete. The excess $SOCl_2$ was removed by rotary evaporation, leaving a dark oil which was the bis-acid chloride. This was Kugelrohr distilled at 100° C. to give a colorless oil.

STEP 7

Preparation of methyl 5-chlorocarbonyl-2-difluoromethyl-4-isobutyl-6-trifluoromethyl-pyridine-3-carboxylate The product of Step 6 was then dissolved in 100 ml THF followed by 100 ml methanol. After 2½ hours the solvent was evaporated, leaving 31.2 g white solid, m.p. 71°–75° C. in 77% yield.

STEP 8

Preparation of 2-difluoromethyl-4-isobutyl-6-trifluoromethyl-3,5-pyridinedicarboxylic acid, 5-methyl ester A 1-liter 4-necked flask was charged with 300 gm of product of Step 4 and about 200 ml ethanol. In a separate flask was combined 59.14 g (0.896 mol) of 85% KOH and about 100 ml of water. The aqueous solution was poured into the organics and the flask was equipped with a mechanical stirrer, thermometer, nitrogen inlet and a water cooled condenser. The reaction mixture was heated to reflux for 45 minutes and was cooled. The reaction mixture was concentrated and then diluted with water and washed once with ethyl ether. The ether wash (to remove starting material) was discarded. The aqueous solution was acidified with concentrated aqueous HCl and the orange precipitate that resulted was extracted with ethyl ether. (The aqueous solution was extracted a total of 3 times because of the volume.) The ether extracts were combined and dried over anhydrous magnesium sulfate, filtered and concentrated to yield 253.13 gm (87.53% yield) of the monoacid acid.

STEP 9

Preparation of methyl 2-difluoromethyl-3-chlorocarbonyl-4-isobutyl-6-trifluoromethyl-5-pyridinecarboxylate The acid (253 g 0.7121 mol) from Step 8 was refluxed for 24 hours in approximately 250–300 ml of thionyl chloride. The reaction mixture was concentrated to yield 244.59 gms. of acid chloride in 91.90% yield. $n_D^{25}$ 1.4614.

STEP 10

3-pyridinecarboxylic acid, 2-(difluoromethyl)-5-(hydroxymethyl)-4-(2-methylpropyl)-6-(trifluoromethyl), methyl ester To a mixture of 14.2 g (0.64 mol) of sodium borohydride and 700 mL of diglyme cooled in an ice-water bath was added a solution of 118.5 g (0.32 mol) of methyl 5-(chlorocarbonyl)-2-(difluoromethyl)-4-(2-methylpropyl)-6-(trifluoromethyl)-3-pyridinecarboxylate in 200 mL of diglyme at a fast dropwise pace. The reaction was exothermic during addition of the acid chloride solution. After the addition was complete, the reaction mixture was stirred in the ice-water bath for 1 hour then at room temperature for 2 hours. At this point GC showed that the reaction was complete. To the above reaction mixture was added very slowly 150 mL of concentrated hydrochloric acid causing vigorous evolution of gas. After gas evolution had subsided the reaction mixture was concentrated in vacuo (0.1 torr) at 75° C. The residual oil was taken up in 300 mL of $CH_2Cl_2$ and washed with 300 mL of water. The $CH_2Cl_2$ layer was dried ($MgSO_4$) and concentrated in vacuo. The residue was Kugelrohr distilled at 110° C. (0.04 torr) to remove diglyme. The residue was chromatographed by HPLC using hexane: $CH_2Cl_2$:EtOAc (10:1:1, v/v) as eluent to give 93.6 g (85.8%) of light yellow solid, mp 65°–67° C.

STEP 11

3-pyridinecarboxylic acid, 2-(difluoromethyl)-5-formyl-4-(2-methylpropyl)-6-(trifluoromethyl), methyl ester To a suspension of 14.2 g (0.0655 mole) of pyridinium chlorochromate in 60 ml of $CH_2Cl_2$ was added 14.9 g of product of Step 10 in 40 ml of $CH_2Cl_2$. The mixture was stirred at room temperature overnight and diluted with 400 ml of ether and filtered through a short pad of silica gel twice to give a light brown solution, which was concentrated to give 13.9 g of a residue and then purified by HPLC (3% ethyl acetate/cyclohexane) to give 12.75 g of a light yellow oil, $n_D^{25}$ 1.4564.

In compounds of this invention wherein $R_5$ is a dihydro-oxazole or dihydro-oxazole derivative, the acid halide prepared as in one of Steps 6, 7 or 9 is reacted with a 2-hydroxyethyl amine to form the corresponding 2-hydroxyethyl amide. The amide is treated in a suitable solvent (such as $CH_2Cl_2$ or the like) with a chlorinating agent ($SOCl_2$, $PCl_5$, etc ) to form the corresponding γ-chloroethyl amide, which is then cyclized with a suitable base such as potassium t-butoxide (t-BuOK hereinafter) to form the dihydro-oxazole or dihydro-oxazole derivative.

Dihydrothiazole compounds of this invention and their derivatives are formed by treatment of the 2-hydroxyethylamide above with $P_2S_5$ to form a carbothioamide which cyclizes to the dihydrothiazole. Treatment of the 2-hydroxyethyl amide above with $P_2S_5$ and hexamethyl phosphoramide results in sulfurization and cyclization to form the 4,5-dihydrothiazole.

Oxadiazole compounds of this invention are formed by reaction of a hydrazine with the acid chloride to make a hydrazide, followed by cyclization.

Imidazole compounds are prepared by reaction of a 2-chloroethyl amide with phosphorus pentachloride followed by reaction of the intermediate with ammonia or an alkylamine.

Six-membered ring counterparts of the above pyridines with 5-membered ring substitution are prepared by cyclization of 3-chloropropyl amides.

Preparation of compounds of this invention will become clear by reference to the following examples.

As used throughout the specification, including the Examples, the following abbreviations have the following meanings:

THF—tetrahydrofuran
HPLC—high pressure liquid chromatography
TLC—thin layer chromatography
RT—room temperature
DBU—1,8-diazabicyclo-[5.4.0]-undec-5-ene HMPA—hexamethyl phosphoramide
EtOAc—ethyl acetate
DME—dimethoxyethane
t-BuOK—potassium t-butoxide

EXAMPLE 1

3-pyridinecarboxylic acid, 6-(difluoromethyl)-5-(4,5-dihydro-4-methyl-1,3,4-oxadiazol-2-yl)-4-(2-methylpropyl)-2-(trifluoromethyl)-, methyl ester 3-pyridinecarboxylic acid, 5-chlorocarbonyl-6-(difluoromethyl)-4-(2-methylpropyl)-2-(trifluoromethyl)-, methyl ester (2.28 g=0.0061 mole) and 30 ml $CH_2Cl_2$ were cooled in an ice bath before adding 0.8 ml $NH_2NHCH_3$. The reaction mixture became cloudy white. After 40 minutes the ice bath was removed. One hour later a gas chromatographic assay showed complete reaction. The mixture was washed with $H_2O$ and extracted with $CH_2Cl_2$. The $CH_2Cl_2$ layer was dried with $MgSO_4$, filtered and concentrated to 2.2 g white solid. This was recrystallized from about 30% ethyl acetate/hexanes to give 1.5 g 3,5-pyridinedicarboxylic acid, 2-(difluoromethyl)-4-(2-methylpropyl)-6-(trifluoromethyl)-, 3-(2-methylhydrazide) 5-methyl ester as a fluffy white solid. m.p. 155°–159° C. Also, 0.9 g of this intermediate was recovered from the filtrate.

The hydrazide (2.4 g), 27 ml 95% HCOOH and 25 ml 37% formaldehyde were combined at room temperature. The reaction was homogeneous. After 1 hour $^{19}F$ Nmr showed one major $CF_3$ peak. The reaction sat overnight at room temperature with no major change in the $^{19}F$ NMR specturm. The mixture was poured into ice/$H_2O$ and extracted with $CH_2Cl_2$. The $CH_2Cl_2$ layer was washed with $NaHCO_3$ (aqueous) and then dried with $MgSO_4$, filtered and concentrated to 2.5 g colorless oil. This was chromatographed in 30% $CH_2Cl_2$/cyclohexane, gradually increasing to 100% $CH_2Cl_2$. The product (1.56 g) was recovered as a colorless oil, $n_D^{25}=1.4822$ (63% yield).

EXAMPLE 2

3-pyridinecarboxylic acid, 6-(difluoromethyl)-5-(4,5-dihydro-4,4-dimethyl-2-oxazolyl)-4-(2-methylpropyl)-6-(trifluoromethyl)-, methyl ester A solution of 4.2 ml of dimethylethanolamine (0.044 mole) and 25 ml $CH_2Cl_2$ was cooled by an ice bath under a $N_2$ atmosphere. Then a solution of 16.53 g acid chloride used in Example 1 (0.044 mole) in 100 ml $CH_2Cl_2$ was added over a 50 minute period. The bath was removed and stirring was continued at room temperature. Another 4 ml of dimethylethanolamine was added, and the reaction stirred over the weekend. There was solid in the reaction mixture. It was washed with diluted aqeous HCl and extracted with $CH_2Cl_2$. The $CH_2Cl_2$ layer was dried with $MgSO_4$, filtered and concentrated to 18.36 g orange solid. This was purified by chromatograph using 40% EtOAc/cyclohexane. About 5 g good product was recovered, along with some impure product. The best material was recrystallized from 35% EtOAc/hexane to give 2.9 g white solid. m.p. 170°–173°. The impure product was further purified by boiling in 10% EtOAc/hexane and filtering off the insoluble amide. A total of 7.0 g of 3-pyridinecarboxylic acid, 6-(difluoromethyl)-5-[[(2-hydroxy-1,1-dimethylethyl)amino]carbonyl]-4-(2-methylpropyl)-2-(trifluoromethyl)-, methyl ester was prepared in this manner (37% yield).

This hydroxyethyl amide compound (3.65 g=0.0086 mole) was heated with 30 ml $SOCl_2$ for approximately 1¾ hours. $^{19}F$ NMR showed the reaction was complete. The $SOCl_2$ was evaporated, leaving a white solid. This was dissolved in $CH_2Cl_2$ and washed with $H_2O$. The $CH_2Cl_2$ layer was dried with $MgSO_4$, filtered and concentrated to yield 3-pyridinecarboxylic acid, 5-[[(2-chloro-1,1-dimethylethyl)amino]carbonyl]-6-(difluoromethyl)-4-(2-methylpropyl)-2-(trifluoromethyl)-, methyl ester as a solid (3.4 g). This 89% yield was recrystallized from 5% EtOAc/hexane. m.p. 136°–138° C.

This intermediate (2.46 g=0.0055 mole) and 90 ml dry THF were combined under $N_2$ and cooled in an ice bath. Then 0.70 g t-BuOK was added (0.0062 mole). The reaction mixture turned dark in color. After 1 hour the THF was evaporated, and the residue was washed with $H_2O$ and extracted with ether. The ether layer was dried with $MgSO_4$, filtered and concentrated to 2.36 g orange oil. This was purified by chromatograph using 5% EtOAc/cyclohexane and then Kugelrohr distilled at 110° C. to give 1.29 g colorless oil. (57% yield) It gradually solidified. m.p. 69°–71° C.

EXAMPLE 3

3-pyridinecarbothioic acid, 6-(difluoromethyl)-5-(4,5-dihydro-2-oxazolyl)-4-(2-methylpropyl)-2-(trifluoromethyl)-, S-methyl ester A solution of 2.5 ml ethanolamine (0.0394 mole) in 50 ml $CH_2Cl_2$ was cooled by an ice bath before adding 7.28 g of 3-pyridinecarbothioic acid, 5-(chlorocarbonyl)-6-(difluoromethyl)-4-(2-methylpropyl)-2-(trifluoromethyl)-, S-methyl ester (0.0187 mole) in 70 ml $CH_2Cl_2$ dropwise. The bath was removed and the mixture was stirred magnetically for 2 hours. The reaction sat overnight before workup. It was washed with NaCl(aqueous) and extracted with more $CH_2Cl_2$. The $CH_2Cl_2$ layer was collected, dried with $MgSO_4$, filtered and concentrated to an orange oil. This was dissolved in ethyl acetate and filtered through silica gel. After concentrating, 6.44 g was recovered. 83% yield. A 1.4 g sample was chromatographed in 40% EtOAc/cyclohexane. A pale colored oil (1.16 g) was recovered which gradually solidified. This was recrystallized from 10% EtOAc/hexanes. There was recovered 0.92 g of 3-pyridinecarbothioic acid, 6-(difluoromethyl)-5-[[(2-hydroxyethyl)amino]carbonyl]-4-(2-methylpropyl)-2-(trifluoromethyl)-, S-methyl ester as white crystals: m.p. 102°–106° C.

This material (5.31 g=0.0128 mol) was combined with 50 ml $SOCl_2$ at room temperature. The reaction was followed by $^{19}F$ NMR. After 2½ hours $^{19}F$ NMR showed two $CF_3$ peaks. The solution was refluxed for 40 minutes with no change in the spectrum. The reaction sat overnight at room temperature. The $SOCl_2$ was rotavapored off, leaving a yellow solid. This was dissolved in ether and washed with $H_2O$. The ether layer was collected, dried with $MgSO_4$, filtered and concentrated to a 5.0 g yellow solid. This was recrystallized from 10% EtOAc/cyclohexane which yielded 3.4 g (60% yield) white solid. $^{19}F$ NMR spectrum showed one singlet for the $CF_3$. The filtrate showed two components of which one was 3-pyridinecarbothioic acid, 5-[[(2-chloroethyl)amino]carbonyl]-6-(difluoromethyl)-4-(2-methylpropyl)-2-(trifluoromethyl)-, S-methyl ester. The identity of the other component is unknown.

This intermediate (2.40 g=0.0055 mole) was dissolved in dry THF under a $N_2$ atmosphere. The solution was cooled in an ice bath before adding 0.76 g t-BuOK (0.0068 mole). The solution immediately darkened in color. After 10 minutes the ice bath was removed and the solution warmed to room temperature. A gas chromatographic assay showed complete reaction, so it was poured into water and extracted with ether. The ether layer was collected, dried with $MgSO_4$, filtered and concentrated to 2.02 g yellow oil which began to solidify. It was chromatographed in 20% EtOAc/cyclohexane and then recrystallized from hexane to give 1.70 g product (77% yield). m.p. 88°–90° C.

EXAMPLE 4

3-pyridinecarboxylic acid, 6-(difluoromethyl)-5-(5-methoxy-2-oxazolyl)-4-(2-methylpropyl)-2-(trifluoromethyl)-, methyl ester The acid chloride starting material of Example 1 (12.81 g=0.0345 mole) was dissolved in 100 ml $CH_2Cl_2$. To this solution was added 4.68 g (0.0373 mol) of glycine methyl ester hydrochloride. This mixture was cooled in an ice bath before adding 10 ml of ethyldiisopropylamine (EDPA)(0.0574 mole) by pipet. The ice bath was removed, and the reaction stirred overnight at room temperature. $^{19}F$ NMR showed the reaction was incomplete. An additional 3 ml of EDPA (0.0172 mol) was added. After ½ hour a gas chromatographic assay showed complete reaction. It was washed with dilute HCl and extracted with $CH_2Cl_2$. The $CH_2Cl_2$ layer was dried with $MgSO_4$, filtered and concentrated to 14.2 g orange oily solid. Two grams were chromatotroned (20% EtOAc/cyclohexane) and then recyrstallized to give 1.2 g of 3-pyridinecarboxylic acid, 6-(difluoromethyl)-5-[[(2-methoxy-2-oxoethyl)amino]carbonyl]-4-(2-methylpropyl)-2-(trifluoromethyl)-, methyl ester as a white solid. m.p. 126°–129° C.

This material (8.90 g=0.0209 mole), 85 ml of $CCl_4$ and 4.5 g of $PCl_5$ (0.0216 mole) were combined and heated at reflux for one hour. NMR showed complete reaction to the intermediate. The cyclization reaction was accomplished by three different procedures.

1. About 10 ml of the intermediate solution was evaporated to remove $CCl_4$ and $POCl_3$ and then heated at 50° C. on the Kugelrohr apparatus to remove trace components. The residue was dissolved in $CH_2Cl_2$ and then washed with $NaHCO_3$(aqueous). The $CH_2Cl_2$ layer was dried with $MgSO_4$, filtered and concentrated to a yellow oil. This procedure effected no change in the NMR. The oil was dissolved in 25 ml xylene and refluxed for 2 hours. The reaction was followed by NMR. When it indicated the reaction was complete, the xylene was evaporated to give the oxazole as a yellow oil.

2. About 10 ml of the intermediate solution was evaporated and then heated on the Kugelrohr apparatus at 100° C. After 15 minutes a gas chromatographic assay of the pot contents showed partial reaction to the oxazole. The reaction was heated at 100° C. for another hour but a gas chromatographic assay still showed some intermediate. Then heating was resumed up to 135° C. and the oxazole distilled over.

3. The remaining intermediate solution was evaporated and heated on the Kugelrohr apparatus at 50° C. for a short time to remove traces of $CCl_4/POCl_3$. The residue was dissolved in xylene and refluxed overnight (17 hours). NMR showed complete reaction. The xylene was evaporated and the dark residue was Kugelrohr distilled. There was 3.3 g of pale orange oil collected.

All three oxazole products were combined and purified by chromatography (10% EtOAc/cyclohexane) and then Kugelrohr distilled. The product (4.58 g) was recovered as a colorless oil. $n_D{}^{25}=1.4836$ (54% yield)

EXAMPLE 5

3-pyridinecarboxylic acid, 6-(difluoromethyl)-4-(2-methylpropyl)-5-(2-thiazolyl)-2-(trifluoromethyl)-, methyl ester Several experiments were run in an attempt to work out a procedure for the preparation of this compound. All gave a low yield of the thiazole. It was found that an intermediate of unknown identity, when pyrolyzed, yielded the thiazole. The following is an example of one experiment.

3-pyridinecarboxylic acid, 6-(difluoromethyl)-5-[[(2,2-dimethoxyethyl)amino]carbonyl]-4-(2-methylpropyl)-2-(trifluoromethyl)-, methyl ester prepared from the acid halide used in Example 1 (11.36 g=0.0257 mole), 100 mole toluene and 5.89 g $P_2S_5$ (0.0265 mol) were refluxed together for approximately 3 hours. The reaction was followed by gas chromatography and the assays showed the thiazole to be present. It was washed with $NaHCO_3$(aqueous) and extracted with ether. The ether layer was dried with $MgSO_4$, filtered and concentrated to 12.88 g glassy orange solid. TLC shows a lot of material at the origin when using 5% EtOAc/cyclohexane. An attempt was made to chromatograph the crude product in this solvent system but it would not dissolve. The liquid phase was decanted and then purified by liquid chromatography. Only 0.4 g product was recovered. The insoluble material was shown by gas chromatography to contain the thiazole but TLC did not detect it. At this point it became apparent that a reaction was occurring on the gas chromatographic column. A small sample was heated in a capillary tube to 240° C. and then assayed by TLC. This showed thiazole was formed by pyrolysis. An empty flask was heated by a mantle to an air temperature of 180° C. and then approximately 3 g of glassy solid intermediate was added. After a few seconds it had turned very dark so the heat source was removed. The dark residue contained thiazole as shown by TLC. It was Kugelrohr distilled at 130° C. and then chromatographed in 10% EtOAc/cyclohexane to give 0.7 g yellow solid. (11% yield) This material was combined with products from other experiments, purified by chromatography in 10% EtOAc/cyclohexane and Kugelrohr distilled at 120° C. to give 1.60 g of product as a yellow solid. m.p. 71°–75° C.

EXAMPLE 6

Pyridine, 2-(difluoromethyl)-3,5-bis(4,5-dihydro-2-oxazolyl)-4-(2-methylpropyl)-6-(trifluoromethyl)-

Pyridine, 3,5-bis(chlorocarbonyl)-6-difluoromethyl-4-(2-methylpropyl)-2-(trifluoromethyl) (8.25 g=0.022 mole) and 70 ml $CH_2Cl_2$ were combined and cooled in an ice bath before adding in 6 ml (0.099 mol) of ethanolamine. A precipitate formed immediately. After 15 minutes the ice bath was removed. The mixture was stirred for 2 hours at room temperature. The $CH_2Cl_2$ layer was assayed by $^{19}F$ NMR which showed no pyridine product to be present. Therefore, the product was insoluble in $CH_2Cl_2$. The reaction mixture was washed with $H_2O$ and extracted twice with ethyl acetate. The ethyl acetate layer was dried with MgSO$_4$, filtered and concentrated to 8.78 g of white solid. (94% yield)

The bis-hydroxyethylamide (2.67 g=0.0062 mole) and 40 ml POCl$_3$ were refluxed together for approximately 3½ hours. The POCl$_3$ was evaporated and the residue was washed with H$_2$O and extracted with EtOAc. The EtOAc layer was dried with MgSO$_4$, filtered and concentrated to 2.58 g of tan solid (90% yield). A small sample was purified by chromatography in 20% EtOAc/cyclohexane to give 3,5-pyridinedicarboxamide, N,N'-bis(2-chloroethyl)-2-(difluoromethyl)-4-(2-methylpropyl)-6-(trifluoromethyl)- as a white solid. m.p. 266°-268° C.

This intermediate (2.18 g=0.0047 mole) and 50 ml dry THF were combined and cooled in an ice bath before adding 1.13 g of t-BuOK (0.0101 mole). There was a slight color change and a precipitate noted. After ½ hour the ice bath was removed. $^{19}$F NMR and gas chromatography showed complete reaction. The reaction was washed with NaCl(aqueous) and extracted with ether. The ether layer was dried with MgSO$_4$, filtered and concentrated to 2.0 g pale yellow solid. This was purified by chromatography in 50% EtOAc/cyclohexane to give 1.8 g of solid. This was recrystallized from hexanes to give 1.2 g of product as cream-colored crystals (65% yield). m.p. 138°-144° C.

EXAMPLE 7

Pyridine, 2-(difluoromethyl)-3,5-bis(4,5-dihydro-2-thiazolyl)-4-(2-methylpropyl)-6-(trifluoromethyl)-

The bis-hydroxyethylamide prepared in the first step of Example 6 (7.65 g=0.018 mole), 10 ml HMPA, 60 ml of xylene and 4.03 g of P$_2$S$_5$ (0.018 mole) were combined and heated at reflux for approximately 3½ hours. After this time the reaction showed two liquid phases. Then 4.1 g of P$_2$S$_5$ was added and reflux continued for another hour. The mixture remained non-homogeneous. It was cooled and then filtered through silica gel using 30% EtOAc/cyclohexane. A yellow oil was recovered (8.5 g) which still contained some HMPA by $^1$H NMR. This material was purified by chromatography using 20% EtOAc/cyclohexane. About 3 g of a yellow solid was recovered. This was recrystallized twice from hexane to give 1.21 of the product as white crystals. m.p. 134°-136° C. (22% yield)

EXAMPLE 8

Pyridine, 4-cyclobutyl-2-(difluoromethyl)-3,5-bis(4,5-dihydro-2-oxazolyl)-6-(trifluoromethyl)-

A solution of 13.5 g (0.036 mol) of pyridine, 3,5-bis(-chlorocarbonyl)-4-cyclobutyl-2-(difluoromethyl)-6-(trifluoromethyl)- in 80 ml of dichloromethane was cooled to 0° C. under a nitrogen atmosphere. To it was added dropwise 9.8 ml of ethanolamine. A precipitate formed immediately and the solution became so viscous that 70 ml additional dichloromethane was added so that stirring could continue. The reaction mixture was stirred in the cold for 15 minutes then at room temperature for 3 hours. The reaction solution was poured into water and extracted seven times with ethyl acetate. The combined organic layers were dried over anhydrous magnesium sulfate, filtered, and concentrated to afford 13.2 g (87%) of white powdery solid of 3,5-pyridinedicarboxamide, N,N'-bis(2-hydroxyethyl)-4-cyclobutyl-2-(difluoromethyl)-6-(trifluoromethyl)-.

A 6.0 g (0.014 mol) sample of the above intermediate was refluxed in 100 ml of thionyl chloride for 2.5 hours. The thionyl chloride was then removed by rotary evaporation. The residue was taken up in dichloromethane and washed with water. The organic layer was dried over anhydrous magnesium sulfate to give 2.8 g (42%) of crude product. Two grams of crude product was used directly in a further reaction and 0.8 g was purified for analysis. The crude product was subjected to chromatography using 50% ethyl acetate in cyclohexane to afford 0.70 g (87% recovery) of 3,5-pyridinedicarboxamide, N,N'-bis(2-chloroethyl)-4-cyclobutyl-2-(difluoromethyl)-6-(trifluoromethyl)-, as a white solid (m.p. 246°-247° C.).

A solution of 2.0 g (0.0043 mol) of this intermediate in 40 ml of dry THF was cooled to 0° C. under a nitrogen atmosphere. Then was added 1.04 g (0.0093 mol) of potassium t-butoxide all at once. The reaction color immediately changed from colorless to red and then thirty minutes later to dark brown. The reaction mixture was stirred in the cold for 30 minutes and then at room temperature for 45 minutes. GLC assay shows no starting material at that time so the solution was poured into NaCl/H$_2$O and extracted with ethyl ether. The organic layer was dried over anhydrous magnesium sulfate, filtered, and concentrated to afford 1.6 g (95%) of crude product. The crude product was chromatographed using 20% ethyl acetate in cyclohexane to yield 0.95 g (56%) of product, as a white solid (m.p. 186°-187° C.).

| Elemental Analysis: | C | H | N |
|---|---|---|---|
| Calculated | 52.45 | 4.14 | 10.79 |
| Found | 52.50 | 4.18 | 10.77 |

EXAMPLE 9

3-pyridinecarbothioic acid, 6-(difluoromethyl)-5-(4,5-dihydro-2-thiazolyl)-4-(2-methylpropyl)-2-(trifluoromethyl)-, S-methyl ester A solution of 2.5 ml of ethanolamine (0.0394 mole) in 50 ml CH$_2$Cl$_2$ was cooled by an ice bath before adding 7.28 g of 3-pyridinecarbothioic acid, 5-(chlorocarbonyl)-6-(difluoromethyl)-4-(2-methylpropyl)-2-(trifluoromethyl)-, S-methyl ester (0.0187 mole) in 70 ml CH$_2$Cl$_2$ dropwise. The bath was removed and the mixture was stirred magnetically for two hours. The reaction sat overnight before workup. It was washed with NaCl(aqueous) and extracted with more CH$_2$Cl$_2$. The CH$_2$Cl$_2$ layer was collected, dried with MgSO$_4$, filtered and concentrated to an orange oil. This was dissolved in ethyl acetate and filtered through silica gel. After concentrating, 6.44 g was recovered. 85% yield. A 1.4 g sample was chromatographed in 40% EtOAc/cyclohexane. A pale colored oil (1.16 g) was recovered which gradually solidified. This was recrystallized from 10% EtOAc/hexane. There was recovered 0.92 g white crystals: m.p. 102°-106° C.

This intermediate (6.15 g=0.0148 mole), 100 ml of xylene and 3.52 g P$_2$S$_5$ (0.0157 mole) were combined and refluxed for one hour. A gas chromatographic assay of the xylene phase showed complete reaction. It was washed with NaHCO$_3$ (aqueous) and extracted with ether and ethyl acetate. A residue which stuck to the walls of the reaction flask was also treated with NaHCO$_3$ (aqueous) and extracted as above. The organic phases were combined, dried with MgSO$_4$, filtered and concentrated to a dark oil. This was Kugelrohr distilled at 140° C. to give 4.4 g of an orange oil. This was chromatographed in 10% EtOAc/cyclohexane, to give 2.7 g of product as a colorless oil which gradually solidified (44% yield) m.p. 97°-99° C.

EXAMPLE 10

3-pyridinecarboxylic acid, 6-(difluoromethyl)-5-(5,6-dihydro-4H-1,3-oxazin-2-yl)-4-(2-methylpropyl)-2-(trifluoromethyl)-, methyl ester To 8.4 g (22.5 mmol) of acid chloride starting material used in Example 1 in 50 ml of methylene chloride were added 5.4 g of 3-bromopropylamine hydrobromide and 5.5 g of potassium carbonate. The mixture was stirred at room temperature for one hour and then 20 ml of water was added. Stirring was continued for 18 hours. After that the organic layer was separated, washed with brine and concentrated. The oily residue was triturated with cyclohexane to give a solid. A 2.3 g analytically pure sample was obtained by chromatography of 2.6 g of crude 3-pyridinecarboxylic acid, 5-[[(3-bromopropyl)amino]carbonyl]-6-(difluoromethyl)-4-(2-methylpropyl)-2-(trifluoromethyl)-, methyl ester on silica gel columns with 20% ethyl acetate/cyclohexane as eluting solvent, m.p. 107°-110° C.

To 2.4 g (5 mmol) of this material in 10 ml of methylene chloride containing 0.5 g of benzyltriethylammonium chloride was added in one portion 10 ml of 50% sodium hydroxide solution and the resulting reaction mixture was stirred at room temperature for 2 hours. Additional water and methylene chloride were added and the two layers were separated. The organic layer was washed with brine, dried and concentrated. The oily residue was chromatographed on silica gel (1:5 ethyl acetate-cyclohexane) to afford 1.4 g (70%) of product as colorless oil n$_D^{25}$ 1.4711.

Anal. Calc'd. for C$_{17}$H$_{19}$F$_5$N$_2$O$_3$: C, 49.68; H, 5.36; Cl, 25.94; N, 3.41. Found: C, 49.78; H, 5.41; Cl, 25.81; N, 3.40

EXAMPLE 11

3-pyridinecarboxylic acid, 6-(difluoromethyl)-5-(5,6-dihydro-4H-1,3-thiazin-2-yl)-4-(2-methylpropyl)-2-(trifluoromethyl)-, methyl ester A mixture of 5 g (10 mmol) of intermediate of Example 10 and 2.4 g of phosphorous pentasulfide was heated in 30 ml of xylene at 120°-130° C. for 1½ hours, then cooled and the xylene solution was decanted. The gummy precipitate was dissolved in methylene chloride and 2.5N sodium hydroxide solution. The organic layer was separated, washed with water, brine, dried and concentrated. The crude product was purified by flash chromatography on silica gel (25% ethyl acetate/cyclohexane): yield 0.9 g (22%), m.p. 93°-97° C.

Anal. Calc'd. for C$_{17}$H$_{19}$F$_5$N$_2$O$_2$S$_1$: C, 49.76; H, 4.63; N, 6.83; S, 7.80. Found: C, 49.64; H, 4.66; N, 6.78; S, 7.88

EXAMPLE 12

3-pyridinecarbothioic acid, 6-(difluoromethyl)-5-(4,5-dihydro-1H-imidazol-2-yl)-4-(2-methylpropyl)-2-(trifluoromethyl)-, S-methyl ester To a solution of 3-pyridinecarbothioic acid, 5-(chlorocarbonyl)-6-(difluoromethyl)-4-(2-methylpropyl)-2-(trifluoromethyl)-, S-methyl ester (10 g, 0.0256 mol) in CH$_2$Cl$_2$ (30 mL was added 5.74 g (0.0282 mol) of 2-aminoethylbromide hydrobromide salt. The mixture was cooled at ice bath and to it was added 9.8 mL (0.056 mol) of ethyldiisopropylamine. The reaction was followed by thin layer chromatograph (silica gel, CH$_2$Cl$_2$). After 20 minutes at 0° C., a major product was formed with no detectable amount of starting material. The mixture was worked up by pouring into water, extracted with CH$_2$Cl$_2$. The CH$_2$Cl$_2$ layer was washed with water, dried with anhydrous magnesium sulfate, and concentrated to give 12.2 g of a light brown solid (100% yield). A 10.18 g sample of this solid was purified by liquid chromatograph (10% EtOAc/cyclohexane) to give 7.8 g of 3-pyridinecarbothioic acid, 5-[[(2-bromoethyl)amino]carbonyl]-6-(difluoromethyl)-4-(2-methylpropyl)-2-(trifluoromethyl)-, S-methyl ester (76% yield) as a white solid: m.p. 139° C. (softened at 123° C. and resolidified at 135° C.).

To a solution of this intermediate (1.5 g, 0.0031 mol) in carbon tetrachloride (50 ml) was added 1 g of phosphorus pentachloride. The mixture was refluxed for 1 hour. The reaction gave only one major product as evidenced by $^1$H NMR. The excess reagents were removed by rotary evaporator. To the residual colorless oil was added 30 ml CH$_2$Cl$_2$ and the mixture was cooled at ice-bath temperature. To it was added aqueous ammonia (20 ml). The mixture was stirred at ice bath for 40 minutes and then worked up by pouring into water, and extracting with CH$_2$Cl$_2$. The CH$_2$Cl$_2$ layer was washed with water, dried with anhydrous magnesium sulfate, concentrated to give 1.06 g of a white-foam solid as product (86% yield): m.p. 136°-142° C.

EXAMPLE 13

3-pyridinecarbothioic acid, 5-(1-amino-4,5-dihydro-1H-imidazol-2-yl)-6-(difluoromethyl)-4-(2-methylpropyl)-2-(trifluoromethyl)-, S-methyl ester To a solution of the intermediate of Example 12 (1.5 g, 0.0031 mol) in carbon tetrachloride (50 ml) was added 1 g of phosphorus pentachloride. The mixture was refluxed for 1 hour. The reaction gave only one major product as evidenced by $^1$H NMR. The excess reagents were removed by rotary evaporator. To the residual colorless oil was added 30 ml of CH$_2$Cl$_2$ and cooled at ice-bath temperature. To it was added 0.6 ml of hydrazine hydrate (85%) and 1 ml of ethyldiisoproamine. The mixture was stirred at room temperature overnight and then worked up by pouring into water and extraction with CH$_2$Cl$_2$. The CH$_2$Cl$_2$ layer was washed with water, dried with anhydrous magnesium sulfate, concentrated to give 1.15 g of a light yellow solid. It was purified by chromatography (50% EtOAc/cyclohexane) to give 0.56 g of product as a light yellow solid (44% yield): m.p. 161°-163° C.

EXAMPLE 14

3-pyridinecarboxylic acid, 2-(difluoromethyl)-5-(3-methyl-2-oxazolidinyl)-4-(2-methylpropyl)-6-(trifluoromethyl)-, methyl ester A mixture of 2 g (0.00589 mol) of 3-pyridinecarboxylic acid, 5-(formyl)-2-(difluoromethyl)-4-(2-methylpropyl)- 6-(trifluoromethyl)-, methyl ester, 1.32 g (0.01768 mol) of N-methylethanolamine, and about 0.2 ml water in about 30 ml of toluene with two crystals of p-toluene sulfonic acid as a catalyst was refluxed in a Dean Stark trap for 8 hours after which the reaction was complete. The product was concentrated in vacuo followed by Kugelrohr distillation (120° at 0.5 torr) to give 1.78 g of product as a light yellow oil which solidified on standing, m.p. 50°-53° C., yield 76%.

EXAMPLE 15

3-pyridinecarbothioic acid, 6-(difluoromethyl)-5-(5-methyl-1,3,4-oxadiazol-2-yl)-4-(2-methylpropyl)-2-(trifluoromethyl)-, S-methyl ester In an oven-dried flask was placed 3.8 g of acetylhydrazide in 30 ml of dichloromethane (freshly opened bottle). The flask was cooled to 0° C. and to this was added a solution of 10.0 g (0.026 mol) of the starting material of Example 12 in 40 ml of dichloromethane. (All previous steps were done under a $N_2$ atmosphere). The acid chloride addition lasted 30 minutes, during which time the solution began to turn cloudy. After addition was complete, the solution was stirred at room temperature for 3 hours.

During this time a white precipitate was observed. After the 3 hours of stirring, GLC assay showed no starting material. The reaction solution was filtered, collecting the white precipitate. The filtrate was poured into $H_2O$ and extracted with $CH_2Cl_2$. The organic layer was washed once with water and dried over anhydrous $MgSO_4$. Concentration gave 4.5 g of crude material, which was purified further by chromatography to give 3.2 g. Total yield of 3-pyridinecarbothioic acid, 5-[(2-acetylhydrazino)carbonyl]-6-(difluoromethyl)-4-(2-methylpropyl)- 2-(trifluoromethyl)-, S-methyl ester was 6.7 g, m.p. 186°-187° C.

A mixture of 4.0 g (0.0093 mol) of this intermediate, 7.3 ml of phosphorus oxychloride, and 2.57 g (0.012 mol) of phosphorus pentachloride was heated at reflux. The mixture became homogeneous and clear. After one hour at reflux, an aliquot of reaction mixture was removed and concentrated. The residue was treated with 1-2 ml of ice water and extracted with 2 ml of dichloromethane. TLC in 50% ethyl acetate in cyclohexane showed no starting material so the heat was turned off and the reaction flask was cooled to room temperature. The flask was placed on a rotary evaporator and the contents were evaporated to leave an oily residue. The residual oil was treated with ice/$H_2O$ and extracted with $2 \times 50$ ml of dichloromethane and $1 \times 40$ ml of ethyl ether. The organics were dried over anhydrous $MgSO_4$, filtered, and concentrated to afford 4.0 g of crude dark yellow oil. Purification by chromatography (20% ethyl acetate in cyclohexane) afforded 1.5 g (39% yield) of product as a yellow oil.

EXAMPLE 16

3-pyridinecarboxylic acid, 2-(difluoromethyl)-5-(4,5-dihydro-1-methyl-1H-imidazol-2-yl)-4-(2-methylpropyl)-6-(trifluoromethyl)-, methyl ester To a 20 g (0.054 mol) solution of the 3-pyridinecarboxylic acid, 5-(chlorocarbonyl)-4-(2-methylpropyl)-6-(trifluoromethyl)-, methyl ester in dichloromethane was added 12.0 g (0.059 mol) of 2-bromoethylamine hydrobromide and the solution was cooled in an ice bath. Then 10.2 ml (0.059 mol) of N,N-diisopropylethylamine was added dropwise over 5 minutes. The solution was stirred for 30 minutes and then the ice bath was removed. Some solid started to form. The solution was stirred at room temperature and monitored by TLC (20% EtoAC/cyclohexane) and $^{19}F$ NMR. It was stirred overnight at room temperature. In the morning an additional 1.1 equivalent (10.2 ml) of ethyl diisopropylamine was added and let stir. In one hour TLC showed no starting material. The reaction solution was poured into $H_2O$ and extracted with $CH_2Cl_2$. The organic layer was dried over anhydrous $MgSO_4$, filtered, and concentrated to yield 24.5 g (99%) of crude light yellow oil. This was purified by chromatography using (15% EtoAC/cyclohexane) to yield 3-pyridinecarboxylic acid, 5-[[(2-bromoethyl)amino]carbonyl]-2-(difluoromethyl)-4-(2-methylpropyl)-6-(trifluoromethyl)-, methyl ester as a white solid: 14 g (57%).

A solution of 2.0 g (0.0043 mol) of this intermediate in 20 ml of $CCl_4$ was refluxed with 1.8 g (0.0086 mol) of phosphorus pentachloride. The solution became homogeneous and clear upon heating. One hour later $^{19}F$ NMR showed a new set of peaks. The solution was allowed to stir an additional hour. $^1H$ NMR shows no NH peak at this time. The solvents were evaporated and the flask was placed under vacuum for 3 hours to yield 2.1 g of a white semisolid product. This semisolid product was taken up in 25 ml of dichloromethane and chilled to 0° C. Then 20 ml of aqueous methylamine (40%) was added dropwise over 10 minutes. The solution was allowed to stir overnight at room temperature. The next morning, GLC showed reaction was complete. The reaction solution was poured into $H_2O$ and extracted with $CH_2Cl_2$. The organics were dried over anhydrous $MgSO_4$, filtered, and concentrated to give 1.5 g (87%) of crude yellow oil. Purification by chromatography using 50% ethyl acetate in cyclohexane yielded 1.1 g (64%) of product as an orange oil.

EXAMPLE 17

3-pyridinecarboxylic acid, 2-(difluoromethyl)-5-(4,5-dihydro-5-methyl-2-thiazolyl)-4-(2-methylpropyl)-6-(trifluoromethyl)-, methyl ester 3-pyridinecarboxylic acid, 5-(chlorocarbonyl)-2-(difluoromethyl)-4-(2-methylpropyl)-6-(trifluoromethyl)-, methyl ester (5.26 g=0.0141 mole), 50 ml $CH_2Cl_2$ and 2.5 ml 1-amino-2-propanol were combined at room temperature. After 1.5 hours $^{19}F$ NMR showed the reaction was complete. The mixture was washed with dilute HCl and extracted with $CH_2Cl_2$. The $CH_2Cl_2$ layer was dried with $MgSO_4$, filtered and concentrated to 5.28 g glass. After drying under vacuum, 5.0 g of 3-pyridinecarboxylic acid, 2-(difluoromethyl)-5-[[(2-hydroxypropyl)amino]carbonyl]-4-(2-methylpropyl)-6-(trifluoromethyl)-, methyl ester was obtained. Yield was 86%.

This intermediate (4.43 g=0.0107 mole), 50 ml of xylenes and 2.58 g of $P_2S_5$ were refluxed overnight. The organic liquid phase was decanted from an oily residue stuck to the walls of the flask. It was washed with NaHCO$_3$(aqueous and extracted with ether. The ether layer was dried with $MgSO_4$, filtered and concentrated to 2.9 g of orange oil. A gas chromatographic assay showed it was 99% pure. The residue in the reaction flask was then treated similarly. A dark oil was recovered which was 83% pure by gas chromatographic. This was chromatographed in 5% EtOAc/cyclohexane. The best materials were combined and Kugelrohr distilled at 120° C. to give 2.6 g product as a yellow oil, $n_D^{25}$ 1.4935. 60% yield.

EXAMPLE 18

3-pyridinecarboxylic acid,
2-(difluoromethyl)-5-(4,5-dihydro-2-thiazolyl)-4-(2-methylpropyl)-6-(trifluoromethyl)-, methyl ester 3-Pyridinecarboxylic acid, 2-(difluoromethyl)-5-{[(2-hydroxyethyl)amino]carbonyl}-4-(2-methylpropyl)-6-(trifluoromethyl)-, methyl ester (5.0 g=0.0127 mole), 50 mL xylenes and 1.79 g $P_2S_5$ (0.0081 mole) were combined and heated at reflux for one hour. A GC assay showed what appeared to be starting material and product, so 0.62 g $P_2S_5$ (0.0028 mole) was added and reflux continued for another three hours. At this time, a GC assay showed complete reaction. Heating was stopped and the reaction mixture sat at room temperature for four days before workup. It was then treated with NaHCO$_3$(aqueous) and extracted with ether. There was a bad emulsion problem. The ether layer was dried with MgSO$_4$, filtered, and concentrated to a dark orange oil. This was Kugelrohr distilled to give 3.9 g pale yellow oil which solidified. This was recrystallized from hexanes to give 2.61 g of pale orange crystals (52% yield). mp 79°–81° C.

EXAMPLE 19

3-Pyridinecarboxylic acid,
2-(difluoromethyl)-5-(1,3-dithiolan-2-yl)-4-(2-methylpropyl)-6-(trifluoromethyl)-, methyl ester A mixture of product of Step 11 (1.78 g=0.0053 mole), 20 mL CH$_2$Cl$_2$, and 0.5 mL ethanedithiol were cooled in an ice bath under N$_2$ before adding 0.2 mL TiCl$_4$. A yellow solid formed. The reaction mixture was warmed slowly to room temperature and was stirred overnight and poured into NaCl(aqueous) and extracted with CH$_2$Cl$_2$. The CH$_2$Cl$_2$ layer was dried with MgSO$_4$, filtered and concentrated to 2.2 g oil. This was Kugelrohr distilled in fraction to give 1.9 g (86%) of product, $n_D^{25}$=1.5180, bp 120° C. (0.1 torr).

EXAMPLE 20

3-Pyridinecarboxylic acid,
2-(difluoromethyl)-5-(1,3-dithian-2-yl)-4-(2-methylpropyl)-6-(trifluoromethyl)-, methyl ester A mixture of product of Step 11 (1.7 g=0.005 mole), 20 mL CH$_2$Cl$_2$ and 0.6 mL 1,3-propanedithiol were cooled in an ice bath before adding 0.3 mL TiCl$_4$. A solid formed immediately. After 15 minutes the bath was removed. One hour later a GC assay showed complete reaction. It was washed with NaCl (aqueous) and extracted with CH$_2$Cl$_2$. The CH$_2$Cl$_2$ layer was dried with MgSO$_4$, filtered and concentrated to a colorless oil. This was Kugelrohr distilled at 130° C. to give 1.95 g of product as an oil which gradually solidified. 91% yield; mp 72°–76° C.

EXAMPLE 21

3-Pyridinecarboxylic acid, 5-4,5-dihydro-2-thiazolyl)-4-(2-methylpropyl)-2,6-bis(trifluoromethyl)-, methyl ester A mixture of 10.1 g (~0.025 mol) of 2,6-bis(trifluoromethyl)-4-(2-methylpropyl)-3,5-pyridinedicarboxylic acid and its monomethyl ester, prepared from partial hydrolysis of dimethyl 2,6-bis(trifluoromethyl)-4-(2-methylpropyl)-3,5-pyridinedicarboxylate, 10 mL (0.11 mol) oxalyl chloride, 2 drops DMF, and 75 mL chloroform is stirred at room temperature for 18 hours and stripped. The residue is dissolved in 200 mL CH$_2$Cl$_2$/100 mL THF and 7 g (0.10 mol) ethanolamine added. The mixture is stirred at ambient temperature for 1 hour and stripped. From work-up with aqueous HCl/ethyl acetate, 8.5 g intermediate is obtained. The intermediate is heated to reflux with 17 g (0.038 mol) phosphorus pentasulfide in 250 mL xylene and held at reflux for 18 hours. Work-up with ether/sodium bicarbonate solution and purification/separation by HPLC (10% ethyl acetate) gives 2.87 g (~50% yield) orange brown solid, mp 92°–5°.

EXAMPLE 22

Pyridine,
3,5-bis(4,5-dihydro-2-thiazolyl)-4-(2-methylpropyl)-2,6-bis(trifluoromethyl)

A second product isolated by HPLC as described in Example 21 is Kugelrohr distilled to give 0.55 g (~10%) tan solid, mp 143°–146° C.

EXAMPLE 23

3-Pyridinecarboxylic acid,
2-(chlorodifluoromethyl)-5-(4,5-dihydro-2-thiazolyl)-4-(2-methylpropyl)-6-(trifluoromethyl)-, methyl ester To a solution of 0.0082 mol lithium diisopropylamide in 30 mL THF at below −65° C. is added a solution of 3.0 g (0.0076 mol) of product of Example 18 in 15 mL THF. The mixture is held at below −65° C. for 20 minutes and 2.2 g (0.009) hexachloroethane in 10 mL THF is added. The mixture is allowed to warm to room temperature. Work-up with CH$_2$Cl$_2$/dilute HCl and Kugelrohr distillation at 150–160/1.2 gives crude product which is purified using a chromatograph (5% ethyl acetate) and recrystallization from hexane to give 0.20 g (6% yield) white solid, mp 114°–6° C.

EXAMPLE 24

3-Pyridinecarboxylic acid,
4-[bis(methylthio)methyl]-6-(difluoromethyl)-5-(4,5-dihydro-2-oxazolyl)-2-(trifluoromethyl)-, methyl ester To a solution of 3.8 g (0.0098 mol) of 3-pyridinecarboxylic acid, 6-(difluoromethyl)-5-(4,5-dihydro-2-oxazolyl)-4-[(methylthio)methyl]-2-(trifluoromethyl)-, methyl ester in 50 mL anhydrous THF in a dry flask under nitrogen is added 40 mL (0.04 mol) 1.0 m lithium bis(trimethylsilyl)amide in hexane, controlling the reaction temperature at −20° to −10° C. After 10 minutes at −10° C., 1.9 mL (0.014 mol) methyl disulfide is added. The reaction mixture is warmed to 20° C., where it is stirred for 3 hours. The reaction mixture is worked up using dilute HCl and ether. The product is purified by HPLC (20% ethylacetate in cyclohexane) and Kugelrohr distilled to give 1.03 g (24% yield) yellow-brown oil, $n_D^{25}$=1.5235, bp 180°–190° C./1.4 torr.

EXAMPLE 25

3-Pyridinecrboxylic acid,
2-(difluoromethyl)-4-i2-methylpropyl]-5-[3-(trifluoroacetyl)-2-thiazolidinyl]-6-(trifluoromethyl)-, methyl ester A mixture of 6.0 g (0.015 mol) of product of Example 18, 6 mL (0.042 mol) trifluoroacetic anhydride, 30 g (0.26 mol) trifluoroacetic acid, 18 g (0.27 mol) zinc dust and 150 mL methylene chloride is heated and held at reflux for 2 hours. Another 1 g zinc dust is added and the mixture held at reflux for 1 hour. The mixture is cooled and filtered, and the filtrate concentrated. Purification by chromatography (40% methylene chloride in cyclohexane) affords 1.88 g (25% yield) of a first fraction as a yellow-green oil.

EXAMPLE 26

3-Pyridinecarboxylic acid, 2-methyl-4-(2-methylpropyl)-5-[3-(trifluoroacetyl)-2-thiazolidinyl]-6-(trifluoromethyl), methyl ester Flushing the HPLC column from Example 25 with methylene chloride elutes the crude product which after chromatography (7% ethyl acetate in cyclohexane) and Kugelrohr distillation yields 0.54 g (7% yield) yellow oil, bp 185°–195° C./1.0 torr.

Further compounds according to this invention were prepared by methods similar to those described above and are shown in the following Table 1 along with a physical property for each where available.

TABLE 1

| Example No. | Compound | M.P./B.P. | $n_D^{25}$ |
|---|---|---|---|
| 27 | 3-pyridinecarboxylic acid, 6-(difluoromethyl)-5-(4,5-dihydro-2-oxazolyl)-4-(2-methylpropyl)-2-(trifluoromethyl)-, methyl ester | 87.0–89.0 | |
| 28 | 3-pyridinecarboxylic acid, 2-(difluoromethyl)-5-(4,5-dihydro-2-oxazolyl)-4-(2-methylpropyl)-6-(trifluoromethyl)-, methyl ester | 85.0–87.0 | |
| 29 | 3-pyridinecarboxylic acid, 6-(difluoromethyl)-5-(4,5-dihydro-2-oxazolyl)-4-(1-methylethyl)-2-(trifluoromethyl)-, methyl ester | 81.0–83.0 | |
| 30 | 3-pyridinecarboxylic acid, 6-(difluoromethyl)-5-(4,5-dihydro-2-thiazolyl)-4-(2-methylpropyl)-2-(trifluoromethyl)-, methyl ester | 101.0–103.0 | |
| 31 | 3-pyridinecarboxylic acid, 2-(difluoromethyl)-5-(4,5-dihydro-2-oxazolyl)-4-(1-methylethyl)-6-(trifluoromethyl)-, methyl ester | 67.0–68.0 | |
| 32 | 3-pyridinecarboxylic acid, 2-(difluoromethyl)-5-(4,5-dihydro-2-oxazolyl)-4-propyl-6-(trifluoromethyl)-, methyl ester | 40.0–41.0 | |
| 33 | 3-pyridinecarboxylic acid, 2-(difluoromethyl)-5-(5-methoxy-2-oxazolyl)-4-(2-methylpropyl)-6-(trifluoromethyl)-, methyl ester | 80.0–82.0 | |
| 34 | 3-pyridinecarboxylic acid, 4-(cyclopropylmethyl)-2(difluoromethyl)-5-(4,5-dihydro-2-thiazolyl) 6-(trifluoromethyl)-, methyl ester | | 1.5090 |
| 35 | 3-pyridinecarboxylic acid, 4-(cyclopropylmethyl) 2-(difluoromethyl)-5-(4,5-dihydro-2-oxazolyl) 6-(trifluoromethyl)-, methyl ester | 63.0–65.0 | |
| 36 | 3-pyridinecarboxylic acid, 2-(difluoromethyl)-5-(4,5-dihydro-2-thiazolyl)-4-(2-methylpropyl)-6-(trifluoromethyl)-, S-methyl ester | 74.0–76.0 | |
| 37 | 3-pyridinecarboxylic acid, 4-(cyclobutyl-2-(difluoromethyl)-5-(4,5-dihydro-2-oxazolyl)-6-(trifluoromethyl)-, methyl ester | 88.0–89.0 | |
| 38 | 3-pyridinecarboxylic acid, 4-cyclobutyl-2-(difluoromethyl)-5-(4,5-dihydro-2-thiazolyl)-6-(trifluoromethyl)-, methyl ester | 75.0–77.0 | |
| 39 | 3-pyridinecarboxylic acid, 2-(difluoromethyl)-5-(4,5-dihydro-2-thiazolyl)-4-(2-methylethyl)-6-(trifluoromethyl)-, methyl ester | 125.0 @ 0.400 torr | |
| 40 | 3-pyridinecarboxylic acid, 2-(difluoromethyl)-5-(4,5-dihydro-2-thiazolyl)-4-propyl-6-(tri-(trifluoromethyl)-, methyl ester | 125.0 @ 0.250 torr | |
| 41 | 3-pyridinecarbothioic acid, 2-(difluoromethyl)-5-(4,5-dihydro-2-oxazolyl)-4-(2-methylpropyl-6-(trifluoromethyl)-, S-methyl ester | 95.0–97.0 | |
| 42 | 3-pyridinecarbothioic acid, 4-(cyclopropylmethyl)-2-(difluoromethyl)-5-(4,5-dihydro-2-thiazolyl)-6-(trifluoromethyl)-, S-methyl ester | 91.0–95.0 | |
| 43 | 3-pyridinecarbothioic acid, 4-(cyclopropylmethyl)-2-(difluoromethyl)-5-(4,5-dihydro-2-oxazolyl)-6-(trifluoromethyl)-, S-methyl ester | 67.0–72.0 | |
| 44 | 3-pyridinecarboxylic acid, 2-(difluoromethyl)-4-(2-methylpropyl)-5-(2-thiazolyl)-6-(trifluoromethyl)-, methyl ester | 57.0–60.0 | |
| 45 | 3-pyridinecarbothioic acid, 4-(cyclopropylmethyl)-6-(difluoromethyl)-5-(4,5-dihydro-2-thiazolyl)-2-(trifluoromethyl)-, S-methyl ester | 127.0–130.0 | |
| 46 | 3-pyridinecarbothioic acid, 4-(cyclopropylmethyl)-6-(difluoromethyl)-5-(4,5-dihydro-2-oxazolyl)-2-(trifluoromethyl)-, S-methyl ester | 109.0–113.0 | |
| 47 | pyridine, 2-(difluoromethyl)-5-(4,5-dihydro-2-thiazolyl)-4-(2-methylpropyl)-3-(1H-pyrazol-1-ylcarbonyl)-6-(trifluoromethyl)- | 99.0–102.0 | |
| 48 | 3-pyridinecarbothioic acid, 4-cyclobutyl-6-(difluoromethyl)-5-(4,5-dihydro-2-oxazolyl)-2-(trifluoromethyl)-, S-methyl ester | 118.0–119.0 | |

TABLE 1-continued

| Example No. | Compound | M.P./B.P. | $n_D^{25}$ |
|---|---|---|---|
| 49 | 3-pyridinecarboxylic acid, 4-cyclobutyl-6-(difluoromethyl)-5-(4,5-dihydro-2-thiazolyl)-2-(trifluoromethyl)-, methyl ester | 112.0–113.0 | |
| 50 | 3-pyridinecarbothioic acid, 4-cyclobutyl-6-(difluoromethyl)-5-(4,5-dihydro-2-thiazolyl)-2-(trifluoromethyl)-, S-methyl ester | 138.0–139.0 | |
| 51 | 3-pyridinecarboxylic acid, 4-cyclobutyl-6-(difluoromethyl)-5-(4,5-dihydro-2-oxazolyl)-2-(trifluoromethyl)-, methyl ester | 105.0–107.0 | |
| 52 | 3-pyridinecarboxylic acid, 2-(difluoromethyl)-5-(5-methyl-1,3,4-oxadiazol-2-yl)-4-(2-methylpropyl)-6-(trifluoromethyl)-, methyl ester | 80.0–83.0 | |
| 53 | 3-pyridinecarboxylic acid, 6-(difluoromethyl)-5-(4,5-dihydro-2-thiazolyl)-4-methyl-2-(trifluoromethyl)-, methyl ester | 128.0–130.0 | |
| 54 | 3-pyridinecarboxylic acid, 6-(difluoromethyl)-5-(4,5-dihydro-2-oxazolyl)-4-methyl-2-(trifluoromethyl)-, methyl ester | 118.0–120.0(m.p.) 125.0–135.0(b.p.) @ 1.300 torr | |
| 55 | 3-pyridinecarboxylic acid, 6(difluoromethyl)-5-(4,5-dihydro-2-oxazolyl)-4-[(methylthio)methyl]-2-(trifluoromethyl)-, methyl ester | 102.0–104.0 | |
| 56 | 3-pyridinecarboxylic acid, 6-(difluoromethyl)-5-(4,5-dihydro-2-thiazolyl)-4-[(methylthio)methyl]-2-(trifluoromethyl)-, methyl ester | 88.0–90.0(m.p.) 175.0–185.0(bp) @ 1.200 torr | |
| 57 | 3-pyridinecarbothioic acid, 6-(difluoromethyl)-5-(5,6-dihydro-4H-1,3-oxazin-2-yl)-4-(2-methylpropyl)-2-(trifluoromethyl)-, S-methyl ester | | 1.5009 |
| 58 | 3-pyridinecarbothioic acid, 6-(difluoromethyl)-5-(5,6-dihydro-4H-1,3-thiazin-2-yl)-4-(2-methylpropyl)-2-(trifluoromethyl)-, S-methyl ester | 71.0–75.0 | |
| 59 | 3-pyridinecarboxylic acid, 2-(difluoromethyl)-5-(5,6-dihydro-4H-1,3-thiazin-2-yl)-4-(2-methylpropyl)-6-(trifluoromethyl)-, methyl ester | | 1.5008 |
| 60 | 3-pyridinecarboxylic acid, 2-(difluoromethyl)-5-(5,6-dihydro-4H-1,3-oxazin-2-yl)-4-(2-methylpropyl)-6-(trifluoromethyl)-, methyl ester | | 1.4706 |
| 61 | 3-pyridinecarboxylic acid, 2-(difluoromethyl)-5-(5,6-dihydro-4H-1,3-oxazin-2-yl)-4-(2-methylpropyl)-6-(trifluoromethyl)-, | 190.0–220.0 | |
| 62 | 3-pyridinecarbothioic acid, 2-(difluoromethyl)-5-(5,6-dihydro-4H-1,3-oxazin-2-yl)-4-(2-methylpropyl)-6-(trifluoromethyl)-, S-methyl ester | 60.0–65.0 | |
| 63 | Pyridine, 3,5-bis(5,6-dihydro-4H-1,3-oxazin-2-yl)-2-(difluoromethyl)-4-(2-methylpropyl)-6-(trifluoromethyl) | 108.0–115.0 | |
| 64 | 3-pyridinecarboxylic acid, 2-(difluoromethyl)-5-(4,5,-dihydro-5-methyl-2-oxazolyl)-4-(2-methylpropyl)-6-(trifluoromethyl)-, methyl ester | 110 @ 0.100 torr | |
| 65 | 3-pyridinecarbothioic acid, 2-(difluoromethyl)-5-(4,5-dihydro-5-methyl-2-thiazolyl)-4-(2-methylpropyl)-6-(trifluoromethyl)-, S-methyl ester | 87.0 | |
| 66 | 3-pyridinecarboxylic acid, 2-(difluoromethyl)-5-(4,5-dihydro-4-methyl-2-thiazolyl)-4-(2-methylpropyl)-6-(trifluoromethyl)-, methyl ester | 100 @ 0.100 torr | |
| 67 | 3-pyridinecarboxylic acid, 5-(4,5-dihydro-2-thiazolyl)-6-methyl-4-(2-methylpropyl)-2-(trifluoromethyl)-, methyl ester | 81.0–83.0(m.p.) 155.0–165.0(b.p.) @ 1.200 torr | |
| 68 | 3-pyridinecarboxylic acid, 6-(difluoromethyl)-5-(5,6-dihydro-4H-1,3-thiazin-2-yl)-4-[(methylthio)methyl]-2-(trifluoromethyl)-, ethyl ester | 77.0–79.0(m.p.) 175.0–185.0(b.p.) @ 1.200 torr | |
| 69 | 3-pyridinecarboxylic acid, 6-(difluoromethyl)-5-(5,6-dihydro-4H-1,3-oxazin-2-yl)-4-[(methylthio)methyl]-2-(trifluoromethyl)-, ethyl ester | 170.0–180.0 @ 1.200 torr | |
| 70 | 3-pyridinecarboxylic acid, 6-(difluoromethyl)-5-(5,6-dihydro-6-methyl-4H-1,3-oxazin-2-yl)-4-(2-methylpropyl)-2-(trifluoromethyl)-, methyl ester | | 1.4675 |
| 71 | 3-pyridinecarboxylic acid, 2-(difluoromethyl)-5-(5,6-dihydro-6-methyl-4H-1,3-oxazin-2-yl)-4-(2-methylpropyl)-6-(trifluoromethyl)-, methyl | | 1.4684 |

TABLE 1-continued

| Example No. | Compound | M.P./B.P. | $n_D^{25}$ |
|---|---|---|---|
| | ester | | |
| 72 | 3-pyridinecarboxylic acid, 2-(difluoromethyl)-5-(4,5-dihydro-4-methyl-2-oxazolyl)-4-(2-methylpropyl)-6-(trifluoromethyl)-, methyl ester | 110 @ 0.100 torr | |
| 73 | 3-pyridinecarboxylic acid, 6-(difluoromethyl)-5-(4-ethylidene-4,5-dihydro-5-oxo-2-oxazolyl)-4-(2-methylpropyl)-2-(trifluoromethyl)-, methyl ester | 120 @ 0.100 torr | |
| 74 | 3-pyridinecarboxylic acid, 2-(difluoromethyl)-5-(4-ethylidene-4,5-dihydro-5-oxo-2-oxazolyl)-4-(2-methylpropyl)-6-(trifluoromethyl)-, methyl ester | 130 @ 0.100 torr | |
| 75 | 3-pyridinecarboxylic acid, 6-(difluoromethyl)-5-[4,5-dihydro-5-methyl-5-(1-methylethyl)-4-oxo-1H-imidazol-2-yl]-4-methyl-2-(trifluoromethyl)-, methyl ester | 143.0-146.0 | |
| 76 | 3-pyridinecarboxylic acid, 2-(difluoromethyl)-5-[4,5-dihydro-5-methyl-5-(1-methylethyl)-4-oxo-1H-imidazol-2-yl]-4-methyl-6-(trifluoromethyl)-, methyl ester | | |
| 77 | 3-pyridinecarboxylic acid, 6-(difluoromethyl)-5-(1,3-dithiolan-2-yl)-4-(2-methylpropyl)-2-(trifluoromethyl)-, methyl ester | 145-149.0 | |
| 78 | 3-pyridinecarboxylic acid, 2-(difluoromethyl)-4-(2-methylpropyl)-5-(1,3,4-oxadiazol-2-yl)-6-(trifluoromethyl)-, methyl ester | 120.0-0.0 @ 0.250 torr | |
| 79 | 3-pyridinecarboxylic acid, 6-(difluoromethyl)-5-(1,3-dithian-2-yl)-4-(2-methylpropyl)-2-(trifluoromethyl)-, methyl ester | 115.0-118.0 | |
| 80 | 3-pyridinecarboxylic acid, 4-(cyclopropyl-methyl)-6-(difluoromethyl)-5-(5-methyl-1,3,4-oxadiazol-2-yl)-2-(trifluoromethyl)-, methyl ester | 135.0-0.0 @ 0.300 torr | |
| 81 | 3-pyridinecarboxylic acid, 4-(cyclopropyl-methyl)-2-(difluoromethyl)-5-(5-methyl-1,3,4-oxadiazol-2-yl)-6-(trifluoromethyl)-, methyl ester | 135.0-0.0 @ 0.300 torr | |
| 82 | 3-pyridinecarboxylic acid, 4-(cyclopropyl-methyl)-2-(difluoromethyl)-5-(4,5-dihydro-4-methyl-2-thiazolyl)-6-(trifluoromethyl)-, methyl ester | 115 @ 0.100 | |
| 83 | 3-pyridinecarboxylic acid, 5-(4,5-dihydro-4-methyl-1,3,4-oxadiazol-2-yl)-2-(difluoromethyl)-4-(2-methylpropyl)-6-(trifluoromethyl)-, methyl ester | 125 @ 0.100 torr | |

EXAMPLE 84

3-Pyridinecarbodithioic acid, 2-(difluoromethyl)-5-(4,5-dihydro-2-thiazolyl)-4-(2-methylpropyl)-6-(trifluoromethyl)-, methyl ester A mixture of 5.0 g (0.01261 mole) of 3-pyridinecarboxylic acid, 2-(difluoromethyl)-5-(4,5-dihydro-2-thiazolyl)-4-(2-methylpropyl)-6-(trifluoromethyl)-, methyl ester and 6.1 g (0.01513 mol) of Lawesson's reagent in 45 mL of xylenes and 11 mL of HMPA was refluxed under nitrogen for five hours. Reaction was allowed to cool to room temperature and was then passed through a plug of silica gel (eluted with ethyl acetate:hexanes=1:5). The resulting material was purified by chromatography (ethyl acetate:hexanes=1:10). The resulting orange oil crystallized on standing. Crystals were washed with hexanes to give 1.26 g (23%) of the title compound as orange crystals (MP 102°-106° C.). Anal. Calcd for $C_{16}H_{17}F_5N_2S_3$: C,44.85; H,4.00; N,6.54. Found: C,44.96; H,4.01; N,6.53.

EXAMPLE 85

3-Pyridinecarboxamide, 2-(difluoromethyl)-5-(4,5-dihydro-2-thiazolyl)-N-methyl-4-(2-methylpropyl)-6-(trifluoromethyl)-

A mixture of 12.5 g (0.031 mole) of 3-pyridinecarbonyl chloride, 2-(difluoromethyl)-5-(4,5-dihydro-2-thiazolyl)-4-(2-methylpropyl)-6-(trifluoromethyl)-; 20 mL of a 40% aqueous methylamine solution, 80 mL of water, and 200 mL of methylene chloride were stirred together at room temperature for four hours. The layers were separated and the organic phase was dried over anhydrous magnesium sulfate. Concentration in vacuo gave a crystalline material that was recrystallized from methylene chloridehexanes. Obtained 10.71 g (86%) of the title compound as fine white flakes (MP 203°-205° C.). Anal. Calc'd for $C_{16}H_{18}F_5N_3OS1$: C,48.60; H,4.59; N,10.63. Found: C,48.51; H,4.61; N,10.61.

EXAMPLE 86

3-Pyridinecarbonitrile, 2-(difluoromethyl)-5-(4,5-dihydro-2-thiazolyl)-4-i2-methylpropyl)-6-(trifluoromethyl)-

A mixture of 7.0 g (0.01835 mole) of 3-pyridinecarboxyamide, 2-(difluoromethyl)-5-(4,5-dihydro-2- thiazolyl)-4-(2-methylpropyl)-6-(trifluoromethyl)-, and 40 mL of phosphorus oxychloride were refluxed overnight under nitrogen. The mixture was concentrated in vacuo to give a residue that was taken up in ethyl acetate and washed with a sodium bicarbonate solution. Dried over anhydrous magnesium sulfate and concentrated in vacuo to give a crystalline product. The product was passed through a plug of silica gel (ethyl acetate:hexanes=1:1) followed by recrystallization from methylene chloride-hexanes. Obtained 5.14 g (77%) of the title compound as colorless prisms (MP 106°-107° C.). Anal. Calc'd for $C_{15}H_{14}F_5N_3S_1$: C,49.59; H,3.88; N,11.61. Found: C,49.65; H,3.90; N,11.56.

EXAMPLE 87

3-Pyridinecarboximidothioic acid, 2-(difluoromethyl)-5-(4,5-dihydro-2-thiazolyl)-N-methyl-4-(2-methylpropyl)-6-(trifluoromethyl)-, methyl ester 3-Pyridinecarboxamide, 2-(difluoromethyl)-5-(4,5-dihydro-2-thiazolyl)- N-methyl-4-(2-methylpropyl)-6-(trifluoromethyl)- (3.78 g, 0.00956 mole) and 2.0 g (0.00956 mole) of phosphorous pentachloride were refluxed together in 40 mL of carbon tetrachloride under nitrogen for 15 hours. The reaction mixture was concentrated in vacuo and the resulting oil was taken up in 30 mL of anhydrous dimethylformamide. This solution was treated with 1.0 g (0.01434 mole) of sodium methanethiolate, and was stirred for three hours under nitrogen. The reaction was poured into 150 mL of water followed by extraction with ether. The ether extracts were washed with water then dried over anhydrous magnesium sulfate. Silica gel chromatography (ethyl acetate:hexanes=1:2) gave an oil that was Kugelrohr distilled (160° C.,0.2 mm) to give 1.33 g (33%) of the title compound as a thick yellow oil. Anal. Calc'd for $C_{17}H_{20}F_5N_3S_2$: C,47.99; H,4.74; N,9.88. Found: C,47.89; H,4.77; N,9.84.

EXAMPLE 88

3-Pyridinecarboxylic acid, 2-(difluoromethyl)-5-(4,5-dihydro-2-thiazolyl)-4-(2-methylpropyl)-6-(trifluoromethyl)-, cyanomethyl ester A 3.5 g(0.009 mole) sample of 3-pyridinecarboxylic acid, 2-(difluoromethyl)-5-(4,5-dihydro-2-thiazolyl)-4-(2-methylpropyl)-6-(trifluoromethyl)-, in 65 mL of DMF was stirred with 1.37 g (0.018 mole) of chloroacetonitrile and 2.5 g (0.018 mole) of potassium carbonate at RT for 12 hours. The reaction mixture was poured into dichloromethane and water was added. The layers were separated and the organics were dried over MgSO$_4$. Filtration, concentration, and Kugelrohr distillation gave 2.1 g (55%) of product, which solidified upon standing (m.p. 146°-147° C.). Anal. Calc'd for $C_{17}H_{16}F_5N_3O_2S_1$: C,48.45; H,3.83; N,9.97. Found: C,48.43; H,3.82; N,9.96.

EXAMPLE 89

3-Pyridinecarboxylic acid, 6-(difluoromethyl)-4-(2-methylpropyl)-5-(1-methyl-1H-tetrazol-5-yl)-2-(trifluoromethyl)-, methyl ester A solution of 5 mL of aqueous methylamine in 15 mL of CH$_2$Cl$_2$ was cooled to 5° C. Then was added 3.0 g of 3-pyridinecarboxylic acid, 5-(carbonylchloride)-6-(difluoromethyl)-4-(2-methylpropyl)-2-(trifluoromethyl)-, methyl ester in 20 mL of CH$_2$Cl$_2$. The ice bath was removed and the GLC one hour later shows no starting material. The reaction solution was poured into water and extracted with CH$_2$Cl$_2$. The organics were dried, filtered, and concentrated to give 2.72 g of the amide. The methylamide was taken up in 35 mL of CCl$_4$ and refluxed with 1.5 g of phosphorus pentachloride for 3 hours. $^{19}$FNMR shows reaction complete. The solution was concentrated to dryness and dried under high vacuum for 4 hours to give 2.6 g of a yellow oil, the iminoyl chloride. The 2.6 g (0.0067 mole) sample of the iminoyl chloride was taken up in DMF and placed in an addition funnel. A 100 mL rb flask was charged with 0.82 g (0.012 mol) of sodium azide in 15 mL of DMF and the solution was cooled to 5° C. with an ice bath. The iminoyl chloride solution was then added dropwise to the suspension of sodium azide over 30 minutes. The ice bath was removed and the solution stirred for 25 minutes. The reaction mixture was allowed to sit overnight at RT. Then approximately 4 mL of water was added, just enough to produce a cloudiness, and the flask was cooled in an ice bath. The crystals that formed were collected, washed with ethanol/water followed by a wash with water. Drying gave 1.28 g (49%) of the title compound, as white crystals (m.p. 110.0°-111.0° C.). Anal. Calc'd for $C_{15}H_{16}F_5N_5O_2$: C,45.81; H,4.10; N,17.80. Found: C,46.22; H,4.13; N,17.92.

EXAMPLE 90

3-Pyridinecarboxylic acid, 6-(difluoromethyl)-5-(4,5-dihydro-5-oxo-1,3,4-oxadiazol-2-yl)-4-(2-methylpropyl)-2-(trifluoromethyl)-, methyl ester A solution of 10.0 g (0.027 mole) of 3.5-pyridinedicarboxylic acid, 2-(difluoromethyl)-4-(2-methylpropyl)-6-(trifluoromethyl)-, 3-hydrazide 5-methyl ester in 180 mL of chlorobenzene was brought to reflux. Phosgene was bubbled into the reaction mixture for one hour while the reaction was monitored by GLC. The mixture was allowed to cool and then was concentrated in vacuo to give an oil which crystallized on standing. Recrystallized product from methylene chloride-hexanes to give 6.5 g (60%) of the title compound as a white solid (MP 106°-108° C.). Anal. Calc'd for $C_{15}H_{14}F_5N_3O_4$: C,45.57; H,3.58; N,10.63. Found: C,45.66; H,3.62; N,10.63.

EXAMPLE 91

3-Pyridinecarboxylic acid, 2-(difluoromethyl)-5-(4,5-dihydro-2-thiazolyl)-4-(2-methylpropyl)-6-(trifluoromethyl)-, 2-propenyl ester A solution of 2.0 q (0.005 mole) of 3-pyridinecarbonyl chloride, 2-(difluoromethyl)-5-(4,5-dihydro-2-thiazolyl)-4-(2-methylpropyl)-6-(trifluoromethyl)-, in 40 mL of toluene and 0.67 mL (0.01 mole) of allyl alcohol was heated at reflux overnight. The solution was then cooled, then poured into water, and extracted with ethyl ether. The organics were dried over MgSO$_4$, filtered, and concentrated to give 1.2 g of crude product. Purification on the chromatotron using 15% ethyl acetate in cyclohexane afforded 0.85 g (40%) of the title compound, as an oil (b.p. 135° C.;0.2mm; n$_D^{25}$ 1.5693). Anal. Calc'd for $C_{18}H_{19}F_5N_2O_2S_1$: C,51.18; H,4.53; N,6.63. Found: C,51.36; H,4.56; N,6.62.

EXAMPLE 92

3-Pyridinecarboxylic acid, 2-(difluoromethyl)-4-(2-methylpropyl)-5-i5-oxazolyl)-6-(trifluoromethyl)- methyl ester A mixture of 3.4 g (0.10 mole) of 3-pyridinecarboxylic acid. 2-(difluoromethyl)-4-(2-methylpropyl)-5-formyl-6-(trifluoromethyl)-, methyl ester, 1.95 g (0.10 mole) of tosylmethyl isocyanide, and 1.4 g (0.10 mole) of potassium carbonate in 50 mL of methanol was refluxed for three hours under nitrogen. Concentrated reaction mixture in vacuo and took residue up into ethyl acetate followed by washing with water then with brine. Dried over anhydrous magnesium sulfate and concentrated in vacuo to give and oil which was purified by silica gel chromatography (ethyl acetate:hexanes=1:4). Resulting oil was Kugelrohr distilled (120° C., 0.4 mm) to give 2.4 g (63%) of the title compound ($n_D^{25}$=1.4754). Anal. Calcd for $C_{16}H_{15}F_5N_2O_3$: C,50.80; H,4.00; N,7.41. Found: C,50.70; H,4.04; N,7.33.

EXAMPLE 93

3-Pyridinecarboxylic acid, 6-(difluoromethyl)-5-(1,3-dioxan-2-yl)-4-(2-methylpropyl)-2-(trifluoromethyl)-, methyl ester A mixture of 2.0q (0.0059 mole) of 3-pyridinecarboxylic acid, 6-(difluoromethyl)-4-(2-methylpropyl)-5-formyl-2-(trifluoromethyl)-, methyl ester, 2.6 g (0.0118 mol) of 1,3-(bistrimethylsilyloxy)propane, and 20 mg. of trimethylsilyl trifluoromethanesulfonate were stirred under nitrogen for two hours. Reaction was quenched by the addition of 0.2 mL of pyridine. The resulting mixture was passed through a plug of silica gel (ethyl acetate:hexanes=1:5) to remove excess reagents. The resulting oil was purified by silica gel chromatography on a chromatotron (ethyl acetate:hexanes=1:5) to give a colorless oil which was Kugelrohr distilled (140° C. @0.15 mm) to give 1.00 g (43%) of the title compound which crystallized on standing (MP 79°–81° C.). Anal. Calc'd for $C_{17}H_{20}F_5N_1O_4$: C,51.39; H,5.07; N,3.53. Found: C,51.31:.H,5.09; N,3.51.

EXAMPLE 94

3-Pyridinecarboxylic acid, 2-(difluoromethyl)-4-(2-methylpropyl)-5-(1,3-oxathiolan-2-yl)-6-(trifluoromethyl)-, methyl ester A flame dried flask was charged with 2.0 g (0.0059 mol) of 3-pyridinecarboxylic acid, 2-(difluoromethyl)-5-formyl-4-(2-methylpropyl)-6-(trifluoromethyl)-, methyl ester, 15 mL of dichloromethane, and 0.55 g (0.0071 mol) of 2-mercaptoethanol and placed in an ice/methanol bath. Added 0.15 mL of titanium tetrachloride and the solution was stirred at low temperature for for 30 minutes then at RT overnight. The solution was poured into water and extracted with ethyl ether. The organics were dried over MgSO4, filtered, and concentrated to give 2.3 g of crude oil. Kugelrohr distillation afforded 0.55 g (23%) of the title compound, as a clear colorless oil (b.p.132° C.;0.40 mm, $n_D^{25}$ 1.4915). Anal. Calc'd for $C_{16}H_{18}F_5N_1O_3S_1$ C,48.12; H,4.54; N,3.50. Found: C,48.14; H,4.57: N,3.49.

EXAMPLE 95

3-Pyridinecarboxylic acid, 2-(difluoromethyl)-5-(1,3-dioxolan-2-yl)-4-(2-methylpropyl)-6-(trifluoromethyl)-, methyl ester To a stirred anhydrous dichloromethane solution (1.5 mL) containing 19.5 mg of trimethylsilyl trifluoromethanesulfonate was added 4.3 mL (0.018 mol) of 1,2- bis(-trimethylsiloxyethane) and 3.0 g (0.0088 mol) of 3-pyridinecarboxylic acid, 2-(difluoromethyl)-5-formyl-4-(2-methylpropyl)-6-(trifluoromethyl)-, methyl ester at −78° C. The solution was stirred at −78° C. for 15 minutes, then at −20° C. for 30 minutes, and finally the reaction was stirred at 5° C. for 2 hours. Added 0.3 mL of anhydrous pyridine. The solution was poured into saturated NaHCO3 and extracted with ethyl ether. The ether extracts were dried over a combination of sodium carbonate and sodium sulfate. Filtration, concentration, and purification using a chromatograph (7:1 hexanes to ethyl acetate) afforded 0.89 g (26%) of the title compound, as a white solid (m.p. 56°–57° C.). Anal. Calc'd for $C_{16}H_{18}F_5N_1O_4$: C.50.13; H,4.73; N,3.65. Found: C,50.21; H,4.83; N,3.59.

EXAMPLE 96

3-Pyridinecarboxylic acid, 2-(dichloromethyl)-5-(4,5-dihydro-2-thiazolyl)-4-(2-methylpropyl)-6-(trifluoromethyl)-, methyl ester 3-Pyridinecarboxylic acid, 2-(difluoromethyl)-5-(4,5-dihydro-2-thiazolyl)-4-(2-methylpropyl)-6- (trifluoromethyl)-, methyl ester (5.38 g,0.0136 mol), 60 mL of methylene chloride and 6.39 g of aluminum chloride were combined under a nitrogen atmosphere at 10° C. After five minutes the ice bath was removed, and the reaction was allowed to warm to room temperature. The reaction gradually darkened in color over 30 minutes after which time $^{19}$FNMR indicated completion. The mixture was poured into ice/water followed by extraction with methylene chloride. The extracts were dried over anhydrous magnesium sulfate and concentrated in vacuo. The residue was purified by silica gel chromatography (methylene chloride/cyclohexane=1:1) followed by recrystallization from hexanes. The pure product was combined with product from a previous experiment to give 4.1 g (48%) of the title compound as a white solid (MP 119°–120° C.).

EXAMPLE 97

3-Pyridinecarboxylic Acid, 2-(chlorodifluoromethyl)-5-(4,5-dihydro-2-thiazolyl)-6-(1-methylethyl)-4-(2-methylpropyl)-, Methyl Ester Through a solution of 240 g of t-butyl isobutyrylacetate in 500 ml of methanol was passed 70 g of ammonia in 2 hours, maintaining the temperature at below 25° C. The resulting solution was sitrred at room temperature for 18 hours, after which the methanol was removed in vacuo. Methylene chloride was added and the suspension was filtered. The filtrate was concentrated on a rotary evaporator to give 180 g t-butyl 3-amino-4-methyl-2-pentenoate as an oil.

A solution of 18.6 g (0.1 mol) of methyl chlorodifluoroacetoacetate, 8.4 g (0.1 mol) of isovaleraldehyde and 20.5 g (0.1 mol) of t-butyl 3-amino-4-methyl-2-penenoate in 80 ml of THF containing 1 ml of piperidine was refluxed for 18 hours. Then the solution was concentrated in vacuo to give 46 g of crude tetrahydropyridine as an oil.

To a solution of 27 g of the crude tetrahydropyridine and 20 ml of DBU in 80 ml of methylene chloride was added dropwise 9 ml of trifluoroacetic anhydride at below 12° C. and the resulting solution was stirred at room temperature for 18 hours. Water was added and the two layers were separated. The organic layer was washed with 2N HCl, water and brine, then dried and concentrated to give 22 g of crude dihydropyridine as an oil.

To a solution of 22 g of the crude dihydropyridine in 120 ml of methylene chloride was added in portions 12 g of 2,3-dichloro-5,6-dicyano-1,4-benzoquinone keeping the reaction temperature at 20°–30° C. and then stirred at room temperature for 3 hours, after which the suspension was filtered and the cake was washed thoroughly with methylene chloride. The filtrate was washed with saturated sodium bicarbonate solution and the brine then dried and concentrated. Column chromatography on silica gel (2% ethylacetatecyclohexane) gave 7.8 g of crude pyridinedicarboxylate as an oil.

To a solution of acid chloride (prepared from 11 g of pyridinedicarboxylate) in 50 ml of $CH_2Cl_2$ was added dropwise a solution of 7 g of 2-aminoethanol in 50 ml $CH_2Cl_2$ at below 10° C. and the solution was then sitrred at room temperature for 18 hours. 2N HCl was added and the organic layer was separated, washed with $H_2O$, brine, dried and concentrated. Column chromatography on silica gel (35% ethylacetatecyclohexane) gave 4.4 g of 3-pyridinecarboxylic acid, 2-(chlorodifluoromethyl)-5-([[(2-hydroxyethyl)aminocarbonyl] -6-(1-methylethyl)-4-(2-methylpropyl)-, methyl ester as a white solid. m.p. 114°–120° C.

A mixture of 4 g (10 mmol) of N-(2-hydroxyethyl) amide and 2.2 g of phosphorus pentasulfide in 100 ml of xylene was heated under reflux for 18 hours. Ether and saturated sodium bicarbonate solution were added. The organic layer was separated, washed with water, and then brine, dried and concentrated. Column chromatography on silica gel (6% ethylacetatecyclohexane) gave 1.4 g (32%) of brownish colored solid. m.p. 107°–111° C.

EXAMPLE 98

3-Pyridinecarboxylic acid, 2-(difluoromethyl)-5-(4,5-dihydro-2-thiazolyl)-6-(1-methylethyl)-4-(2-methylpropyl)-, methyl ester A solution of 17 g (40 mmol) of the crude pyridinedicarboxylate prepared as in Example 97 and 7 ml of tri-ethylamine in 160 ml of ethanol was hydrogenolyzed at ambient temperature and 2 atmospheres of hydrogen pressure in the presence of 3 g of 5% pallalium on charcoal for 18 hours The suspension was filtered through celite and concentrated. Water and $CH_2Cl_2$ were added and the phases were separated. The $CH_2Cl_2$ layer was washed with water, dried, and concentrated. Flash chromatography on silica gel (2% ethyl acetate/cyclohexane gave 14 g (91%) of 3,5-pyridinedicarboxylic acid, 2-(difluoromethyl)-6-(1-methylethyl)-4-(2-methylpropyl), 5-(1,1-dimethylethyl) 3-methyl ester as a colorless oil, $n_D^{25} = 1.4713$.

A solution of 5.4 g (14 mmol) of this material in 25 ml of trifluoroacetic acid was stirred at room temperature for 18 hours, after which the trifluoroacetic acid was removed. Water and $CH_2Cl_2$ were added, and the phases were separated. The organic layer was washed with water and then brine, then dried and concentrated. The resulting monoacid in 30 ml of oxalyl chloride containing 3 drops of DMF was heated at reflux for 6 hours, then the excess oxalyl chloride was removed in vacuo, giving the crude monoacid chloride.

The crude acid chloride in 30 ml of $CH_2Cl_2$ (9.4 g, 27 mmol) was added to a solution of 12 g of 2-aminoethanol and 4 mL of triethylamine in 50 ml of $CH_2Cl_2$ at 0° C. The solution was stirred at room temperature for 2 hours. Water was added, then the organic layer was separated, washed with water and then brine, dried, and concentrated. Flash chromatography on silica gel (50% ethyl acetate/cyclohexane) gave 7 g (70%) of white solid (the 5-(2-hydroxyethyl) amide), m.p. 108°–112° C.

A reaction mixture of 4 g (11 mmol) of the N-2-hydroxyethylamide and 2.6 g of phosphorous pentasulfide in 6.0 ml of xylene was heated under reflux for 18 hours. Ether and saturated $NaHCO_3$ solution were added. The organic layer was separated, washed with water, brine, dried and concentrated. Flash chromatography on silica gel 6% ethylacetatecyclohexane gave 0.4 (10%) of brown solid. m.p. 80°–86° C.

TABLE 2

| Example No. | Compound | M.P./B.P. | $n_D^{25}$ |
|---|---|---|---|
| 99 | 3-Pyridinecarboxamide, 2-(difluoromethyl)-5-(4,5-dihydro-2-thiazolyl)-4-(2-methylpropyl)-6-(trifluoromethyl)- | 183–185° C. | |
| 100 | 3-Pyridinecarboxamide, 2-(difluoromethyl)-5-(4,5-dihydro-2-thiazolyl)-N,N-dimethyl-4-(2-methylpropyl)-6-(trifluoromethyl)- | 111–114° C. | |
| 101 | Pyridine, 2-(difluoromethyl)-5-(4,5-dihydro-2-thiazolyl)-4-(2-methylpropyl)-3-(1-methyl)-1H-tetrazol-5-yl)-6-(trifluoromethyl)- | 152–154° C. | |
| 102 | 3-Pyridinecarboxylic acid, 6-(difluoromethyl)-4-(2-methylpropyl)-5-(5-oxazolyl)-2-(trifluoromethyl)-, methyl ester | | 1.4778 |
| 103 | 3-Pyridinecarboxylic acid, 2-(difluoromethyl)-5-(4,5-dihydro-2-thiazolyl)-4-(2-methylpropyl)-6-(trifluoromethyl)-, 2-propynyl ester | 120° C. @ 0.2 mm | 1.5025 |
| 104 | 3-Pyridinecarboxylic acid, 2-(difluoromethyl)-5-(4,5-dihydro-2-thiazolyl)-4-(2-methylpropyl)-6-(trifluoromethyl)-, 2-(2-methoxyethoxy) ethyl ester | 145° C. @ 0.2 mm | 1.4935 |
| 105 | 3-Pyridinecarbothioic acid, 6-(difluoromethyl)-5-[5-(1-methylethyl)-1,3,4-oxadiazol-2-yl]-4-(2-methylpropyl)-2-(trifluoromethyl)-2, S-methyl | 62–63° C. | |

TABLE 2-continued

| Example No. | Compound | M.P./B.P. | $n_D^{25}$ |
|---|---|---|---|
| 106 | 3-Pyridinecarbothioic acid, 6-(difluoromethyl)-5-(5-ethyl-1,3,4-oxadiazol-2-yl)-4-(2-methylpropyl)-2-(trifluoromethyl)-, S-methyl ester | 145° C. @ 0.35 mm | 1.4996 |
| 107 | 3-Pyridinecarboxylic acid, 2-(difluoromethyl)-4-(2-methylpropyl)-5-(1-methyl-1H-tetrazol-5-yl)-6-(trifluoro-methyl)-, methyl ester | 110–111° C. | |
| 108 | 3-Pyridinecarboxylic acid, 6-(fluoromethyl)-5-(4,5-dihydro-2-thiazolyl)-4-(2-methylpropyl)-2-(trifluoromethyl)-, methyl ester | 63–64° C. | |
| 109 | 3-Pyridinecarboxylic acid, 2-(difluoromethyl)-5-(1,3-dioxan-2-yl)-4-(2-methylpropyl)-6-(trifluoromethyl)-, methyl ester | | 1.4612 |
| 110 | 3-Pyridinecarboxylic acid, 2-(difluoromethyl)-5-(4,5-dihydro-2-thiazolyl)-4-(2-methylpropyl)-6-(trifluoromethyl)-, 2-fluoroethyl ester | | 1.4919 |
| 111 | 3-Pyridinecarboxylic acid, 6-(difluoromethyl)-4-(2-methylpropyl)-5-(1,3-oxathiolan-2-yl)-2-(trifluoromethyl)-, methyl ester | 129–130° C. | |
| 112 | 3-Pyridinecarboxylic acid, 6-(difluoromethyl)-5-(1,3-dioxalan-2-yl)-4-(2-methylpropyl)-2-(trifluoromethyl)-, methyl ester | 119–120° C. | |

PRE-EMERGENT HERBICIDE EXAMPLES

As noted above, compounds of this invention have been found to be effective as herbicides, particularly pre-emergent herbicides. Tables A and B summarize results of tests conducted to determine the pre-emergent herbicidal activity of the compounds of this invention. The herbicidal ratings used in Tables A and B were assigned according to a scale based on the percent inhibition of each plant species. The herbicide rating symbols in Tables A and B are defined as follows:

| % Inhibition | Rating |
|---|---|
| 0–24 | 0 |
| 25–49 | 1 |
| 50–74 | 2 |
| 75–100 | 3 |
| Not planted | — or a blank |

Species planted, no data N Where necessary, footnotes are shown at the end of the table.

For some compounds of this invention data were originally recorded as percent inhibition (or control) in ten percent increments. Where this system was used, the percentages have been mathematically converted to the above equivalent system using the correlation table above.

PRE-EMERGENT ACTIVITY ON WEEDS

One set of pre-emergent tests was conducted as follows:

Topsoil was placed in a pan and compacted to a depth of 0.95 to 1.27 cm. from the top of the pan. A predetermined number of seeds of each of several monocotyledonous and dicotyledonous annual plant species and/or vegetative propagules of various perennial plant species were placed on top of the soil. The soil required to level fill a pan after seeding or adding vegetative propagules was weighed into another pan. A known amount of the test compound dissolved or suspended in an organic solvent or water and applied in acetone or water as a carrier was thoroughly mixed with this cover soil, and the herbicide/soil mixture was used as a cover layer for the previously prepared pan. In Table A below the amount of active ingredient was eqivalent to an application rate of 11.2 kg/ha. After treatment, the pans were moved to a greenhouse bench where they were watered as needed to give adequate moisture for germination and growth.

Approximately 10–14 days (usually 11 days) after planting and treating, the pans were observed and the results recorded. In some instances, a second observation was made approximately 24–28 days after seeding and treating, and these observations are indicated in the following tables by a "pound" sign (#) immediately following the Example number.

The plant species usually regarded as weeds which were utilized in one set of pre-emergent activity tests, the data for which are shown in Table A, are identified by letter headings printed diagonally above the columns according to the following legend:

CATH—Canada thistle*
RHQG—Quackgrass*
COBU—Cocklebur
RHJG—Rhizome Johnsongrass*
VELE—Velvetleaf
DOBR—Downy Brome
MOGL—Morningglory
BYGR—Barnyardgrass
COLQ—Common Lambsquarters
ANBG—Annual Bluegrass
PESW—Pennsylvania Smartweed
SEJG—Seedling Johnsongrass
YENS—Yellow Nutsedge*
INMU—Indian Mustard
WIBW—Wild Buckwheat
* Grown from vegetative propagules In Table A, the first column is the application rate of the compound being tested in kg/ha.

TABLE A

| Ex. No. | Rate kg/ha | Yens | Anbg | Sejg | Dobr | Bygr | Mogl | Cobu | Vele | Inmu | Wibw | Cath | Colq | Pesw | Rhqg | Rhjg |
|---|---|---|---|---|---|---|---|---|---|---|---|---|---|---|---|---|
| 1 | 11.2100 | 1 | | | 0 | 3 | 2 | 0 | 2 | | | 1 | 3 | 2 | 1 | N |
| 2 | 11.2100 | 3 | | | 3 | 3 | 3 | 2 | 3 | | | 3 | 3 | 3 | 3 | 0 |
| 3 | 11.2100 | 3 | | | 3 | 3 | 3 | 3 | 3 | | | 3 | 3 | 3 | 3 | 3 |

TABLE A-continued

| Ex. No. | Rate kg/ha | Yens | Anbg | Sejg | Dobr | Bygr | Mogl | Cobu | Vele | Inmu | Wibw | Cath | Colq | Pesw | Rhqg | Rhjg |
|---|---|---|---|---|---|---|---|---|---|---|---|---|---|---|---|---|
| 4 | 11.2100 | 1 | | | 3 | 3 | 3 | 0 | 3 | | | 1 | 3 | 3 | 2 | 0 |
| 5 | 11.2100 | 2 | | | 3 | 3 | 3 | 2 | 3 | | | 3 | 3 | 3 | 3 | 3 |
| 6 | 11.2100 | 3 | | | 3 | 3 | 3 | 2 | 3 | | | 3 | 3 | 3 | 3 | 0 |
| 7 | 11.2100 | 3 | | | 3 | 3 | 3 | 1 | 3 | | | 1 | 3 | 3 | 3 | 0 |
| 8 | 11.2100 | 1 | | | — | 3 | 2 | 0 | 1 | | | 3 | 3 | 2 | 3 | 0 |
| 9 | 11.2100 | 3 | | | — | 3 | 3 | 2 | 3 | | | 3 | 3 | 3 | 3 | 3 |
| 10 | 11.2100 | 3 | | | 3 | 3 | 3 | 3 | 3 | | | 3 | 3 | 3 | 3 | 3 |
| 11 | 11.2100 | 1 | | | 3 | 3 | 3 | 1 | 3 | | | 3 | 3 | 3 | 3 | 3 |
| 12 | 11.2100 | 0 | | | 1 | 3 | 0 | 0 | 0 | | | 0 | 3 | 3 | 0 | 0 |
| 13 | 11.2100 | 1 | | | 2 | 3 | 2 | 0 | 0 | | | 0 | 3 | 3 | 3 | 3 |
| 14 | 11.2100 | 2 | | | 3 | 3 | 1 | 0 | 3 | | | 0 | 3 | 3 | 2 | 0 |
| 15 | 11.2100 | 1 | | | 3 | 3 | 3 | 3 | 3 | | | 3 | 3 | 3 | 3 | 3 |
| 16 | 11.2100 | 0 | | | 1 | 3 | 0 | 0 | 0 | | | 0 | 2 | 1 | 0 | 0 |
| 17 | 11.2100 | 3 | | | 3 | 3 | 3 | 3 | 3 | | | 3 | 3 | 3 | 3 | 3 |
| 18 | 11.2100 | 3 | | | 3 | 3 | 3 | 3 | 3 | | | 3 | 3 | 3 | 3 | 3 |
| 19 | 11.2100 | 3 | | | 3 | 3 | 3 | 2 | 3 | | | 3 | 3 | 3 | 3 | 3 |
| 20 | 11.2100 | 0 | | | 3 | 3 | 3 | 0 | 3 | | | 3 | 3 | 3 | 3 | 0 |
| 21 | 11.2100 | 3 | | | 3 | 3 | 3 | 2 | 2 | 3 | | 0 | 3 | 3 | 3 | 3 |
| 22 | 11.2100 | 2 | | | 3 | 3 | 3 | 0 | 3 | | | 2 | 3 | 3 | 3 | 0 |
| 23 | 11.2100 | 2 | | | 3 | 3 | 3 | 1 | 3 | | | 0 | 3 | 3 | 3 | 0 |
| 24 | 11.2100 | 0 | | | 3 | 3 | 0 | 0 | 0 | | | 0 | 3 | 2 | 3 | 0 |
| 25 | 11.2100 | 0 | | | 1 | 3 | 1 | 0 | 2 | | | 3 | 3 | 3 | 3 | 1 |
| 26 | 11.2100 | 1 | | | 3 | 3 | 3 | 0 | 3 | | | 0 | 3 | 3 | 1 | 0 |
| 27 | 11.2100 | 3 | | | 3 | 3 | 3 | 2 | 3 | | | — | 3 | 3 | 3 | 3 |
| 28 | 11.2100 | 3 | | | 3 | 3 | 3 | 3 | 3 | | | 3 | 3 | 3 | 3 | 3 |
| 29 | 11.2100 | 1 | | | 3 | 3 | 3 | 0 | 3 | | | 3 | 3 | 3 | 3 | 0 |
| 30 | 11.2100 | 2 | | | 3 | 3 | 3 | 1 | 3 | | | 3 | 3 | 3 | 3 | 0 |
| 31 | 11.2100 | 2 | | | 3 | 3 | 3 | 0 | 3 | | | 3 | 3 | 3 | 3 | 0 |
| 32 | 11.2100 | 3 | | | 3 | 3 | 3 | 1 | 3 | | | 3 | 3 | 3 | 3 | 2 |
| 33 | 11.2100 | 1 | | | 3 | 3 | 3 | 0 | 3 | | | 1 | 3 | 3 | 3 | 1 |
| 34 | 11.2100 | 3 | | | 3 | 3 | 3 | 3 | 3 | | | 3 | 3 | 3 | 3 | 3 |
| 35 | 11.2100 | 2 | | | 3 | 3 | 3 | 2 | 3 | | | 3 | 3 | 3 | 3 | 3 |
| 36 | 11.2100 | 3 | | | 3 | 3 | 3 | 3 | 3 | | | 3 | 3 | 3 | 3 | 3 |
| 37 | 11.2100 | 2 | | | 3 | 3 | 3 | 2 | 3 | | | 3 | 3 | 3 | 3 | 3 |
| 38 | 11.2100 | 3 | | | 3 | 3 | 3 | 2 | 3 | | | 3 | 3 | 3 | 3 | 0 |
| 39 | 11.2100 | 0 | | | 3 | 3 | 3 | 0 | 3 | | | 0 | 3 | 3 | 2 | 0 |
| 40 | 11.2100 | 1 | | | 3 | 3 | 3 | 2 | 3 | | | 1 | 3 | 3 | 3 | 3 |
| 41 | 11.2100 | 3 | | | 3 | 3 | 3 | 3 | 3 | | | 3 | 3 | 3 | 3 | 3 |
| 42 | 11.2100 | 0 | | | 3 | 3 | 3 | 1 | 3 | | | 3 | 3 | 3 | 3 | 0 |
| 43 | 11.2100 | 2 | | | 3 | 3 | 3 | 2 | 3 | | | 3 | 3 | 3 | 3 | 2 |
| 44 | 11.2100 | 3 | | | 3 | 3 | 3 | 3 | 3 | | | 3 | 3 | 3 | 3 | 3 |
| 45 | 11.2100 | 1 | | | — | 3 | 3 | 3 | 3 | | | 1 | 3 | 3 | 3 | 0 |
| 46 | 11.2100 | 3 | | | — | 3 | 3 | 1 | 3 | | | 3 | 3 | 3 | 3 | 3 |
| 47 | 11.2100 | 3 | | | 3 | 3 | 3 | 1 | 1 | | | 3 | 3 | 3 | 3 | 0 |
| 48 | 11.2100 | 3 | | | 3 | 3 | 3 | 0 | 3 | | | 3 | 3 | 3 | 3 | 3 |
| 49 | 11.2100 | 2 | | | 3 | 3 | 3 | 0 | 2 | | | 0 | 3 | 3 | 3 | 3 |
| 50 | 11.2100 | 1 | | | 1 | 3 | 3 | 0 | 3 | | | 2 | 3 | 3 | 2 | 0 |
| 51 | 11.2100 | 2 | | | 3 | 3 | 3 | 0 | 2 | | | 3 | 3 | 3 | 3 | 3 |
| 52 | 11.2100 | 3 | | | 3 | 3 | 3 | 0 | 3 | | | 3 | 3 | 3 | 3 | 3 |
| 53 | 11.2100 | 0 | | | 0 | 3 | 0 | 0 | 0 | | | 3 | 3 | 1 | 0 | 0 |
| 54 | 11.2100 | 0 | | | 1 | 3 | 3 | 0 | 3 | | | 0 | 3 | 2 | 0 | 3 |
| 55 | 11.2100 | 3 | | | 3 | 3 | 3 | 2 | 3 | | | 0 | 3 | 3 | 3 | 0 |
| 56 | 11.2100 | 1 | | | 3 | 3 | 3 | 0 | 1 | | | 0 | 3 | 3 | 3 | 3 |
| 57 | 11.2100 | 3 | | | 3 | 3 | 3 | 3 | 3 | | | 3 | 3 | 3 | 3 | 0 |
| 58 | 11.2100 | 3 | | | 3 | 3 | 3 | 0 | 3 | | | 0 | 3 | 3 | 3 | 3 |
| 59 | 11.2100 | 2 | | | 3 | 3 | 3 | 3 | 3 | | | 3 | 3 | 3 | 3 | 0 |
| 60 | 11.2100 | 3 | | | 3 | 3 | 3 | 1 | 3 | | | 3 | 3 | 3 | 3 | 3 |
| 61 | 11.2100 | 0 | | | 0 | 3 | 0 | 0 | 0 | | | 0 | 0 | 0 | 0 | 0 |
| 62 | 11.2100 | 1 | | | 2 | 3 | 3 | 1 | 2 | | | 0 | 3 | 3 | 3 | 0 |
| 63 | 11.2100 | 1 | | | 1 | 3 | 3 | 2 | 3 | | | 1 | 3 | 3 | 3 | 0 |
| 64 | 11.2100 | 0 | | | 3 | 3 | 3 | 3 | 3 | | | 3 | 3 | 3 | 3 | 0 |
| 65 | 11.2100 | 2 | | | 3 | 3 | 3 | 0 | 3 | | | 0 | 3 | 3 | 3 | 0 |
| 66 | 11.2100 | 3 | | | 3 | 3 | 3 | 3 | 3 | | | 2 | 3 | 3 | 3 | 0 |
| 67 | 11.2100 | 1 | | | 3 | 3 | 3 | 1 | 3 | | | 3 | 3 | 3 | 3 | 0 |
| 68 | 11.2100 | 0 | | | 2 | 3 | 2 | 0 | 1 | | | 0 | 3 | 3 | 2 | 0 |
| 69 | 11.2100 | 0 | | | 3 | 3 | 2 | 1 | 2 | | | 3 | 3 | 3 | 3 | 1 |
| 70 | 11.2100 | 1 | | | 3 | 3 | 3 | 2 | 3 | | | 3 | 3 | 3 | 3 | 0 |
| 71 | 11.2100 | 0 | | | 3 | 3 | 3 | 3 | 3 | | | 3 | 3 | 3 | 3 | 3 |
| 72 | 11.2100 | 3 | | | 3 | 3 | 3 | 2 | 3 | | | 3 | 3 | 3 | 3 | 3 |
| 73 | 11.2100 | 0 | | | 0 | 3 | 0 | 0 | 0 | | | 0 | 0 | 0 | 0 | 0 |
| 74 | 11.2100 | 0 | | | 0 | 0 | 0 | 0 | 0 | | | 0 | 1 | 0 | 0 | 0 |
| 75 | 11.2100 | 0 | | | 0 | 0 | 0 | 0 | 0 | | | 0 | 0 | 0 | 0 | 0 |
| 76 | 11.2100 | 0 | | | 0 | 0 | 0 | 0 | 0 | | | 0 | 3 | 0 | 0 | 0 |
| 77 | 11.2100 | 0 | | | 3 | 3 | 2 | 0 | 2 | | | 0 | 3 | 3 | 1 | 1 |
| 78 | 11.2100 | 2 | | | 3 | 3 | 3 | 0 | 3 | | | 3 | 3 | 3 | 3 | 3 |
| 79 | 11.2100 | 1 | | | 3 | 3 | 3 | 2 | 3 | | | 0 | 3 | 3 | 3 | 0 |
| 80 | 11.2100 | 3 | | | 3 | 3 | 3 | 0 | 3 | | | 3 | 3 | 3 | 3 | 3 |
| 81 | 11.2100 | 2 | | | 2 | 3 | 3 | 0 | 3 | | | 3 | 3 | 3 | 3 | 3 |
| 82 | 11.2100 | 3 | | | 3 | 3 | 3 | 3 | 3 | | | 3 | 3 | 3 | 3 | 0 |
| 83 | 11.2100 | 2 | | | 3 | 3 | 3 | 3 | 3 | | | 3 | 3 | 3 | 3 | 3 |
| 84 | 11.2100 | 2 | 3 | 3 | 3 | 3 | 3 | 0 | 2 | 3 | 3 | | | | | |

TABLE A-continued

| Ex. No. | Rate kg/ha | Yens | Anbg | Sejg | Dobr | Bygr | Mogl | Cobu | Vele | Inmu | Wibw | Cath | Colq | Pesw | Rhqg | Rhjg |
|---|---|---|---|---|---|---|---|---|---|---|---|---|---|---|---|---|
| 85 | 11.2100 | 0 | 2 | 0 | 0 | 3 | 0 | 0 | 0 | 0 | 0 | | | | | |
| 86 | 11.2100 | 0 | 3 | 3 | 2 | 3 | 0 | 0 | 2 | 2 | 1 | | | | | |
| 87 | 11.2100 | 1 | 3 | 3 | 3 | 3 | 3 | 0 | 3 | 3 | 3 | | | | | |
| 88* | 11.2100 | 0 | | | 2 | 3 | 3 | 0 | 2 | | | 0 | 3 | N | 0 | 0 |
| 89 | 11.2100 | 0 | | | 0 | 3 | 1 | 0 | 0 | | | 0 | 2 | N | 1 | 0 |
| 90 | 11.2100 | 0 | 0 | 0 | 0 | 0 | 0 | 0 | 0 | 0 | 0 | | | | | |
| 91 | 11.2100 | 1 | | | 1 | 3 | 3 | 2 | 3 | | | 3 | 3 | N | 1 | 0 |
| 92 | 11.2100 | 2 | 3 | 3 | 3 | 3 | 3 | 0 | 3 | 3 | 3 | | | | | |
| 93@ | 11.2100 | 2 | 3 | 3 | 3 | 3 | 3 | 2 | 3 | 3 | 3 | | | | | |
| 94 | 11.2100 | 3 | 3 | 3 | 3 | 3 | 3 | 2 | 3 | 3 | 3 | | | | | |
| 95 | 11.2100 | 3 | 3 | 3 | 3 | 3 | 3 | 3 | 3 | 3 | 3 | | | | | |
| 96@ | 11.2100 | 1 | 3 | 3 | 3 | 3 | 3 | 1 | 3 | 3 | 2 | | | | | |
| @ | 11.2100 | 1 | 3 | 3 | 3 | 3 | 3 | 1 | 3 | 3 | 2 | | | | | |
| 97 | 11.2100 | 0 | 3 | 3 | 3 | 3 | 1 | 1 | 1 | 3 | 3 | | | | | |
| 98 | 11.2100 | 2 | 3 | 3 | 3 | 3 | 3 | 2 | 3 | 3 | 3 | | | | | |
| 99 | 11.2100 | 0 | 3 | 2 | 2 | 3 | 0 | 0 | 0 | 1 | 0 | | | | | |
| 100 | 11.2100 | 0 | 3 | 3 | 0 | 3 | 1 | 0 | 1 | 2 | 2 | | | | | |
| 101 | 11.2100 | 0 | 3 | 0 | 0 | 3 | 1 | 1 | 2 | 1 | 2 | | | | | |
| 102 | 11.2100 | 1 | 3 | 3 | 3 | 3 | 3 | 3 | 3 | 3 | 3 | | | | | |
| 103 | 11.2100 | 2 | | | 3 | 3 | 3 | 1 | 3 | | | 3 | 3 | N | 3 | 0 |
| 104 | 11.2100 | 0 | | | 0 | 3 | 2 | 0 | 2 | | | 0 | 3 | N | 0 | 0 |
| 105 | 11.2100 | 0 | | | 0 | 3 | 0 | 0 | 0 | | | 0 | 1 | N | 0 | 0 |
| 106* | 11.2100 | 0 | | | 3 | 3 | 3 | 0 | 3 | | | 3 | 3 | N | 3 | 0 |
| 107 | 11.2100 | 0 | 2 | 3 | 3 | 3 | 1 | 0 | 1 | 1 | 1 | | | | | |
| 108 | 11.2100 | 2 | 3 | 3 | 3 | 3 | 3 | 0 | 3 | 3 | 3 | | | | | |
| 109@ | 11.2100 | 2 | 3 | 3 | 3 | 3 | 3 | 2 | 3 | 3 | 3 | | | | | |
| 110+ | 11.2100 | 2 | 3 | 3 | 3 | 3 | 3 | 3 | 3 | 3 | 3 | | | | | |
| 111 | 11.2100 | 0 | 3 | 3 | 2 | 3 | 3 | 0 | 3 | 3 | 3 | | | | | |
| 112 | 11.2100 | 1 | 3 | 3 | 3 | 3 | 3 | 0 | 3 | 3 | 2 | | | | | |

*POOR SMARTWEED GERMINATION
 NO TO POOR SMARTWEED GERMINATION.
@DAMPING OFF-IM,WB. POOR GERMINATION-WB.
+DAMPING OFF-IM,WB POOR GERMINATION-CB

PRE-EMERGENCE ACTIVITY ON WEEDS AND CROPS

In another set of tests, the pre-emergence activity of compounds of this invention was tested on weeds in the presence of crop plants. In these tests the following procedure was used:

Topsoil was sieved to pass through a ½ inch (1.27 cm) screen. Fertilizer was added to the topsoil in some of the tests, while in testing other compounds the fertilizer was omitted. The mixture was then sterilized by exposure to methyl bromide or by heating.

The topsoil mixture was placed in an aluminum pan and compacted to a depth of about 1.27 cm. from the top of the pan. A predetermined number of seeds of each of several monocotyledonous and dicotyledonous plant species and where noted vegetative propagules of various perennial plant species. The soil required to level fill a pan after seeding or adding vegetative propagules was weighed into another pan. A known amount of the test compound was dissolved or suspended in acetone or a suitable organic solvent as a 1% solution or suspension and applied to the cover soil using a sprayer at the desired rate. The spray was thoroughly mixed with this cover soil, and the herbicide/soil mixture was used as a cover layer for the previously prepared pan. Untreated soil was used as a cover layer for control pans. Alternatively, the pans may be covered with the soil layer and the spray solution uniformly applied to the soil surface. When this latter method was used, the statement "surface application" accompanies the test data. In Table B below the amount of active ingredient applied is shown in the Table. After treatment, the pans were moved to a greenhouse bench. Moisture was supplied to each pan as needed for germination and growth. Growth of each species was observed and corrective measures (greenhouse fumigation, insecticide treatment, and the like) were applied as needed Approximately 10–14 days (usually 11 days) after planting and treating, the pans were observed and the results recorded. In some instances, a second observation is made (usually 24–28 days after seeding and treating, although this time interval was at the discretion of the observer), and these observations are indicated in the following tables by a "pound" sign (#) immediately following the Example number.

The pre-emergence data for weeds in the presence of crop plants is shown in the following Table B. In these tests, the plants are identified according to the following column headings printed diagonally above each column, the first column being the rate of application of the test compound in kg/ha:

SOBE - Soybean
SUBE - Sugarbeet
WHEZ - Wheat
RICE - Rice
GRSO - Grain Sorghum
COBU - Cocklebur
WIBW - Wild Buckwheat
NOGL - Morningglory
HESE - Hemp Sesbania
COLQ - Common Lambsquarters
PESW - Pennsylvania Smartweed VELE - Velvetleaf
DOBR - Downy Brome
PRMI - Proso Millet
BYGR - Barnyardgrass
LACG - Large Crabgrass
GRFT - Green Foxtail
CORN - Corn
COTZ - Cotton
RAPE - Oilseed Rape
JIWE - Jimsonweed

TABLE B

| Ex. No. | Rate kg/ha | Sobe | Cotz | Rape | Cobu | Wtbw | Mogl | Hese | Jiwe | Vele | Whez | Rice | Grso | Corn | Dobr | Prmi | Bygr | Lacg | Grft | Sube | Colq | Pesw |
|---|---|---|---|---|---|---|---|---|---|---|---|---|---|---|---|---|---|---|---|---|---|---|
| 1 | 5.6050 | 1 | | | 0 | 0 | 2 | 0 | | 0 | 0 | 2 | 2 | 0 | 0 | 3 | 3 | 3 | 3 | 0 | 0 | 3 |
| | 1.1210 | 0 | | | N | 1 | 0 | 1 | | 0 | 0 | 0 | 0 | 0 | 0 | 0 | 0 | 0 | 0 | 0 | N | 1 |
| | 0.5605 | 0 | | | N | 0 | N | 0 | | 0 | 0 | 0 | 0 | 0 | 0 | 0 | 0 | 1 | 0 | 0 | N | 2 |
| | 0.2803 | 0 | | | 0 | 0 | 0 | 2 | | 0 | 0 | 0 | 0 | 0 | 0 | 0 | 0 | 0 | 0 | 0 | 0 | 2 |
| | 0.1401 | N | | | 0 | 0 | 0 | 0 | | 0 | 0 | 0 | 1 | 0 | 0 | 0 | 0 | 3 | 0 | 2 | 1 | 2 |
| | 0.0701 | 0 | | | 0 | 0 | 0 | 0 | | 0 | 0 | 0 | 0 | 0 | 0 | 0 | 0 | 0 | | 0 | 0 | 2 |
| 2 | 5.6050 | 2 | | | 0 | 3 | 3 | 3 | | 2 | 3 | 3 | 3 | 0 | 3 | 3 | 3 | 3 | | 3 | 3 | 3 |
| | 1.1210 | 0 | | | 0 | 0 | 1 | 0 | | 1 | 0 | 2 | 2 | 0 | 0 | 0 | 2 | 3 | | 0 | 3 | 3 |
| | 0.2803 | 0 | | | 0 | 0 | 0 | 0 | | 0 | 0 | 0 | 1 | 0 | 0 | 0 | 0 | 3 | | 0 | 3 | 3 |
| | 0.0561 | 0 | | | 0 | 0 | 0 | 0 | | 0 | 0 | 0 | 0 | 0 | 0 | 0 | 0 | 0 | | 0 | 2 | 2 |
| | 0.0112 | 0 | | | 0 | 0 | 0 | 0 | | 0 | 0 | 0 | 0 | 0 | 0 | 0 | 0 | 0 | | 0 | 0 | 0 |
| 3 | 5.6050 | 3 | | | 0 | 3 | 3 | 3 | | 3 | 3 | 3 | 3 | | 3 | 3 | 3 | 3 | | 3 | 3 | 3 |
| | 1.1210 | 3 | | | 2 | 0 | 0 | 3 | | 3 | 3 | 2 | 3 | | 3 | 3 | 3 | 3 | | 3 | 3 | 3 |
| | 0.2803 | 2 | | | 1 | 3 | 3 | 3 | | 2 | 2 | 2 | 3 | | 3 | 3 | 3 | 3 | | 3 | 3 | 3 |
| | 0.0112 | 0 | | | 0 | 2 | 2 | 2 | | 1 | 1 | 3 | 1 | | 0 | 2 | 0 | 2 | | 1 | 2 | 2 |
| | 0.0056 | 0 | | | 0 | 1 | 1 | 2 | | 1 | 0 | 0 | 0 | | 0 | 0 | 0 | 0 | | 0 | 0 | 0 |
| | 0.0011 | 0 | | | 0 | 0 | 0 | 0 | | 0 | 0 | 0 | 0 | | 0 | 0 | 0 | 0 | | 0 | 0 | 0 |
| 4 | 5.6050 | 3 | | | 0 | 3 | 2 | 2 | | 2 | 3 | 3 | 2 | | 3 | 3 | 3 | 3 | | 3 | 3 | 3 |
| | 1.1210 | 3 | | | 0 | 1 | 0 | 0 | | 0 | 0 | 0 | 0 | | 2 | 3 | 3 | 3 | | 3 | 3 | 3 |
| | 0.2803 | 0 | | | 0 | 0 | 0 | 0 | | 0 | 0 | 0 | 0 | | 0 | 0 | 0 | 2 | | 0 | 0 | 0 |
| | 0.0561 | 0 | | | 0 | 3 | 2 | 2 | | 2 | 3 | 3 | 3 | | 3 | 3 | 3 | 3 | | 3 | 3 | 3 |
| 5 | 5.6050 | 3 | | | 0 | 0 | 0 | 0 | | 0 | 0 | 0 | 0 | | 0 | 0 | 0 | 2 | | 0 | 0 | 0 |
| | 1.1210 | 3 | | | 0 | 3 | 3 | 3 | | 3 | 3 | 3 | 3 | | 3 | 3 | 3 | 3 | | 3 | 3 | 3 |
| | 0.2803 | 0 | | | 0 | 0 | 0 | 0 | | 0 | 0 | 0 | 0 | | 0 | 0 | 0 | 1 | | 0 | 0 | 0 |
| | 0.0561 | 0 | | | 0 | 3 | 3 | 3 | | 3 | 3 | 3 | 3 | | 3 | 3 | 3 | 3 | | 3 | 3 | 3 |
| | 0.0112 | 0 | | | 0 | 0 | 0 | 2 | | 2 | 1 | 0 | 2 | | 2 | 1 | 0 | 2 | | 2 | 2 | 2 |
| 6 | 5.6050 | 3 | | | 1 | 3 | 2 | 2 | | 3 | 3 | 0 | 3 | | 3 | 3 | 3 | 3 | | 3 | 3 | 3 |
| | 1.1210 | 2 | | | 0 | 0 | 0 | 0 | | 2 | 0 | 0 | 2 | | 0 | 0 | 0 | 2 | | 0 | 0 | 0 |
| | 0.5605 | 0 | | | 0 | 2 | 2 | 2 | | 2 | 2 | 2 | 2 | | 2 | 2 | 2 | 2 | | 2 | 2 | 2 |
| | 0.2803 | 0 | | | 0 | 1 | 0 | 0 | | 0 | 1 | 1 | 0 | | 0 | 1 | 0 | 2 | | 1 | 1 | 1 |
| | 0.1401 | 0 | | | 0 | N | 0 | 0 | | 0 | 0 | 0 | 0 | | 0 | 0 | 0 | 2 | | 2 | 1 | 0 |
| | 0.0701 | 0 | | | 0 | 0 | 0 | 0 | | 0 | 0 | 0 | 0 | | 0 | 0 | 0 | 0 | | 0 | 0 | 0 |
| | 0.0350 | 0 | | | 0 | 0 | 0 | 0 | | 0 | 0 | 0 | 0 | | 0 | 0 | 0 | 0 | | 0 | 0 | 0 |
| 7 | 5.6050 | 3 | | | 0 | 3 | 3 | 3 | | 3 | 3 | 3 | 3 | | 3 | 3 | 3 | 3 | | 3 | 3 | 3 |
| | 1.1210 | 0 | | | 0 | 0 | 2 | 2 | | 0 | 0 | 2 | 2 | | 2 | 3 | 3 | 3 | | 3 | 3 | 3 |
| | 0.5605 | 0 | | | 0 | 3 | 1 | 0 | | 0 | 0 | 1 | 0 | | 2 | 2 | 0 | 2 | | 2 | 2 | 3 |
| | 0.2803 | 0 | | | 0 | 0 | 0 | 0 | | 0 | 0 | 0 | 0 | | 2 | 2 | 0 | 2 | | 2 | 2 | 3 |
| | 0.1401 | 0 | | | 0 | 0 | 0 | 0 | | 0 | 0 | 0 | 0 | | 0 | 2 | 0 | 2 | | 1 | 1 | 1 |
| | 0.0701 | 0 | | | 0 | 0 | 0 | 0 | | 0 | 0 | 0 | 0 | | 0 | 0 | 0 | 0 | | N | 1 | 2 |
| | 0.0350 | 0 | | | 0 | 0 | 0 | 0 | | 0 | 0 | 0 | 0 | | 2 | 0 | 0 | 2 | | 2 | 2 | 1 |
| | 0.0175 | 0 | | | 1 | 0 | 0 | 0 | | 0 | 0 | 0 | 0 | | N | 0 | 0 | 1 | | N | N | 0 |
| 8* | 5.6050 | 2 | | | 0 | 0 | 0 | 0 | | 0 | 0 | 0 | 0 | 2 | 0 | 0 | 0 | 0 | 3 | 0 | 0 | 0 |
| | 1.1210 | 2 | | | 0 | 3 | 3 | 3 | | 3 | 3 | 2 | 3 | 0 | 3 | 3 | 3 | 3 | 3 | 3 | 3 | 3 |
| | 0.5605 | 0 | | | 0 | 3 | 3 | 3 | | 3 | 2 | 2 | 0 | 0 | 3 | 3 | 3 | 3 | 1 | 3 | 3 | 3 |
| 9 | | 0 | | | 0 | 3 | 3 | 3 | | 3 | 2 | 2 | 3 | 0 | 3 | 3 | 3 | 3 | 0 | 3 | 3 | 3 |
| | | 0 | | | 0 | 3 | 3 | 3 | | 3 | 2 | 2 | 3 | 0 | 3 | 3 | 3 | 3 | 0 | 3 | 3 | 3 |

TABLE B-continued

| Ex. No. | Rate kg/ha | Sobe | Cotz | Rape | Cobu | Wibw | Mogl | Hese | Jiwe | Vele | Whez | Rice | Grso | Corn | Dobr | Prmi | Bygr | Lacg | Grft | Sube | Colq | Pesw |
|---|---|---|---|---|---|---|---|---|---|---|---|---|---|---|---|---|---|---|---|---|---|---|
| | 0.2803 | 0 | | | 0 | 3 | 1 | 3 | | 3 | 2 | 1 | 3 | 1 | 1 | 3 | 3 | 3 | 3 | 3 | 3 | 3 |
| | 0.1401 | 0 | | | 0 | 0 | 1 | 2 | | 2 | 2 | 0 | 3 | 0 | 2 | 3 | 3 | 3 | 3 | 2 | 3 | 3 |
| | 0.0701 | 0 | | | 0 | 0 | 0 | 0 | | 1 | 0 | 0 | 1 | 1 | 1 | 3 | 3 | 3 | 3 | 1 | 3 | 2 |
| | 0.0350 | 0 | | | 0 | 0 | 0 | 0 | | 0 | 0 | 0 | 0 | 0 | 0 | 0 | 1 | 2 | 1 | 1 | 1 | 2 |
| | 0.0175 | 0 | | | 0 | 0 | 0 | 0 | | 0 | 0 | 0 | 0 | 0 | 2 | 0 | 0 | 0 | 0 | 0 | 0 | 0 |
| | 0.0087 | 0 | | | 0 | 0 | 0 | 0 | | 0 | 0 | 0 | 0 | 0 | 0 | 0 | 0 | 0 | 0 | 0 | 0 | 0 |
| 10 | 5.6050 | 3 | | | 1 | 3 | 3 | 3 | | 3 | 3 | 3 | 3 | 3 | 3 | 3 | 3 | 3 | 3 | 3 | 3 | 3 |
| | 1.1210 | 2 | | | 0 | 1 | 1 | 2 | | 3 | 3 | 3 | 3 | 0 | 3 | 3 | 3 | 3 | 3 | 3 | 3 | 3 |
| | 0.5605 | 2 | | | 0 | 1 | 1 | 3 | | 3 | 2 | 3 | 3 | 0 | 2 | 3 | 3 | 3 | 3 | 3 | 3 | 3 |
| | 0.2803 | 1 | | | 0 | 0 | 0 | 2 | | 2 | 1 | 2 | 2 | 0 | 2 | 3 | 3 | 3 | 3 | 3 | 3 | 3 |
| | 0.1401 | 0 | | | 0 | 0 | 0 | 3 | | 1 | 1 | 1 | 1 | 0 | 2 | 3 | 2 | 3 | 3 | 2 | 3 | 3 |
| | 0.0701 | 0 | | | 0 | 0 | 0 | 1 | | 1 | 0 | 1 | 1 | 0 | 2 | 2 | 2 | 3 | 2 | 1 | 1 | 1 |
| | 0.0350 | 0 | | | 0 | 0 | 0 | 0 | | 0 | 0 | 0 | 0 | 0 | 0 | 0 | 0 | 2 | 0 | 1 | 0 | 0 |
| | 0.0175 | 0 | | | 0 | 0 | 0 | 0 | | 0 | 0 | 0 | 0 | 0 | 0 | 0 | 0 | 0 | 0 | 0 | 0 | 0 |
| | 0.0087 | 0 | | | 0 | 0 | 0 | 0 | | 0 | 0 | 0 | 0 | 0 | 0 | 0 | 0 | 0 | 0 | 0 | 0 | 0 |
| | 0.0044 | 0 | | | 0 | 0 | 0 | 0 | | 0 | 0 | 0 | 0 | 0 | 0 | 0 | 0 | 0 | 0 | 0 | 0 | 0 |
| 11 | 5.6050 | 2 | | | 0 | 0 | 0 | 3 | | 2 | 2 | 3 | 3 | 0 | 3 | 3 | 3 | 3 | 3 | 3 | 3 | 3 |
| | 1.1210 | 1 | | | 0 | 0 | 0 | 2 | | 2 | 2 | 3 | 3 | 0 | 2 | 3 | 3 | 3 | 3 | 1 | 3 | 3 |
| | 0.5605 | 0 | | | 0 | 0 | 0 | 3 | | 2 | 2 | 3 | 2 | 0 | 2 | 3 | 3 | 3 | 2 | 1 | 3 | 3 |
| | 0.2803 | 0 | | | 0 | 0 | 0 | 2 | | 0 | 0 | 2 | 2 | 0 | 2 | 3 | 3 | 3 | 2 | 0 | 3 | 2 |
| | 0.1401 | 0 | | | 0 | 0 | 0 | 0 | | 0 | 0 | 0 | 0 | 0 | 0 | 0 | 0 | 0 | 0 | 0 | 0 | 1 |
| | 0.0701 | 0 | | | 0 | 0 | 0 | 0 | | 0 | 0 | 0 | 0 | 0 | 0 | 0 | 0 | 0 | 0 | 0 | 0 | 0 |
| | 0.0350 | 0 | | | 0 | 0 | 0 | 0 | | 0 | 0 | 0 | 0 | 0 | 0 | 0 | 0 | 0 | 0 | 0 | 0 | 0 |
| | 0.0175 | 0 | | | 0 | 0 | 0 | 0 | | 0 | 0 | 0 | 0 | 0 | 0 | 0 | 0 | 0 | 0 | 0 | 0 | 0 |
| | 0.0087 | 0 | | | 0 | 0 | 0 | 0 | | 0 | 0 | 0 | 0 | 0 | 0 | 0 | 0 | 0 | 0 | 0 | 0 | 0 |
| 12 | 5.6050 | 0 | | | 0 | 0 | 0 | 0 | | 0 | 0 | 0 | 0 | 0 | 3 | 3 | 3 | 3 | 3 | 3 | 3 | 3 |
| | 1.1210 | 0 | | | 0 | 0 | 0 | 0 | | 0 | 0 | 0 | 0 | 0 | 0 | 1 | 0 | 2 | 2 | 0 | 0 | 1 |
| | 0.5605 | 0 | | | 0 | 0 | 0 | 0 | | 0 | 0 | 0 | 0 | 0 | 1 | 1 | 1 | 1 | 0 | 0 | 0 | 0 |
| | 0.2803 | 0 | | | 0 | 0 | 0 | 0 | | 0 | 0 | 0 | 0 | 0 | 0 | 0 | 0 | 0 | 0 | 0 | 0 | 0 |
| 13 | 2.8025 | 0 | | | 0 | 0 | 0 | 0 | | 0 | 0 | 0 | 0 | 0 | 2 | 3 | 3 | 3 | 3 | 0 | 3 | 0 |
| | 1.1210 | 0 | | | 0 | 0 | 0 | 0 | | 0 | 0 | 0 | 0 | 0 | 0 | 1 | 0 | 1 | 2 | 0 | 0 | 0 |
| | 0.5605 | 0 | | | 0 | 0 | 0 | 0 | | 0 | 0 | 0 | 0 | 0 | 2 | 3 | 1 | 3 | 2 | 0 | 1 | 1 |
| | 0.2803 | 0 | | | 0 | 0 | 0 | 0 | | 0 | 0 | 0 | 0 | 0 | 0 | 0 | 0 | 0 | 0 | 0 | 0 | 0 |
| | 0.1401 | 0 | | | 0 | N | 0 | 0 | | 0 | 0 | 0 | 0 | 0 | 2 | 0 | 0 | 2 | 0 | 0 | 0 | 0 |
| | 0.0701 | 0 | | | 0 | 0 | 0 | 0 | | 0 | 0 | 0 | 0 | 0 | 0 | 0 | 0 | 0 | 0 | 0 | 0 | 0 |
| | 0.0350 | 0 | | | 0 | 0 | 0 | 0 | | 0 | 0 | 0 | 0 | 0 | 0 | 0 | 0 | 0 | 0 | N | 0 | 0 |
| | 0.0175 | 0 | | | 0 | 0 | 0 | 0 | | 0 | 0 | 0 | 0 | 0 | 0 | 0 | 0 | 0 | 0 | 0 | 0 | 0 |
| 14 | 1.1210 | 0 | | | 0 | 2 | 0 | 2 | | 3 | 0 | 0 | 3 | 0 | 2 | 3 | 3 | 3 | 3 | 3 | 3 | 3 |
| | 0.5605 | 0 | | | 0 | 1 | 1 | 1 | | 2 | 3 | 0 | 1 | 0 | 0 | 2 | 2 | 2 | 0 | 0 | 0 | 2 |
| | 0.2803 | 0 | | | 0 | 0 | 0 | 0 | | 0 | 0 | 0 | 0 | 0 | 1 | 0 | 0 | 0 | 0 | 0 | 0 | 0 |
| | 0.1401 | 0 | | | 0 | 0 | 0 | 0 | | 0 | 0 | 0 | 0 | 0 | 0 | 0 | 0 | 0 | 0 | 0 | 0 | 0 |
| | 0.0701 | 0 | | | 0 | 0 | 0 | 0 | | 0 | 0 | 0 | 0 | 0 | 0 | 0 | 0 | 0 | 0 | 0 | 0 | 0 |
| 15 | 5.6050 | 3 | | | 3 | 3 | 3 | 3 | | 3 | 3 | 3 | 3 | 3 | 3 | 3 | 3 | 3 | 3 | 3 | 3 | 3 |
| | 1.1210 | 3 | | | 0 | 3 | 2 | 3 | | 3 | 3 | 3 | 3 | 3 | 3 | 3 | 3 | 3 | 3 | 3 | 3 | 3 |
| | 0.5605 | 3 | | | 1 | 2 | 3 | 3 | | 3 | 3 | 2 | 3 | 2 | 1 | 3 | 3 | 3 | 3 | 3 | 3 | 3 |
| | 0.2803 | 0 | | | 0 | 2 | 2 | 3 | | 2 | 0 | 2 | 3 | 2 | 2 | 2 | 3 | 3 | 3 | 1 | 1 | 3 |
| | 0.1401 | 0 | | | 0 | 3 | 3 | 3 | | 2 | 0 | 2 | 3 | 1 | 1 | 2 | 3 | 3 | 3 | 1 | 1 | 3 |
| | 0.0701 | 0 | | | 0 | 0 | 2 | 1 | | 1 | 0 | 2 | 2 | 2 | 2 | 2 | 3 | 3 | 3 | 1 | 1 | 3 |
| | 0.0350 | 0 | | | 0 | 0 | 0 | 1 | | 0 | 0 | 2 | 1 | 2 | 1 | 2 | 3 | 3 | 3 | 1 | 1 | 3 |
| | 0.0175 | 0 | | | 0 | 0 | 0 | 1 | | 0 | 0 | 2 | 0 | 2 | 1 | 2 | 3 | 3 | 3 | 0 | 0 | 3 |

TABLE B-continued

| Ex. No. | Rate kg/ha | Sobe | Cotz | Rape | Cobu | Wibw | Mogl | Hese | Jiwe | Vele | Whez | Rice | Grso | Corn | Dobr | Prmi | Bygr | Lacg | Grft | Sube | Colq | Pesw |
|---|---|---|---|---|---|---|---|---|---|---|---|---|---|---|---|---|---|---|---|---|---|---|
| 16 | 0.0087 | 0 | | | 0 | 0 | 0 | 0 | | 0 | 0 | 0 | 0 | 0 | 0 | 0 | 0 | | | 0 | 0 | 1 |
| | 5.6050 | 1 | | | 0 | 0 | 2 | 0 | | 2 | 3 | 3 | 2 | 0 | 3 | 3 | 2 | 3 | 2 | 2 | 0 | 1 |
| | 1.1210 | 0 | | | 0 | 2 | 0 | 0 | | 0 | 0 | 0 | 1 | 0 | 2 | 1 | 0 | 3 | 3 | 0 | 0 | 0 |
| | 0.5605 | 0 | | | 0 | 0 | 1 | 0 | | 0 | 0 | 0 | 0 | 0 | 1 | 1 | 1 | 1 | 1 | 0 | 0 | 0 |
| | 0.2803 | 0 | | | 0 | 2 | 3 | 3 | | 0 | 0 | 0 | 3 | 0 | N | 0 | 2 | 0 | 0 | 0 | 3 | 2 |
| 17 | 5.6050 | 3 | | | 3 | 3 | 3 | 3 | | 3 | 3 | 3 | 3 | 3 | 3 | 3 | 3 | 3 | 3 | 3 | 3 | 3 |
| | 1.1210 | 3 | | | 0 | 3 | 3 | 3 | | 3 | 3 | 3 | 3 | 3 | 3 | 3 | 3 | 3 | 3 | 2 | 3 | 3 |
| | 0.5605 | 0 | | | 0 | 3 | 2 | 2 | | 3 | 1 | 3 | 3 | – | 2 | 3 | 3 | 3 | 3 | 2 | 3 | 3 |
| | 0.2803 | 0 | | | 0 | 3 | 3 | 1 | | 3 | 0 | 3 | 3 | 0 | 2 | 3 | 3 | 3 | 3 | 2 | 3 | 3 |
| | 0.1401 | 0 | | | 0 | 0 | 2 | 2 | | 2 | 0 | 2 | 2 | 1 | 2 | 3 | 3 | 3 | 3 | N | 2 | 3 |
| | 0.0701 | 0 | | | 0 | 0 | 0 | 1 | | 2 | 0 | 2 | 0 | 0 | 2 | 3 | 3 | 3 | 3 | 0 | 2 | 3 |
| | 0.0350 | 0 | | | 0 | 0 | 0 | 0 | | 0 | 0 | 2 | 0 | – | 0 | 3 | 3 | 3 | 3 | 0 | 3 | 3 |
| | 0.0175 | 0 | | | 0 | 0 | 0 | 0 | | 0 | 0 | 1 | 0 | 0 | 0 | 3 | 3 | 3 | 3 | Z | 3 | 3 |
| | 0.0087 | 0 | | | 0 | 0 | 0 | 0 | | 0 | 0 | 0 | 0 | 0 | 0 | 3 | 3 | 3 | 3 | O | Z | 0 |
| | 0.0044 | 0 | | | 0 | 0 | 0 | 0 | | 0 | 0 | 0 | 0 | 0 | 0 | 3 | 3 | 2 | 2 | O | Z | 0 |
| 17 | 5.6050 | 3 | | | 3 | 3 | 3 | 3 | | 3 | 3 | 3 | 3 | 0 | 3 | 3 | 3 | 3 | 2 | Z | Z | 3 |
| 18 | 1.1210 | 3 | | | 0 | 3 | 3 | 3 | | 3 | 3 | 3 | 3 | 0 | 3 | 3 | 3 | 3 | | Z | 3 | 3 |
| | 0.5605 | 1 | | | 0 | 3 | 3 | 3 | | 3 | 2 | 3 | 3 | | 3 | 3 | 3 | 3 | | 0 | 3 | 3 |
| | 0.2803 | 3 | | | 3 | 2 | 2 | 2 | | 2 | 2 | 2 | 2 | | 3 | 3 | 3 | 3 | | O | 3 | 3 |
| | 0.1401 | 2 | | | 0 | 2 | 3 | 2 | | 2 | 2 | 3 | 2 | | 3 | 3 | 3 | 3 | | Z | 3 | 3 |
| | 0.0561 | 0 | | | 0 | 3 | 3 | 3 | | 3 | 3 | 3 | 3 | | 3 | 3 | 3 | 3 | | 3 | 3 | 3 |
| | 0.0112 | 0 | | | 0 | 2 | 3 | 2 | | 2 | 2 | 3 | 2 | | 3 | 3 | 3 | 3 | | 3 | 3 | 3 |
| | 0.0056 | 0 | | | 0 | 0 | 0 | 0 | | 0 | 0 | 0 | 0 | | 0 | 0 | 0 | 0 | | 0 | 0 | 0 |
| | 0.0011 | 0 | | | 0 | 0 | 0 | 0 | | 0 | 0 | 0 | 0 | | 0 | 0 | 0 | 0 | | 0 | 0 | 0 |
| 19 | 5.6050 | 3 | | | 0 | 3 | 3 | 3 | | 3 | 3 | 3 | 3 | 3 | 3 | 3 | 3 | 3 | 3 | 3 | 3 | 3 |
| | 1.1210 | 2 | | | 0 | 3 | 3 | 3 | | 3 | 3 | 3 | 3 | 3 | 3 | 3 | 3 | 3 | 3 | 3 | 3 | 3 |
| | 0.5605 | 1 | | | 0 | 0 | 2 | 3 | | 0 | 0 | 3 | 3 | 0 | 3 | 3 | 3 | 3 | 0 | 3 | 3 | 3 |
| | 0.2803 | 0 | | | 0 | 3 | 0 | 3 | | 3 | 3 | 3 | 3 | 0 | 3 | 3 | 3 | 3 | 3 | 3 | 3 | 3 |
| | 0.1401 | 0 | | | 0 | 3 | 2 | 3 | | 3 | 3 | 3 | 3 | 0 | 3 | 3 | 3 | 3 | 3 | 3 | 3 | 3 |
| | 0.0701 | 0 | | | 0 | 0 | 1 | 1 | | 3 | 3 | 3 | 2 | 0 | 3 | 3 | 3 | 3 | 3 | 2 | 3 | 3 |
| | 0.0350 | 0 | | | 0 | 0 | 0 | 0 | | 0 | 0 | 0 | 0 | 0 | 0 | 0 | 0 | 0 | 0 | 0 | 0 | 0 |
| | 0.0175 | 0 | | | 0 | 0 | 0 | 0 | | 0 | 0 | 0 | 0 | 0 | 0 | 0 | 0 | 0 | 0 | 0 | 0 | 0 |
| | 0.0087 | 0 | | | 0 | 1 | 0 | 0 | | 0 | 0 | 0 | 0 | 0 | 1 | 0 | 0 | 0 | 0 | 0 | 0 | 0 |
| 20 | 5.6050 | 3 | | | 3 | 3 | 3 | 3 | | 3 | 3 | 3 | 3 | 3 | 3 | 3 | 3 | 3 | 3 | 3 | 3 | 3 |
| | 1.1210 | 0 | | | 0 | 3 | 3 | 0 | | 0 | 0 | 0 | 0 | 0 | 3 | 3 | 3 | 3 | 3 | 3 | 3 | 3 |
| | 0.5605 | 0 | | | 0 | 0 | 0 | 0 | | 0 | 0 | 0 | 0 | 0 | 3 | 3 | 3 | 3 | 3 | 3 | 3 | 3 |
| | 0.2803 | 0 | | | 0 | – | 0 | 0 | | 0 | 0 | 0 | 0 | 0 | 0 | 0 | 0 | 0 | 0 | 0 | 0 | – |
| | 0.1401 | 0 | | | 0 | – | Z | 0 | | 0 | 0 | 0 | Z | 0 | 1 | 1 | 0 | 1 | 1 | Z | 0 | 1 |
| | 0.0701 | 0 | | | 0 | Z | 0 | 0 | | 0 | 0 | 0 | 0 | 0 | Z | 0 | 0 | 0 | 0 | Z | 0 | 0 |
| | 0.0350 | 0 | | | 0 | 3 | 3 | 3 | | 3 | 3 | 3 | 3 | 0 | 3 | 3 | 3 | 3 | 3 | 0 | 3 | 3 |
| | 0.0175 | 0 | | | 0 | 3 | – | 0 | | 0 | 0 | 0 | 0 | 0 | 3 | 3 | 3 | 3 | 3 | 3 | 3 | 3 |
| | 0.0087 | 0 | | | 0 | 1 | 0 | 0 | | 0 | 0 | 0 | 0 | – | 0 | 0 | 0 | 0 | 0 | 0 | 0 | 0 |
| 21 | 5.6050 | 3 | | | 0 | 3 | 3 | 3 | | 3 | 3 | 3 | 3 | 3 | 3 | 3 | 3 | 3 | 3 | 3 | 3 | 3 |
| | 1.1210 | 2 | | | 0 | 3 | 3 | 3 | | 3 | 3 | 3 | 3 | 1 | 3 | 3 | 3 | 3 | 3 | 3 | 3 | 3 |
| | 0.5605 | 2 | | | 0 | 3 | 3 | 3 | | 3 | 3 | 3 | 3 | 0 | 3 | 3 | 3 | 3 | 3 | 3 | 3 | 3 |
| | 0.2803 | 0 | | | 0 | 2 | 3 | 3 | | 3 | 3 | 3 | 3 | 0 | 3 | 3 | 3 | 3 | 3 | 2 | 3 | 3 |
| | 0.1401 | 0 | | | 0 | – | 2 | 2 | | 2 | 2 | 3 | 2 | 0 | 3 | 2 | 2 | 3 | 2 | 1 | 2 | 3 |
| | 0.0701 | 0 | | | 0 | 0 | – | – | | 0 | – | – | 2 | 0 | 3 | 0 | 0 | 0 | 0 | – | – | – |
| | 0.0350 | 0 | | | 0 | 0 | 0 | 0 | | 0 | 0 | 0 | 0 | 0 | – | 0 | 0 | 0 | 0 | – | 0 | – |
| | 0.0175 | 0 | | | 0 | 0 | 0 | 0 | | 0 | 0 | 0 | 0 | 0 | 0 | 0 | 0 | 0 | 0 | 0 | 0 | 0 |
| | 0.0087 | 0 | | | 0 | 0 | 0 | 0 | | 0 | 0 | 0 | 0 | 0 | 0 | 0 | 0 | 0 | 0 | 0 | 0 | 0 |
| 22 | 5.6050 | 0 | | | 0 | 3 | 3 | 1 | | 3 | 3 | 3 | 3 | 3 | 3 | 3 | 3 | 3 | 3 | 3 | 3 | 3 |
| | 5.6050 | 0 | | | 1 | 3 | 2 | 3 | | 3 | 3 | 3 | – | – | – | 0 | – | 0 | 3 | 0 | 0 | 3 |
| | 1.1210 | 0 | | | 0 | 3 | 3 | 3 | | 3 | 3 | 3 | 3 | 3 | 3 | 3 | 3 | 3 | 3 | 3 | 3 | 3 |

TABLE B-continued

| Ex. No. | Rate kg/ha | Sobe | Cotz | Rape | Cobu | Wibw | Mogl | Hese | Jiwe | Vele | Whez | Rice | Grso | Corn | Dobr | Prmi | Bygr | Lacg | Grft | Sube | Colq | Pesw |
|---|---|---|---|---|---|---|---|---|---|---|---|---|---|---|---|---|---|---|---|---|---|---|
| 22 | 1.1210 | 0 | | | 0 | 0 | 0 | 0 | | 0 | 0 | 0 | 0 | 0 | 0 | 0 | 0 | 0 | 0 | 0 | 0 | 0 |
| | 0.5605 | 0 | | | 0 | 3 | 0 | 3 | | 3 | 3 | 3 | 2 | 0 | 3 | 3 | 3 | 3 | 3 | 0 | 3 | 3 |
| | 0.5605 | 0 | | | 0 | 3 | 1 | 0 | | 1 | 2 | 2 | 1 | 0 | 3 | 3 | 3 | 3 | 3 | 1 | 3 | 3 |
| | 0.2803 | 0 | | | 0 | 0 | 2 | 0 | | 0 | 0 | 0 | 0 | 0 | 0 | 0 | 0 | 0 | 0 | 0 | 0 | 0 |
| | 0.2803 | 0 | | | 0 | 0 | 0 | 0 | | 0 | 0 | 0 | 0 | 0 | 0 | 0 | 0 | 0 | 0 | 0 | 0 | 0 |
| | 0.1401 | 0 | | | 0 | 0 | 0 | 0 | | 0 | 0 | 0 | 0 | 0 | 0 | 0 | 0 | 0 | 2 | 0 | 0 | 3 |
| | 0.1401 | 0 | | | 0 | 0 | 0 | 0 | | 0 | 0 | 0 | 0 | 0 | 2 | 2 | 0 | 3 | 2 | 0 | 2 | 0 |
| | 0.0701 | 0 | | | 0 | 0 | 1 | 0 | | 0 | 1 | 0 | 0 | 0 | 2 | 2 | 2 | 0 | Z | 0 | 0 | 1 |
| | 0.0701 | 0 | | | 1 | 0 | 0 | 0 | | 0 | 0 | 0 | 0 | 0 | 0 | 0 | 0 | 0 | 0 | 0 | 0 | 0 |
| | 0.0350 | 0 | | | 0 | 0 | 0 | 0 | | 0 | 0 | 0 | 0 | 0 | 1 | 0 | 0 | 0 | 1 | 0 | 1 | 0 |
| | 0.0350 | 0 | | | 0 | 0 | 0 | 0 | | 0 | 0 | 0 | 0 | 0 | 1 | 0 | Z | 0 | Z | 0 | 1 | 0 |
| | 0.0175 | 0 | | | 0 | 0 | 0 | 0 | | 0 | 0 | 0 | 0 | 0 | Z | 0 | 2 | 0 | Z | Z | Z | 0 |
| | 0.0175 | 0 | | | 0 | 0 | 0 | 0 | | 0 | 0 | 0 | 0 | 0 | 0 | 0 | 0 | 0 | 0 | 0 | 0 | 0 |
| | 0.0087 | 0 | | | 0 | 0 | 0 | 0 | | 0 | 0 | 0 | 0 | 0 | 0 | 0 | 0 | 0 | 0 | 0 | 0 | 0 |
| 23 | 5.6050 | 3 | | | 0 | 3 | 3 | 3 | | 3 | 3 | 3 | 3 | 3 | 3 | 3 | 3 | 3 | 3 | 3 | 3 | 3 |
| | 1.1210 | 0 | | | 0 | 3 | 1 | 1 | | 2 | 3 | 3 | 2 | 1 | 3 | 3 | 3 | 3 | 3 | 3 | 3 | 3 |
| | 0.5605 | 0 | | | 0 | 3 | 1 | 2 | | 1 | 3 | 1 | 3 | 0 | 2 | 3 | 3 | 3 | 3 | 3 | 3 | 3 |
| | 0.2803 | 0 | | | 0 | 3 | 2 | Z | | Z | 3 | 3 | 2 | 0 | 3 | 2 | 3 | 3 | 3 | 3 | 3 | 2 |
| | 0.1401 | 0 | | | 0 | 3 | Z | 0 | | 2 | 0 | 0 | 0 | 0 | 3 | 0 | 3 | 3 | 2 | 1 | Z | 1 |
| | 0.0701 | 0 | | | 0 | 0 | 0 | Z | | 0 | 0 | 0 | 0 | 0 | 0 | 3 | 0 | 3 | 0 | 0 | 0 | 0 |
| | 0.0350 | 0 | | | 0 | 0 | 0 | Z | | Z | 0 | 0 | 0 | 0 | 0 | 0 | 0 | 0 | 0 | 0 | 0 | 0 |
| 24 | 5.6050 | 0 | | | 0 | 3 | 3 | 3 | | 3 | 3 | 3 | 3 | 3 | 3 | 3 | 3 | 3 | 3 | 3 | 3 | 3 |
| | 1.1210 | 0 | | | 0 | 0 | 0 | 0 | | 0 | 0 | 0 | 0 | 0 | 0 | 0 | 0 | 0 | 0 | 0 | 0 | 0 |
| | 0.5605 | 0 | | | 0 | 0 | 0 | 0 | | 0 | 0 | 0 | 0 | 0 | 0 | 0 | 0 | 0 | 0 | 0 | 0 | 0 |
| | 0.2803 | 0 | | | 0 | 0 | 0 | 0 | | 0 | 0 | 0 | 0 | 0 | 0 | 0 | 0 | 0 | 0 | 0 | 0 | 0 |
| | 0.1401 | 0 | | | 1 | 0 | 0 | 0 | | 0 | 0 | 0 | 0 | 0 | 0 | 0 | 0 | 0 | 0 | 0 | 0 | 0 |
| | 0.0701 | 0 | | | 0 | 0 | 0 | 0 | | 0 | 0 | 0 | 0 | 0 | 0 | 0 | 0 | 0 | 0 | 0 | 0 | 0 |
| | 0.0350 | 0 | | | 0 | 0 | 0 | 0 | | 0 | 0 | 0 | 0 | 0 | 0 | 0 | 0 | 0 | 0 | 0 | 0 | 0 |
| 25 | 5.6050 | 1 | | | 0 | 3 | 3 | 3 | | 3 | 3 | 3 | 3 | 0 | 3 | 3 | 3 | 3 | 3 | 3 | 3 | 3 |
| | 1.1210 | 0 | | | 0 | 3 | 0 | 1 | | 1 | 2 | 2 | 2 | 3 | 2 | 2 | 2 | 3 | 3 | 3 | 3 | 3 |
| | 0.5605 | 0 | | | 0 | 0 | 2 | Z | | 2 | 1 | 2 | 3 | 2 | 2 | 2 | 1 | 3 | 3 | 2 | 2 | 2 |
| | 0.2803 | 0 | | | 0 | 3 | 0 | 0 | | 0 | 0 | 0 | 1 | 1 | 0 | 0 | 0 | 3 | 0 | 0 | 0 | 0 |
| 25 | 0.1401 | Z | | | 0 | 0 | 0 | 0 | | 0 | 0 | 0 | 0 | 2 | 0 | 0 | 0 | 3 | 0 | 0 | 0 | 1 |
| | 0.0701 | 0 | | | 0 | 0 | 0 | 0 | | 0 | 0 | 0 | 0 | 0 | 0 | 0 | 0 | 0 | 0 | 0 | 0 | 0 |
| 26 | 5.6050 | 0 | | | 0 | 3 | 0 | 0 | | 3 | 3 | 2 | 0 | 0 | 3 | 3 | 3 | 3 | 3 | 3 | 3 | 3 |
| | 1.1210 | 0 | | | 0 | 3 | 0 | 0 | | 3 | 0 | 0 | 0 | 0 | 3 | 3 | 3 | 3 | 3 | 1 | 3 | 3 |
| | 0.5605 | 0 | | | 0 | 2 | 0 | 0 | | 2 | 0 | 0 | 0 | 0 | 2 | 3 | 3 | 3 | 3 | 0 | 3 | 3 |
| | 0.2803 | 0 | | | 0 | 1 | 0 | 0 | | 1 | 0 | 0 | 0 | 0 | 2 | 2 | 2 | 2 | 3 | 0 | 2 | 2 |
| | 0.1401 | 0 | | | 0 | 0 | 0 | 0 | | 0 | 0 | 0 | 0 | 0 | 0 | 1 | 1 | 2 | 1 | 0 | 0 | 0 |
| 26 | 0.0701 | 0 | | | 0 | 0 | 0 | 0 | | 0 | 0 | 0 | 0 | 0 | 0 | 1 | 1 | 2 | 1 | 0 | 1 | 1 |
| 27 | 5.6050 | 3 | | | 3 | 3 | 3 | 3 | | 3 | 3 | 3 | 3 | 0 | 3 | 3 | 3 | 3 | 3 | 3 | 3 | 3 |
| | 1.1210 | 3 | | | 1 | 3 | 3 | 3 | | 3 | 3 | 3 | 3 | 0 | 3 | 3 | 3 | 3 | 3 | 3 | 3 | 3 |
| | 0.2803 | 0 | | | 1 | 3 | 3 | 3 | | 2 | 2 | 2 | 3 | 0 | 3 | 3 | 3 | 3 | 3 | 3 | 3 | 2 |
| | 0.0561 | 0 | | | 1 | 3 | 3 | 3 | | 2 | 0 | 3 | 3 | 0 | 3 | 3 | 3 | 3 | 1 | 1 | 1 | 1 |
| | 0.0112 | 0 | | | Z | 3 | 2 | 2 | | 3 | 3 | 3 | 3 | 0 | 3 | 3 | 3 | 3 | 2 | 0 | 0 | 0 |
| | 0.0056 | 0 | | | | 2 | 3 | 3 | | 2 | 3 | 3 | 3 | | 3 | 3 | 3 | 3 | | 0 | 3 | 3 |
| | 0.0011 | 0 | | | | 3 | 3 | 3 | | 3 | 3 | 3 | 3 | | 3 | 3 | 3 | 3 | | 3 | 3 | 3 |
| 28 | 5.6050 | 3 | | | | 3 | 3 | 3 | | 2 | 3 | 3 | 3 | | 3 | 3 | 3 | 3 | | 3 | 3 | 3 |
| | 1.1210 | 3 | | | | 2 | 3 | 3 | | 2 | 3 | 3 | 3 | | 3 | 3 | 3 | 3 | | 3 | 3 | 3 |
| | 0.2803 | 2 | | | | 3 | 2 | 3 | | 2 | 3 | 3 | 3 | | 3 | 3 | 0 | 3 | | 3 | 3 | 3 |
| | 0.0561 | 1 | | | | 3 | 3 | 2 | | 2 | 0 | 2 | 3 | | 3 | 3 | 3 | 3 | | 1 | 3 | 2 |

TABLE B-continued

| Ex. No. | Rate kg/ha | Sobe | Cotz | Rape | Cobu | Wibw | Mogl | Hese | Jiwe | Vele | Whez | Rice | Grso | Corn | Dobr | Prmi | Bygr | Lacg | Grft | Sube | Colq | Pesw |
|---|---|---|---|---|---|---|---|---|---|---|---|---|---|---|---|---|---|---|---|---|---|---|
| 29 | 0.0112 | 0 | | | 0 | 0 | 0 | 0 | | 1 | 0 | 1 | 1 | | 0 | 1 | 3 | 2 | | 1 | 1 | 0 |
|  | 0.0056 | 0 | | | 0 | 0 | 1 | 1 | | 0 | 0 | 1 | 0 | | 0 | 3 | 1 | 3 | | 3 | 3 | 1 |
|  | 5.6050 | 2 | | | 0 | 2 | 3 | 3 | | 3 | 3 | 3 | 3 | | 3 | 3 | 3 | 3 | | 3 | 3 | 3 |
|  | 1.1210 | 0 | | | 0 | 3 | 2 | 2 | | 2 | 0 | 2 | 3 | | 0 | 3 | 3 | 3 | | 0 | 0 | 0 |
|  | 0.2803 | 0 | | | 0 | 0 | 0 | 0 | | 0 | 0 | 0 | 0 | | 0 | 0 | 0 | 0 | | 0 | 0 | 0 |
|  | 0.0561 | 3 | | | 0 | 3 | 3 | 3 | | 3 | 3 | 3 | 3 | | 3 | 3 | 3 | 3 | | 3 | 3 | 3 |
| 30 | 5.6050 | 3 | | | 0 | 3 | 3 | 3 | | 3 | 3 | 3 | 3 | | 3 | 3 | 3 | 3 | | 3 | 3 | 3 |
|  | 1.1210 | 3 | | | 0 | 3 | 3 | 3 | | 2 | 3 | 3 | 3 | | 3 | 3 | 3 | 3 | | 2 | 3 | 3 |
|  | 0.2803 | 0 | | | 0 | 2 | 2 | 2 | | 2 | 2 | 2 | 3 | | 3 | 3 | 3 | 3 | | 2 | 3 | 3 |
|  | 0.0561 | 0 | | | 0 | 2 | 2 | 2 | | 0 | 0 | 0 | 2 | | 1 | 3 | 2 | 2 | | 2 | 3 | 1 |
| 31 | 5.6050 | 2 | | | 0 | 0 | 3 | 3 | | 3 | 3 | 3 | 3 | | 3 | 3 | 3 | 3 | | 3 | 3 | 3 |
|  | 1.1210 | 1 | | | 0 | 0 | 2 | 2 | | 2 | 0 | 1 | 0 | | 0 | 0 | 2 | 0 | | 0 | 0 | 0 |
|  | 0.2803 | 0 | | | 0 | 0 | 0 | 0 | | 0 | 0 | 0 | 0 | | 0 | 0 | 0 | 0 | | 0 | 0 | 0 |
|  | 0.0561 | 0 | | | 0 | 3 | 3 | 3 | | 3 | 3 | 3 | 3 | | 3 | 3 | 3 | 3 | | 3 | 3 | 3 |
| 32 | 5.6050 | 3 | | | 0 | 0 | 3 | 2 | | 3 | 3 | 0 | 2 | | 3 | 3 | 3 | 3 | | 3 | 3 | 3 |
|  | 1.1210 | 2 | | | 0 | 0 | 3 | 2 | | 1 | 0 | 1 | 0 | | 2 | 3 | 3 | 3 | | 2 | 3 | 2 |
|  | 0.2803 | 0 | | | 0 | 0 | 0 | 0 | | 0 | 0 | 0 | 0 | | 1 | 0 | 0 | 0 | | 0 | 0 | 0 |
|  | 0.0561 | 0 | | | 0 | 0 | 0 | 0 | | 0 | 0 | 0 | 0 | | 0 | 0 | 0 | 0 | | 0 | 0 | 0 |
|  | 0.0112 | 3 | | | 0 | 3 | 3 | 3 | | 3 | 3 | 3 | 3 | | 3 | 3 | 3 | 3 | | 3 | 3 | 3 |
| 33 | 5.6050 | 3 | | | 3 | 3 | 3 | 3 | | 2 | 3 | 3 | 3 | | 3 | 3 | 3 | 3 | | 3 | 3 | 3 |
|  | 1.1210 | 0 | | | 0 | 0 | 1 | 1 | | 1 | 0 | 0 | 1 | | 0 | 0 | 1 | 2 | | 2 | 1 | 2 |
|  | 0.2803 | 0 | | | 0 | 0 | 0 | 0 | | 0 | 0 | 0 | 0 | | 0 | 0 | 0 | 0 | | 0 | 0 | 0 |
|  | 0.0561 | 0 | | | 0 | 3 | 3 | 3 | | 3 | 3 | 3 | 3 | | 3 | 3 | 3 | 3 | | 3 | 3 | 3 |
| 34 | 5.6050 | 3 | | | 3 | 3 | 3 | 3 | | 3 | 3 | 3 | 3 | | 3 | 3 | 3 | 3 | | 3 | 3 | 3 |
|  | 1.1210 | 3 | | | 1 | 3 | 3 | 3 | | 3 | 2 | 2 | 3 | | 3 | 3 | 3 | 3 | | 3 | 3 | 3 |
|  | 0.2803 | 3 | | | 0 | 3 | 3 | 3 | | 3 | 3 | 3 | 3 | | 3 | 3 | 3 | 3 | | 3 | 3 | 3 |
|  | 0.0561 | 0 | | | 0 | 0 | 0 | 0 | | 0 | 0 | 0 | 0 | | 0 | 1 | 1 | 3 | | 1 | 1 | 1 |
| 35 | 0.0112 | 0 | | | 0 | 0 | 0 | 0 | | 0 | 0 | 0 | 0 | | 0 | 0 | 0 | 0 | | 0 | 0 | 0 |
|  | 0.0056 | 3 | | | 0 | 3 | 3 | 3 | | 3 | 3 | 3 | 3 | | 3 | 3 | 3 | 3 | | 3 | 3 | 3 |
|  | 5.6050 | 3 | | | 0 | 3 | 3 | 3 | | 3 | 3 | 3 | 3 | | 3 | 3 | 3 | 3 | | 3 | 3 | 3 |
|  | 1.1210 | 1 | | | 0 | 3 | 3 | 3 | | 2 | 2 | 2 | 3 | | 0 | 3 | 3 | 3 | | 3 | 3 | 3 |
|  | 0.2803 | 0 | | | 0 | 0 | 2 | 0 | | 0 | 0 | 0 | 0 | | 1 | 1 | 0 | 1 | | 0 | 0 | 2 |
|  | 0.0561 | 0 | | | 0 | 0 | 0 | 0 | | 0 | 0 | 0 | 0 | | 0 | 0 | 0 | 0 | | 0 | 0 | 0 |
|  | 0.0112 | 0 | | | 0 | 0 | 0 | 0 | | 0 | 0 | 0 | 0 | | 0 | 0 | 0 | 0 | | 0 | 0 | 0 |
|  | 0.0056 | 0 | | | 0 | 0 | 0 | 0 | | 0 | 0 | 0 | 0 | | 0 | 0 | 0 | 0 | | 0 | 0 | 0 |
| 36 | 5.6050 | 3 | | | 0 | 3 | 3 | 3 | | 3 | 3 | 3 | 3 | | 3 | 3 | 3 | 3 | | 3 | 3 | 3 |
|  | 1.1210 | 3 | | | 0 | 3 | 3 | 3 | | 3 | 3 | 3 | 3 | | 3 | 3 | 3 | 3 | | 3 | 3 | 3 |
|  | 0.2803 | 1 | | | 0 | 2 | 1 | 1 | | 0 | 0 | 2 | 1 | | 1 | 1 | 1 | 1 | | 1 | 1 | 1 |
|  | 0.0561 | 0 | | | 0 | 0 | 0 | 0 | | 0 | 0 | 0 | 0 | | 0 | 0 | 0 | 0 | | 0 | 0 | 0 |
| 37 | 0.0112 | 0 | | | 0 | 3 | 3 | 3 | | 3 | 3 | 3 | 3 | | 3 | 3 | 3 | 3 | | 3 | 3 | 3 |
|  | 5.6050 | 3 | | | 0 | 3 | 3 | 3 | | 3 | 3 | 3 | 3 | | 3 | 3 | 3 | 3 | | 3 | 3 | 3 |
|  | 1.1210 | 3 | | | 0 | 3 | 3 | 3 | | 2 | 2 | 2 | 3 | | 3 | 3 | 3 | 3 | | 2 | 3 | 3 |
|  | 0.2803 | 0 | | | 0 | 3 | 1 | 1 | | 0 | 0 | 0 | 0 | | 0 | 0 | 0 | 2 | | 0 | 0 | 0 |
|  | 0.0561 | 0 | | | 0 | 0 | 0 | 0 | | 0 | 0 | 0 | 0 | | 0 | 0 | 0 | 0 | | 0 | 0 | 0 |
|  | 0.0112 | 0 | | | 0 | 3 | 3 | 3 | | 3 | 3 | 3 | 3 | | 3 | 3 | 3 | 3 | | 3 | 3 | 3 |
| 38 | 5.6050 | 3 | | | 0 | 3 | 3 | 3 | | 3 | 3 | 3 | 3 | | 3 | 3 | 3 | 3 | | 3 | 3 | 3 |
|  | 1.1210 | 3 | | | 0 | 3 | 3 | 3 | | 3 | 3 | 3 | 3 | | 3 | 3 | 3 | 3 | | 3 | 3 | 3 |
|  | 0.2803 | 0 | | | 0 | 1 | 2 | 2 | | 2 | 0 | 2 | 3 | | 2 | 2 | 0 | 2 | | 2 | 2 | 2 |
|  | 0.0561 | 0 | | | 0 | 0 | 0 | 0 | | 0 | 0 | 0 | 0 | | 1 | 0 | 3 | 3 | | 3 | 3 | 0 |
|  | 0.0112 | 0 | | | 1 | 0 | 0 | 0 | | 3 | 3 | 3 | 3 | | 3 | 3 | 3 | 3 | | 3 | 3 | 3 |
| 40 | 5.6050 | 3 | | | | 3 | 3 | 3 | | 3 | 3 | 3 | 3 | | 3 | 3 | 3 | 3 | | 3 | 3 | 3 |

TABLE B-continued

| Ex. No. | Rate kg/ha | Sobe | Cotz | Rape | Cobu | Wibw | Mogl | Hese | Jiwe | Vele | Whez | Rice | Grso | Corn | Dobr | Prmi | Bygr | Lacg | Grft | Sube | Colq | Pesw |
|---|---|---|---|---|---|---|---|---|---|---|---|---|---|---|---|---|---|---|---|---|---|---|
| | 1.1210 | 2 | | | 0 | 3 | 2 | 3 | | 3 | 3 | 2 | 3 | | 3 | 3 | 3 | 3 | | 3 | 3 | 3 |
| | 0.5605 | 2 | | | 0 | 3 | 2 | 3 | | 3 | 2 | 2 | 3 | | 3 | 3 | 3 | 3 | | 3 | 3 | 3 |
| | 0.2803 | 2 | | | 0 | 3 | 1 | 3 | | 1 | 0 | 2 | 2 | | 3 | 3 | 3 | 3 | | 2 | 0 | 3 |
| | 0.1401 | 0 | | | 0 | 3 | 1 | 1 | | 0 | 0 | 1 | 1 | | 2 | 3 | 3 | 3 | | 2 | 1 | 3 |
| | 0.0701 | 0 | | | 0 | 0 | 0 | 1 | | 1 | 0 | 0 | 1 | | 2 | 3 | 3 | 3 | | 1 | 1 | 2 |
| | 0.0350 | 3 | | | 2 | 3 | 3 | 3 | | 3 | 3 | 3 | 3 | | 3 | 3 | 3 | 3 | | 3 | 3 | 3 |
| 41 | 5.6050 | 3 | | | 1 | 3 | 3 | 3 | | 3 | 3 | 3 | 3 | | 3 | 3 | 3 | 3 | | 3 | 3 | 3 |
| | 1.1210 | 1 | | | 0 | 3 | 3 | 3 | | 3 | 3 | 3 | 2 | | 3 | 3 | 3 | 3 | | 3 | 3 | 2 |
| | 0.2803 | 0 | | | 0 | N | 1 | 2 | | 2 | 2 | 2 | 0 | | 2 | 2 | 2 | 3 | | 2 | 1 | 0 |
| | 0.0561 | 0 | | | 0 | 1 | 0 | 1 | | 0 | 0 | 1 | 1 | | 0 | 1 | 0 | 1 | | 1 | 0 | 0 |
| | 0.0112 | 1 | | | 0 | 0 | 0 | 0 | | 0 | 0 | 0 | 0 | | 0 | 0 | 0 | 0 | | 0 | 0 | 0 |
| 42 | 5.6050 | 3 | | | 0 | 3 | 3 | 3 | | 3 | 3 | 3 | 3 | | 3 | 3 | 3 | 3 | | 3 | 3 | 3 |
| | 1.1210 | 2 | | | 1 | 3 | 3 | 3 | | 3 | 2 | 3 | 2 | | 3 | 3 | 3 | 3 | | 3 | 3 | 3 |
| | 0.5605 | 1 | | | 0 | 3 | 2 | 3 | | 2 | 1 | 1 | 1 | | 2 | 3 | 3 | 3 | | 2 | 2 | 2 |
| | 0.2803 | 0 | | | 0 | 3 | 1 | 3 | | 2 | 0 | 0 | 0 | | 0 | 3 | 0 | 3 | | 1 | 1 | 2 |
| | 0.1401 | 0 | | | 0 | 3 | 1 | 2 | | 0 | 0 | 0 | 0 | | 0 | 3 | 0 | 3 | | 1 | 0 | 1 |
| 42 | 0.0701 | 0 | | | 0 | 0 | 0 | 0 | | 0 | 0 | 0 | 0 | | 0 | 0 | 0 | 1 | | 0 | 0 | 0 |
| | 0.0350 | 0 | | | 0 | 0 | 0 | 0 | | 0 | 0 | 0 | 0 | | 0 | 0 | 0 | 0 | | 0 | 0 | 0 |
| * | 0.0175 | 0 | | | 0 | 0 | 0 | 0 | | 0 | 0 | 0 | 0 | | 0 | 0 | 0 | 3 | 3 | 0 | 0 | 0 |
| * | 0.0087 | 0 | | | 0 | 0 | 0 | 0 | | 0 | 0 | 0 | 0 | | 0 | 0 | 0 | 1 | 1 | 0 | 0 | 2 |
| 43 | 5.6050 | 3 | | | 0 | 3 | 3 | 3 | | 3 | 3 | 3 | 3 | | 3 | 3 | 3 | 3 | | 3 | 3 | 3 |
| | 1.1210 | 3 | | | 1 | 3 | 3 | 3 | | 3 | 3 | 3 | 3 | | 3 | 3 | 3 | 3 | | 3 | 3 | 3 |
| | 0.5605 | 0 | | | 0 | 3 | 2 | 3 | | 3 | 1 | 3 | 3 | | 2 | 3 | 3 | 3 | | 3 | 3 | 3 |
| | 0.2803 | 0 | | | 0 | 3 | 2 | 3 | | 2 | 0 | 2 | 2 | | 2 | 3 | 3 | 3 | | 3 | 3 | 3 |
| | 0.1401 | 0 | | | 0 | 2 | 0 | 2 | | 2 | 0 | 2 | 1 | | 2 | 2 | 2 | 2 | | 2 | 2 | 2 |
| 43 | 0.0701 | 0 | | | 0 | 2 | 0 | 0 | | 0 | 0 | 0 | 0 | | 0 | 1 | 0 | 3 | | 1 | 0 | 1 |
| | 0.0350 | 0 | | | 0 | 0 | 0 | 0 | | 0 | 0 | 0 | 0 | | 0 | 0 | 0 | 1 | | 0 | 0 | 0 |
| | 0.0175 | 0 | | | 0 | 0 | 0 | 0 | | 0 | 0 | 0 | 0 | | 0 | 0 | 0 | 1 | | 0 | 0 | 0 |
| | 0.0087 | 0 | | | 0 | 0 | 0 | 0 | | 0 | 0 | 0 | 0 | | 0 | 0 | 0 | 0 | | 0 | 0 | 0 |
| 44 | 5.6050 | 3 | | | 2 | 3 | 3 | 3 | | 3 | 3 | 3 | 3 | | 3 | 3 | 3 | 3 | | 3 | 3 | 3 |
| | 1.1210 | 3 | | | 1 | 3 | 3 | 3 | | 3 | 3 | 3 | 3 | | 3 | 3 | 3 | 3 | | 3 | 3 | 3 |
| | 0.5605 | 3 | | | 0 | 3 | 2 | 3 | | 3 | 0 | 2 | 2 | | 0 | 3 | 2 | 3 | | 2 | 2 | 3 |
| | 0.2803 | 1 | | | 0 | 2 | 0 | 2 | | 2 | 0 | 1 | 0 | | 0 | 1 | 0 | 1 | | 1 | 0 | 2 |
| | 0.1401 | 0 | | | 0 | 0 | 0 | 0 | | 0 | 0 | 0 | 0 | | 0 | 0 | 0 | 1 | | 0 | 0 | 1 |
| | 0.0701 | 0 | | | 0 | 0 | 0 | 0 | | 0 | 0 | 0 | 0 | | 0 | 0 | 0 | 0 | | 0 | 0 | 0 |
| 45 | 5.6050 | 3 | | | 3 | 3 | 3 | 3 | | 3 | 3 | 3 | 3 | 3 | 3 | 3 | 3 | 3 | 3 | 3 | 3 | 3 |
| | 1.1210 | 3 | | | 3 | 3 | 3 | 3 | | 3 | 3 | 3 | 3 | 3 | 3 | 3 | 3 | 3 | 3 | 3 | 3 | 3 |
| | 0.5605 | 1 | | | 1 | 3 | 3 | 3 | | 3 | 3 | 3 | 3 | 2 | 2 | 3 | 3 | 3 | 3 | 3 | 3 | 3 |
| | 0.2803 | 0 | | | 1 | 2 | 2 | 3 | | 2 | 2 | 2 | 2 | 1 | 2 | 3 | 3 | 3 | 3 | 2 | 2 | 1 |
| 45 | 0.1401 | 0 | | | 1 | 2 | 2 | 2 | | 2 | 2 | 2 | 2 | 1 | 2 | 3 | 3 | 3 | 3 | 2 | 2 | 1 |
| | 0.0701 | 0 | | | 0 | 1 | 0 | 1 | | 0 | 0 | 0 | 0 | 0 | 0 | 1 | 0 | 3 | 3 | 1 | 0 | 1 |
| | 0.0350 | 0 | | | 0 | 1 | 0 | 0 | | 0 | 0 | 0 | 0 | 0 | 0 | 3 | 0 | 3 | 3 | 1 | 0 | 3 |
| | 0.0175 | 0 | | | 0 | 0 | 0 | 0 | | 0 | 0 | 0 | 0 | 0 | 1 | 3 | 0 | 3 | 3 | 1 | 1 | 0 |
| 46 | 5.6050 | 3 | | | 0 | 3 | 3 | 3 | | 3 | 3 | 3 | 3 | | 3 | 3 | 3 | 3 | 3 | 3 | 3 | 3 |
| | 1.1210 | 2 | | | 0 | 3 | 2 | 3 | | 3 | 3 | 3 | 3 | | 3 | 3 | 3 | 3 | 3 | 3 | 3 | 3 |
| | 0.5605 | 0 | | | 0 | 3 | 2 | 3 | | 3 | 2 | 3 | 3 | | 2 | 3 | 3 | 3 | 3 | 3 | 3 | 3 |
| | 0.2803 | 0 | | | 0 | 2 | 1 | 3 | | 3 | 1 | 3 | 3 | | 1 | 3 | 3 | 3 | 3 | 3 | 3 | 3 |
| | 0.1401 | 0 | | | 0 | 1 | 0 | 3 | | 3 | 0 | 2 | 3 | | 2 | 3 | 3 | 3 | 3 | 3 | 3 | 3 |

TABLE B-continued

| Ex. No. | Rate kg/ha | Sobe | Cotz | Rape | Cobu | Wibw | Mogl | Hese | Jiwe | Vele | Whez | Rice | Grso | Corn | Dobr | Prmi | Bygr | Lacg | Grft | Sube | Colq | Pesw |
|---|---|---|---|---|---|---|---|---|---|---|---|---|---|---|---|---|---|---|---|---|---|---|
| 46 | 0.0701 | 0 | | | 0 | 1 | 1 | 2 | | 1 | 1 | 3 | 2 | 1 | 1 | 3 | 3 | 3 | 3 | 2 | 3 | 3 |
| | 0.0350 | 0 | | | 0 | 1 | 0 | 2 | | 0 | 0 | 2 | 2 | 0 | 2 | 3 | 3 | 3 | 3 | 0 | 3 | 3 |
| | 0.0175 | 0 | | | 0 | 0 | 0 | 0 | | 0 | 0 | 1 | 0 | Z | 0 | 2 | 1 | 2 | 2 | 1 | 2 | 2 |
| | 0.0087 | 0 | | | 0 | 0 | 0 | 0 | | 0 | 0 | 2 | 0 | 2 | 0 | 0 | 0 | 0 | 2 | 0 | 0 | 1 |
| 47 | 5.6050 | 2 | | | 0 | 3 | 3 | 3 | | 3 | 2 | 2 | 3 | 0 | 3 | 3 | 3 | 3 | 3 | 3 | 3 | 3 |
| | 1.1210 | 0 | | | 0 | 3 | 2 | 3 | | 2 | 1 | 3 | 3 | 0 | 2 | 3 | 3 | 3 | 3 | 2 | 3 | 3 |
| | 0.5605 | 0 | | | 0 | 2 | 3 | 2 | | 2 | 0 | 2 | 3 | 0 | 3 | 3 | 3 | 3 | 3 | 0 | 3 | 3 |
| | 0.2803 | 0 | | | 0 | 0 | 0 | 3 | | 2 | 0 | 0 | 3 | 0 | 2 | 3 | 3 | 3 | 3 | 0 | 3 | 3 |
| | 0.1401 | 0 | | | 0 | 0 | 0 | 1 | | 2 | 0 | 0 | 3 | 0 | 0 | 3 | 3 | 2 | 3 | 0 | 0 | 1 |
| 47 | 0.0701 | 0 | | | 0 | 0 | 0 | 0 | | 0 | 0 | 0 | 3 | 0 | 0 | 0 | 0 | 0 | 0 | 0 | 0 | 0 |
| | 0.0350 | 0 | | | 0 | 0 | 0 | 0 | | 0 | 0 | 0 | 0 | 0 | 0 | 0 | 0 | 0 | 0 | 0 | 0 | 0 |
| | 0.0175 | 0 | | | 0 | 0 | 0 | 0 | | 0 | 0 | 0 | 0 | 0 | 0 | 0 | 0 | 0 | 0 | 0 | 0 | 0 |
| | 0.0087 | 0 | | | 0 | 0 | 0 | 0 | | 0 | 0 | 0 | 0 | 0 | 0 | 0 | 0 | 0 | 0 | 0 | 0 | 0 |
| 48 | 5.6050 | 3 | | | 0 | 3 | 3 | 3 | | 3 | 2 | 3 | 3 | 3 | 3 | 3 | 3 | 3 | 3 | 3 | 3 | 3 |
| | 1.1210 | 3 | | | 0 | 3 | 2 | 3 | | 2 | 1 | 2 | 3 | 3 | 3 | 3 | 3 | 3 | 3 | 3 | 3 | 3 |
| | 0.5605 | 1 | | | 0 | 3 | 3 | 3 | | 2 | 0 | 2 | Z | 3 | 3 | 3 | 3 | 3 | 3 | 3 | 3 | 3 |
| | 0.2803 | 0 | | | 0 | 2 | 2 | 3 | | 2 | 0 | 2 | Z | 3 | 0 | 3 | 3 | 3 | 3 | 3 | 3 | 3 |
| | 0.1401 | 0 | | | 0 | 2 | 2 | 3 | | 3 | 0 | 3 | 2 | 1 | 3 | 3 | 3 | 3 | 3 | 2 | 0 | 3 |
| 48 | 0.0701 | 0 | | | 0 | 2 | 2 | 3 | | 3 | 0 | 3 | Z | 0 | 2 | 3 | 3 | 3 | 3 | 1 | 0 | 3 |
| | 0.0350 | 0 | | | 0 | 2 | 0 | 1 | | N | 0 | 0 | 2 | 0 | 0 | 2 | 2 | 2 | 2 | 1 | 0 | 1 |
| | 0.0175 | 0 | | | 0 | 2 | 0 | 1 | | 1 | 0 | 0 | 2 | 0 | 0 | 1 | 1 | 1 | 1 | 0 | 0 | 0 |
| | 0.0087 | 0 | | | 0 | 2 | 0 | 0 | | 0 | 0 | 0 | 1 | 0 | 0 | 0 | 0 | 0 | 0 | 0 | 0 | 0 |
| 49 | 5.6050 | 2 | | | 0 | 3 | 3 | 3 | | 3 | 3 | 3 | 3 | 0 | 3 | 3 | 3 | 3 | 3 | 3 | 3 | 3 |
| | 1.1210 | 0 | | | 0 | 3 | 2 | 2 | | 2 | 2 | 3 | 3 | 0 | 2 | 3 | 3 | 3 | 3 | 3 | 3 | 3 |
| | 0.5605 | 0 | | | 0 | 3 | 3 | 3 | | 2 | 2 | 0 | 3 | 0 | 3 | 3 | 3 | 3 | 3 | 3 | 3 | 3 |
| | 0.2803 | 0 | | | 0 | 2 | 2 | 3 | | 2 | 0 | 2 | 3 | 0 | 2 | 3 | 3 | 3 | 3 | 3 | 3 | 3 |
| | 0.1401 | 0 | | | 0 | 2 | 0 | 3 | | 2 | 0 | 2 | 3 | 0 | 2 | 3 | 3 | 3 | 3 | 2 | 2 | 2 |
| 49 | 0.0701 | 0 | | | 0 | 0 | 0 | 0 | | 0 | 0 | 0 | 0 | 0 | 0 | 0 | 0 | 0 | 0 | 0 | 0 | 0 |
| | 0.0350 | 0 | | | 0 | 0 | 0 | 0 | | 0 | 0 | 0 | 0 | 0 | 0 | 0 | 0 | 0 | 0 | 0 | 0 | 0 |
| | 0.0175 | 0 | | | 0 | 0 | 0 | 0 | | 0 | 0 | 0 | 0 | 0 | 0 | 0 | 0 | 0 | 0 | 0 | 0 | 0 |
| 50 | 5.6050 | 3 | | | 2 | 3 | 3 | 3 | | 3 | 3 | 3 | 3 | 3 | 3 | 3 | 3 | 3 | 3 | 3 | 3 | 3 |
| | 1.1210 | 0 | | | 0 | 3 | 3 | 3 | | 2 | 2 | 2 | 3 | 0 | 2 | 3 | 3 | 3 | 3 | 1 | 3 | 3 |
| | 0.5605 | 0 | | | 0 | 0 | 0 | 0 | | 0 | 0 | 0 | 2 | 0 | 2 | 2 | 2 | 3 | 2 | 0 | 3 | 3 |
| | 0.2803 | 0 | | | 0 | 0 | 0 | 0 | | 0 | 0 | 0 | 0 | 0 | 0 | 1 | 1 | 0 | 0 | 0 | 0 | 1 |
| | 0.1401 | 0 | | | 0 | 0 | 0 | 0 | | 0 | 0 | 0 | 0 | 0 | 0 | 0 | 0 | 0 | 0 | 0 | 0 | 0 |
| 50 | 0.0701 | 0 | | | 0 | 0 | 0 | 0 | | 0 | 0 | 0 | 0 | 0 | 0 | 0 | 0 | 0 | 0 | 0 | 0 | 0 |
| | 0.0350 | 0 | | | 0 | 0 | 0 | 0 | | 0 | 0 | 0 | 0 | 0 | 0 | 0 | 0 | 0 | 0 | 0 | 0 | 0 |
| | 0.0175 | 0 | | | 0 | 0 | 0 | 0 | | 0 | 0 | 0 | 0 | 0 | 0 | 0 | 0 | 0 | 0 | 0 | 0 | 0 |
| 51 | 5.6050 | 3 | | | 0 | 3 | 3 | 3 | | 3 | 3 | 3 | 3 | 3 | 3 | 3 | 3 | 3 | 3 | 3 | 3 | 3 |
| | 1.1210 | 2 | | | 1 | 3 | 3 | 3 | | 2 | 3 | 3 | 3 | 1 | 2 | 3 | 3 | 3 | 3 | 3 | 3 | 3 |
| | 0.5605 | 0 | | | 1 | 2 | 2 | 2 | | 2 | 0 | 2 | 3 | 1 | 2 | 3 | 3 | 3 | 3 | 0 | 0 | 0 |
| | 0.2803 | 0 | | | 0 | 0 | 0 | 0 | | 0 | 0 | 2 | 3 | 0 | 2 | 2 | 2 | 3 | 3 | 0 | 0 | 0 |
| | 0.1401 | 0 | | | 0 | 0 | 0 | 0 | | 0 | 0 | 2 | 3 | 0 | 2 | 2 | 2 | 2 | 3 | 0 | 0 | 0 |
| | 0.0701 | 0 | | | 0 | 0 | 0 | 0 | | 0 | 0 | 1 | 3 | 0 | 0 | 0 | 0 | 0 | 2 | 0 | 0 | 0 |
| | 0.0350 | 0 | | | 0 | 0 | 0 | 0 | | 0 | 0 | 0 | Z | 0 | 0 | 0 | 0 | 0 | 0 | 0 | 0 | 0 |
| | 0.0175 | 0 | | | 0 | 0 | 0 | 0 | | 0 | 0 | 0 | Z | 0 | 0 | 0 | 0 | 0 | 0 | 0 | 0 | 0 |
| 51 | 0.0087 | 0 | | | 0 | 0 | 0 | 0 | | 0 | 0 | 0 | Z | 0 | 0 | 0 | 0 | 0 | 0 | 0 | 0 | 0 |
| 52 | 5.6050 | 3 | | | 0 | 3 | 3 | 3 | | 3 | 3 | 3 | 3 | 3 | 3 | 3 | 3 | 3 | 3 | 3 | 2 | 3 |
| | 1.1210 | 2 | | | 0 | 3 | 2 | 2 | | 2 | 3 | 3 | 3 | 2 | 2 | 3 | 3 | 3 | 3 | 2 | 2 | 2 |
| | 0.5605 | 0 | | | 0 | 3 | 2 | 1 | | 1 | 0 | 3 | 3 | 1 | 3 | 3 | 3 | 3 | 3 | 1 | 3 | 2 |
| | 0.2803 | 1 | | | 0 | 2 | 1 | 0 | | 2 | 0 | 3 | 2 | 1 | 3 | 3 | 3 | 3 | 3 | 1 | 1 | 1 |

TABLE B-continued

TABLE B-continued

| Ex. No. | Rate kg/ha | Sobe | Cotz | Rape | Cobu | Wibw | Mogl | Hese | Jiwe | Vele | Whez | Rice | Grso | Corn | Dobr | Prmi | Bygr | Lacg | Grft | Sube | Colq | Pesw |
|---|---|---|---|---|---|---|---|---|---|---|---|---|---|---|---|---|---|---|---|---|---|---|
| 59 | 0.0175 | 0 | | | 0 | 0 | 0 | 0 | | 0 | 0 | 0 | 0 | 0 | 0 | 0 | 0 | 0 | 0 | 1 | N | 0 |
| | 5.6050 | 3 | | | 2 | 3 | 3 | 3 | | 3 | 3 | 3 | 3 | 3 | 3 | 3 | 3 | 3 | 3 | 3 | 3 | 3 |
| | 1.1210 | 1 | | | 0 | 3 | 1 | 3 | | 3 | 2 | 3 | 3 | 2 | 3 | 3 | 3 | 3 | 3 | 3 | 3 | 3 |
| | 0.5605 | 0 | | | 0 | 2 | 3 | 2 | | 3 | 1 | 3 | 2 | 1 | 2 | 2 | 3 | 3 | 3 | 3 | 3 | 3 |
| | 0.2803 | 0 | | | 0 | 1 | 0 | 1 | | 0 | 0 | 2 | 1 | 0 | 2 | 2 | 2 | 2 | 3 | 2 | 3 | 3 |
| | 0.1401 | 0 | | | 0 | 0 | 0 | 0 | | 0 | 0 | 0 | 0 | 0 | 0 | 2 | 0 | 1 | 2 | 0 | 3 | 3 |
| | 0.0701 | 0 | | | 0 | 0 | 0 | 0 | | 0 | 0 | 0 | 0 | 0 | 0 | 2 | 0 | 3 | 3 | 0 | 3 | 3 |
| | 0.0350 | 0 | | | 0 | N | 0 | 0 | | 0 | 0 | 0 | 0 | 0 | 0 | 2 | 0 | 3 | 3 | 2 | 3 | 1 |
| | 0.0175 | 0 | | | 0 | 0 | 0 | 0 | | 0 | 0 | 0 | 0 | 0 | 0 | 0 | 0 | 3 | 3 | 0 | 0 | 0 |
| | 0.0087 | 0 | | | 0 | 0 | 0 | 0 | | 0 | 0 | 0 | 0 | 0 | 0 | 0 | 0 | 3 | 3 | 0 | 3 | 3 |
| 59 | 0.1401 | 0 | | | 0 | 0 | 0 | 0 | | 0 | 0 | 0 | 0 | 0 | 0 | 0 | 0 | 2 | 2 | 0 | 3 | 3 |
| | 0.0701 | 0 | | | 0 | 2 | 0 | 3 | | 3 | 3 | 3 | 3 | 3 | 3 | 2 | 3 | 3 | 3 | 3 | 3 | 3 |
| | 0.0350 | 0 | | | 0 | 1 | 3 | 3 | | 3 | 2 | 3 | 3 | 1 | 2 | 3 | 3 | 3 | 3 | 3 | 3 | 3 |
| | 0.0175 | 0 | | | 0 | 0 | 1 | 1 | | 2 | 1 | 2 | 3 | 0 | 2 | 2 | 3 | 3 | 3 | 2 | 3 | 3 |
| | 0.0087 | 0 | | | 0 | 0 | 0 | 0 | | 0 | 0 | 0 | 0 | 0 | 0 | 0 | 2 | 2 | 2 | 0 | 3 | 3 |
| 60 | 5.6050 | 3 | | | 0 | 3 | 3 | 3 | | 3 | 3 | 3 | 3 | 3 | 3 | 3 | 3 | 3 | 3 | 3 | 3 | 3 |
| | 1.1210 | 2 | | | 0 | 2 | 3 | 3 | | 2 | 2 | 2 | 3 | 0 | 2 | 2 | 3 | 3 | 3 | 2 | 3 | 3 |
| | 0.5605 | 0 | | | 0 | 1 | 1 | 1 | | 2 | 1 | 2 | 3 | 1 | 2 | 2 | 3 | 3 | 3 | 2 | 3 | 3 |
| | 0.2803 | 0 | | | 0 | 0 | 0 | 0 | | 0 | 0 | 0 | 0 | 0 | 0 | 0 | 0 | 2 | 2 | 0 | 2 | 2 |
| | 0.1401 | 0 | | | 0 | 0 | 0 | 0 | | 0 | 0 | 0 | 0 | 0 | 0 | 0 | 0 | 3 | 3 | 0 | 0 | 1 |
| | 0.0701 | 0 | | | 0 | N | 0 | 0 | | 0 | 0 | 0 | 0 | 0 | 0 | 0 | 0 | 0 | 0 | 0 | 0 | 0 |
| | 0.0350 | 0 | | | 0 | 0 | 0 | 0 | | 0 | 0 | 0 | 0 | 0 | 0 | 0 | 0 | 0 | 0 | 0 | 0 | 0 |
| | 0.0175 | 0 | | | 0 | N | 0 | 0 | | 0 | 0 | 0 | 0 | 0 | 0 | 0 | 0 | 0 | 0 | 0 | 0 | 0 |
| | 0.0087 | 0 | | | 0 | 0 | 0 | 0 | | 0 | 0 | 0 | 0 | 0 | 0 | 0 | 0 | 0 | 0 | 0 | 0 | 0 |
| 61 | 5.6050 | 0 | | | 0 | 2 | 0 | 0 | | 3 | 3 | 2 | 3 | 2 | 3 | 3 | 3 | 3 | 3 | 3 | 3 | 3 |
| | 1.1210 | 3 | | | 0 | 1 | 0 | 0 | | 3 | 3 | 2 | 3 | 0 | 2 | 2 | 3 | 3 | 3 | 2 | 3 | 2 |
| | 0.5605 | 2 | | | 0 | 1 | 0 | 0 | | 2 | 2 | 2 | 2 | 0 | 2 | 2 | 3 | 3 | 3 | 2 | 3 | 0 |
| | 0.2803 | 0 | | | 0 | 0 | 0 | 0 | | 2 | 0 | 2 | 2 | 0 | 1 | 0 | 3 | 3 | 2 | 2 | 2 | 1 |
| 62 | 5.6050 | 3 | | | 2 | 3 | 3 | 3 | | 3 | 3 | 3 | 3 | 3 | 3 | 3 | 3 | 3 | 3 | 3 | 3 | 3 |
| | 1.1210 | 1 | | | 0 | 2 | 2 | 3 | | 2 | 3 | 2 | 3 | 1 | 2 | 3 | 3 | 3 | 3 | 3 | 3 | 3 |
| | 0.5605 | 0 | | | 0 | 1 | 0 | 0 | | 0 | 0 | 2 | 2 | 0 | 1 | 2 | 3 | 3 | 3 | 1 | 0 | 1 |
| | 0.2803 | 0 | | | 0 | 1 | 0 | 0 | | 0 | 0 | 1 | 2 | 0 | 1 | 1 | 1 | 2 | 2 | 1 | 0 | 0 |
| | 0.1401 | 0 | | | 0 | 1 | 0 | 0 | | 0 | 0 | 1 | 2 | 0 | 0 | 0 | 0 | 0 | 0 | 0 | 0 | 0 |
| | 0.0701 | 0 | | | 0 | 1 | 0 | 0 | | 0 | 0 | 1 | 1 | 0 | 0 | 0 | 0 | 0 | 1 | 0 | 0 | 0 |
| | 0.0350 | 0 | | | 0 | 0 | 0 | 0 | | 0 | 0 | 0 | 0 | 0 | 0 | 0 | 0 | 0 | 0 | 0 | 0 | 0 |
| | 0.0175 | 0 | | | 0 | 2 | 0 | 0 | | 0 | 0 | 0 | 0 | 0 | 0 | 0 | 0 | 0 | 0 | 0 | 0 | 0 |
| | 0.0087 | 0 | | | 0 | 0 | 0 | 0 | | 0 | 0 | 0 | 0 | 0 | 0 | 0 | 0 | 0 | 0 | 0 | 0 | 0 |
| 63 | 5.6050 | 0 | | | 0 | 0 | 0 | 0 | | 0 | 0 | 0 | 0 | 0 | 0 | 0 | 0 | 0 | 0 | 0 | 0 | 0 |
| | 1.1210 | 0 | | | 0 | 0 | 0 | 0 | | 0 | 0 | 0 | 0 | 0 | 0 | 0 | 0 | 0 | 0 | 0 | 0 | 0 |
| 63 | 0.5605 | 0 | | | 0 | 0 | 0 | 0 | | 0 | 0 | 0 | 0 | 0 | 0 | 0 | 0 | 0 | 0 | 0 | 0 | 0 |
| | 0.2803 | 0 | | | 0 | 0 | 0 | 0 | | 0 | 0 | 0 | 0 | 0 | 0 | 0 | 0 | 0 | 0 | 0 | 0 | 0 |
| | 0.1401 | 0 | | | 0 | 0 | 0 | 0 | | 0 | 0 | 0 | 0 | 0 | 0 | 0 | 0 | 0 | 0 | 0 | 0 | 0 |
| | 0.0701 | 0 | | | 0 | 0 | 0 | 0 | | 0 | 0 | 0 | 0 | 0 | 0 | 0 | 0 | 0 | 0 | 0 | 0 | 0 |
| | 0.0350 | 0 | | | 0 | 0 | 0 | 0 | | 0 | 0 | 0 | 0 | 0 | 0 | 0 | 0 | 0 | 0 | 0 | 0 | 0 |
| | 0.0175 | 0 | | | 0 | 0 | 0 | 0 | | 0 | 0 | 0 | 0 | 0 | 0 | 0 | 0 | 0 | 0 | 0 | 0 | 0 |
| 64 | 5.6050 | 3 | | | 3 | 3 | 3 | 3 | | 3 | 3 | 3 | 3 | 3 | 3 | 3 | 3 | 3 | 3 | 3 | 3 | 3 |
| | 1.1210 | 2 | | | 0 | 3 | 3 | 3 | | 3 | 2 | 3 | 3 | 3 | 3 | 3 | 3 | 3 | 3 | 2 | 3 | 2 |
| | 0.5605 | 2 | | | 0 | 3 | 3 | 2 | | 2 | 3 | 3 | 3 | 2 | 3 | 3 | 3 | 3 | 3 | 2 | 2 | 2 |
| | 0.2803 | 1 | | | 0 | 1 | 1 | 0 | | 0 | 0 | 2 | 1 | 0 | 2 | 3 | 3 | 2 | 3 | 1 | 1 | 1 |
| 64 | 0.1401 | 0 | | | 0 | 0 | 0 | 0 | | 0 | 0 | 1 | 1 | 0 | 2 | 3 | 3 | 3 | 3 | 0 | 0 | 0 |
| | 0.0701 | 0 | | | 0 | 0 | 0 | 0 | | 0 | 0 | 0 | 0 | 0 | 2 | 3 | 3 | 3 | 3 | 0 | 0 | 0 |
| | 0.0350 | 0 | | | 0 | N | 0 | 0 | | 0 | 0 | 0 | 0 | 0 | 2 | 3 | 2 | 3 | 3 | N | N | 2 |

TABLE B-continued

| Ex. No. | Rate kg/ha | Sobe | Cotz | Rape | Cobu | Wibw | Mogl | Hese | Jiwe | Vele | Whez | Rice | Grso | Corn | Dobr | Prmi | Bygr | Lacg | Grft | Sube | Colq | Pesw |
|---|---|---|---|---|---|---|---|---|---|---|---|---|---|---|---|---|---|---|---|---|---|---|
| 65 | 0.0175 | 0 | | | 0 | 0 | 0 | 0 | | 0 | 0 | 0 | 0 | 0 | 0 | | 0 | 0 | 0 | 0 | 0 | 2 |
| | 5.6050 | 3 | | | 2 | 3 | 3 | 3 | | 3 | 3 | 3 | 3 | 3 | 3 | 1 | 3 | 3 | 3 | 3 | 3 | 3 |
| | 1.1210 | 0 | | | 0 | 3 | 2 | 0 | | 3 | 2 | 3 | 3 | — | 3 | 3 | 3 | 3 | 3 | 2 | 3 | 3 |
| | 0.5605 | 0 | | | 0 | 0 | 0 | 0 | | 2 | 0 | — | 0 | 0 | — | 3 | 3 | 3 | 3 | 0 | 3 | 3 |
| | 0.2803 | 0 | | | 0 | 0 | 0 | 0 | | 0 | 0 | 0 | 0 | 0 | 0 | 3 | 2 | 3 | 2 | 0 | 2 | 2 |
| | 0.1401 | 0 | | | 0 | 0 | 0 | 0 | | 0 | 0 | 0 | 0 | 0 | 0 | 2 | 0 | 2 | 0 | 0 | 0 | 0 |
| | 0.0701 | 0 | | | 0 | 0 | 0 | 0 | | 0 | 0 | 0 | 0 | 0 | 0 | 0 | 0 | 0 | 0 | 0 | 0 | 0 |
| | 0.0350 | 0 | | | 0 | 0 | 0 | 0 | | 0 | 0 | 0 | 0 | 0 | 0 | 0 | 0 | 0 | 0 | 0 | 0 | 0 |
| 66 | 5.6050 | 3 | | | 3 | 3 | 3 | 3 | | 3 | 3 | 3 | 3 | 3 | 3 | 3 | 3 | 3 | 3 | 3 | 3 | 3 |
| | 1.1210 | — | | | — | 3 | 3 | 3 | | 3 | 3 | 3 | 3 | 3 | 3 | 3 | 3 | 3 | 3 | 3 | 3 | 3 |
| | 0.5605 | 2 | | | 0 | 3 | 2 | 2 | | 2 | 3 | 3 | 3 | 3 | 3 | 3 | 3 | 3 | 3 | 3 | 3 | 3 |
| | 0.2803 | — | | | — | 3 | Z | 2 | | 2 | 3 | 3 | 2 | — | — | 3 | 3 | 3 | 3 | 3 | 3 | 3 |
| | 0.1401 | 0 | | | 0 | 3 | — | 0 | | 2 | 3 | 3 | — | 0 | 0 | 2 | 3 | 3 | 3 | Z | 2 | 2 |
| | 0.0701 | 0 | | | 0 | 0 | 0 | 0 | | 2 | — | 2 | 0 | 0 | 0 | 0 | 2 | 3 | 3 | 3 | 3 | 3 |
| | 0.0350 | 0 | | | — | 3 | — | 3 | | 0 | 3 | 3 | 0 | 0 | — | 0 | 3 | 3 | 3 | 0 | 3 | 3 |
| | 0.0175 | 0 | | | 0 | 3 | 2 | 2 | | 0 | 3 | 3 | — | 0 | — | 0 | 3 | 3 | 3 | 0 | 3 | 3 |
| | 0.0087 | 0 | | | — | 2 | — | 2 | | — | 2 | 2 | — | 0 | 2 | 0 | 2 | 2 | 2 | 0 | 2 | 2 |
| 67 | 5.6050 | 3 | | | 0 | 0 | 0 | 0 | | 0 | 0 | 0 | 0 | 0 | 0 | 0 | 0 | 0 | 0 | 0 | 0 | 0 |
| | 1.1210 | 0 | | | 0 | 3 | 3 | 3 | | 3 | 3 | 3 | 3 | 3 | 3 | 3 | 3 | 3 | 3 | 3 | 3 | 3 |
| | 0.5605 | 0 | | | 0 | 3 | 2 | 0 | | — | 3 | 3 | — | 2 | 2 | 3 | 3 | 3 | 3 | 3 | 3 | 3 |
| | 0.2803 | 0 | | | 0 | 2 | — | 0 | | 0 | 2 | 2 | 0 | 0 | — | 0 | 2 | 2 | 2 | 2 | 2 | 2 |
| | 0.1401 | 0 | | | 0 | 0 | 0 | 0 | | 0 | 0 | 0 | 0 | 0 | 0 | 0 | 0 | 0 | 0 | 0 | 0 | — |
| | 0.0701 | 0 | | | 0 | 0 | 0 | 0 | | 0 | 0 | 0 | 0 | 0 | 0 | 0 | 0 | 0 | 0 | 0 | 0 | — |
| 68 | 5.6050 | 0 | | | 0 | 3 | 0 | 0 | | 0 | 0 | 0 | 0 | 0 | 0 | 0 | 0 | 0 | 0 | 0 | 0 | 0 |
| | 1.1210 | 0 | | | 0 | — | 2 | 0 | | — | 3 | 0 | 0 | 0 | 0 | 3 | 3 | 3 | 3 | 0 | 3 | 3 |
| | 0.5605 | 0 | | | 0 | 0 | 0 | 0 | | 0 | 0 | 0 | 0 | 0 | 0 | — | 2 | 2 | — | 0 | — | — |
| | 0.2803 | 0 | | | 0 | 0 | 0 | 0 | | 0 | 0 | 0 | 0 | 0 | 0 | 0 | 0 | 0 | 0 | 0 | 0 | 0 |
| | 0.1401 | 0 | | | 0 | 0 | 0 | 0 | | 0 | 0 | 0 | 0 | 0 | — | 0 | 0 | 0 | 0 | 0 | 0 | 0 |
| | 0.0701 | 0 | | | 0 | 0 | 0 | 0 | | 0 | 0 | 0 | 0 | 0 | 0 | 0 | 0 | 0 | 0 | 0 | 0 | 0 |
| 69 | 5.6050 | 2 | | | 2 | 2 | 3 | 3 | | 3 | 3 | 3 | 3 | 2 | 3 | 3 | 3 | 3 | 3 | 2 | 3 | 3 |
| | 1.1210 | 0 | | | — | 2 | 0 | — | | — | 2 | 2 | — | 0 | 2 | — | 2 | 2 | 2 | 0 | — | — |
| | 0.5605 | 0 | | | 0 | 0 | 0 | 0 | | 0 | 0 | 0 | 0 | 0 | — | 0 | — | — | — | 0 | — | 0 |
| | 0.2803 | 0 | | | 0 | 0 | 0 | 0 | | 0 | 0 | 0 | 0 | 0 | 0 | 0 | 0 | 0 | 0 | 0 | 0 | 0 |
| | 0.1401 | 0 | | | 0 | Z | 0 | 0 | | 0 | 0 | 0 | 0 | 0 | 0 | 0 | 0 | 0 | 0 | Z | 0 | — |
| | 0.0701 | 0 | | | 0 | 0 | 0 | 0 | | 0 | 0 | 0 | 0 | 0 | 0 | 0 | 0 | 0 | 0 | 0 | 0 | 0 |
| 70 | 5.6050 | 3 | | | 2 | 3 | 3 | 3 | | 3 | 3 | 3 | 3 | 3 | 3 | 3 | 3 | 3 | 3 | 3 | 3 | 3 |
| | 1.1210 | 0 | | | 0 | 3 | 0 | 0 | | — | 0 | 0 | — | — | — | — | 3 | 3 | 2 | 3 | 3 | — |
| | 0.5605 | 0 | | | 0 | 0 | 0 | 0 | | 0 | 0 | 0 | 0 | 0 | 0 | 0 | 0 | 0 | 0 | 0 | 0 | 0 |
| | 0.2803 | 0 | | | 0 | 0 | 0 | 0 | | 0 | 0 | 0 | 0 | 0 | 0 | 0 | 0 | 0 | 0 | 0 | 0 | 0 |
| | 0.1401 | 0 | | | 0 | 0 | 0 | 0 | | 0 | 0 | 0 | 0 | 0 | 0 | 0 | 0 | 0 | 0 | 0 | 0 | 0 |
| | 0.0701 | 0 | | | 0 | 0 | 0 | 0 | | 0 | 0 | 0 | 0 | 0 | 0 | 0 | 0 | 0 | 0 | 0 | 0 | 0 |
| | 0.0350 | 0 | | | 0 | 0 | 0 | 0 | | 0 | 0 | 0 | 0 | 0 | 0 | 0 | 0 | 0 | 0 | 0 | 0 | 0 |
| | 0.0175 | 0 | | | 0 | 0 | 0 | 0 | | 0 | 0 | 0 | 0 | 0 | 0 | 0 | 0 | 0 | 0 | 0 | 0 | 0 |
| | 0.1075 | 0 | | | 0 | 0 | 0 | 0 | | 0 | 0 | 0 | 0 | 0 | 0 | 0 | 0 | 0 | 0 | 0 | 0 | 0 |
| 71 | 5.6050 | 3 | | | 2 | 3 | 3 | 3 | | 3 | 3 | 3 | 3 | 3 | 3 | 3 | 3 | 3 | 3 | 3 | 3 | 3 |
| | 1.1210 | 0 | | | 3 | 3 | 2 | — | | 2 | 3 | 3 | 2 | 2 | 3 | 3 | 3 | 3 | 3 | 2 | 3 | 3 |
| | 0.5605 | 0 | | | 0 | 0 | — | — | | 2 | — | 3 | 0 | 3 | 2 | 3 | 3 | 3 | 3 | 2 | 3 | 3 |
| | 0.2803 | 0 | | | 0 | 0 | — | — | | 2 | 0 | 3 | 2 | 0 | 2 | 3 | 3 | 3 | 3 | — | 2 | 3 |

TABLE B-continued

| Ex. No. | Rate kg/ha | Sobe | Cotz | Rape | Cobu | Wibw | Mogl | Hese | Jiwe | Vele | Whez | Rice | Grso | Corn | Dobr | Prmi | Bygr | Lacg | Grft | Sube | Colq | Pesw |
|---|---|---|---|---|---|---|---|---|---|---|---|---|---|---|---|---|---|---|---|---|---|---|
| | 0.1401 | 0 | | | 0 | 0 | 0 | 0 | | 2 | | 2 | 3 | 0 | 1 | 3 | 3 | 3 | 3 | 1 | 1 | 1 |
| | 0.0701 | 0 | | | 0 | 0 | 1 | 1 | | 0 | 1 | 1 | 2 | 0 | 0 | 0 | 2 | 3 | 2 | 0 | 0 | N |
| | 0.0350 | 0 | | | 1 | 0 | 0 | 0 | | 0 | 0 | 0 | 0 | 0 | 0 | 0 | 0 | 0 | 1 | 0 | 0 | 0 |
| | 0.0175 | 0 | | | 0 | 0 | 0 | 0 | | 0 | 0 | 0 | 0 | 0 | 0 | 0 | 0 | 0 | 0 | 0 | 0 | 0 |
| | 0.0087 | 0 | | | 0 | 0 | 0 | 0 | | 0 | 0 | 0 | 0 | 0 | 0 | 0 | 0 | 0 | 0 | 0 | 0 | 0 |
| 72 | 5.6050 | 3 | | | 3 | 3 | 3 | 3 | | 3 | 3 | 3 | 3 | 3 | 3 | 3 | 3 | 3 | 3 | 3 | 3 | 3 |
| | 1.1210 | 3 | | | 2 | 3 | 3 | 3 | | 3 | 3 | 3 | 3 | 3 | 3 | 3 | 3 | 3 | 3 | 3 | 3 | 3 |
| | 0.5605 | 2 | | | 0 | 2 | 2 | 3 | | 2 | 3 | 3 | 3 | 3 | 3 | 3 | 3 | 3 | 2 | 3 | 3 | 3 |
| | 0.2803 | 0 | | | 0 | 2 | 1 | 1 | | 2 | 2 | 3 | 3 | 0 | 3 | 3 | 2 | 2 | 2 | 1 | 2 | 1 |
| | 0.1401 | 0 | | | 0 | 0 | 0 | 2 | | 2 | 2 | 3 | 3 | 0 | 3 | 3 | 1 | 1 | 1 | 0 | 1 | 1 |
| | 0.0701 | 0 | | | 0 | 0 | 0 | 1 | | 0 | 0 | 3 | 3 | 0 | 1 | 0 | 1 | 0 | 0 | 0 | 0 | 1 |
| | 0.0350 | 0 | | | 0 | 0 | 0 | 0 | | 0 | 0 | 0 | 0 | 0 | 0 | 0 | 0 | 0 | 0 | 0 | 0 | 0 |
| | 0.0175 | 0 | | | 0 | 0 | 0 | 0 | | 0 | 0 | 0 | 0 | 0 | 0 | 0 | 0 | 0 | 0 | 0 | 0 | 0 |
| | 0.0087 | 0 | | | 0 | 0 | 0 | 0 | | 0 | 0 | 0 | 0 | 0 | 0 | 0 | 0 | 0 | 0 | 0 | 0 | 0 |
| 73 | 11.2100 | 0 | | | 0 | 0 | 0 | 0 | | 0 | 0 | 0 | 0 | 0 | 0 | 0 | 0 | 0 | 0 | 0 | 0 | 0 |
| | 5.6050 | 0 | | | 0 | 0 | 0 | 0 | | 0 | 0 | 0 | 0 | 0 | 0 | 0 | 0 | 0 | 0 | 0 | 0 | 0 |
| | 2.8025 | 0 | | | 0 | 0 | 0 | 0 | | 0 | 0 | 0 | 0 | 0 | 0 | 0 | 0 | 0 | 0 | 0 | 0 | 0 |
| | 1.1210 | 1 | | | 0 | 0 | 0 | 0 | | 0 | 0 | 0 | 0 | 0 | 0 | 0 | 0 | 0 | 0 | 0 | 0 | 0 |
| 77 | 5.6050 | 0 | | | 0 | 0 | 0 | 0 | | 0 | 0 | 0 | N | 0 | 3 | 3 | 3 | 3 | 3 | N | 3 | 3 |
| | 1.1210 | 0 | | | 0 | 0 | 0 | 2 | | 3 | 3 | 3 | 3 | 0 | 3 | 3 | 3 | 3 | 3 | 3 | 3 | 3 |
| | 0.5605 | 3 | | | 0 | 3 | 2 | 2 | | 2 | 0 | 3 | 2 | 0 | 3 | 3 | 3 | 3 | 3 | 3 | 3 | 3 |
| | 0.2803 | 3 | | | 0 | 3 | 0 | 2 | | 2 | 0 | 3 | 1 | 0 | 3 | 3 | 3 | 2 | 3 | 3 | 3 | 1 |
| | 0.1401 | 2 | | | 0 | 3 | 1 | 2 | | 1 | 0 | 3 | 2 | 0 | 3 | 3 | 3 | 2 | 2 | 1 | 3 | 1 |
| | 0.0701 | 3 | | | 0 | 1 | 3 | 2 | | 3 | 1 | 3 | 1 | 0 | 3 | 3 | 3 | 3 | 3 | 3 | 3 | 1 |
| 77 | 5.6050 | 1 | | | 0 | 3 | 2 | 1 | | 3 | 3 | 3 | 2 | 3 | 3 | 3 | 3 | 3 | 3 | 3 | 3 | 1 |
| 78 | 1.1210 | 1 | | | 1 | 3 | 3 | 1 | | 2 | 2 | 2 | 3 | 2 | 3 | 3 | 3 | 3 | 3 | 3 | 3 | 1 |
| | 0.5605 | 2 | | | 1 | 0 | 2 | N | | 0 | 0 | 0 | Z | 0 | 0 | 2 | 2 | 2 | 2 | 2 | 3 | 1 |
| | 0.2803 | 3 | | | N | Z | 3 | 1 | | 0 | 0 | 1 | N | 0 | N | 0 | 0 | 0 | 0 | N | N | 1 |
| | 0.1401 | 1 | | | 0 | 0 | 3 | 0 | | 0 | 0 | 3 | 3 | 0 | 3 | 3 | 3 | 0 | 0 | 0 | 0 | 0 |
| | 0.0701 | 0 | | | 0 | 2 | 0 | 0 | | 0 | 0 | 1 | 0 | 0 | 2 | 0 | 0 | 0 | 0 | 0 | 0 | 0 |
| | 0.0350 | 0 | | | 0 | 0 | 0 | 0 | | 0 | 0 | 0 | 0 | 0 | 0 | 0 | 0 | 0 | 0 | 0 | 0 | 0 |
| | 0.0175 | 0 | | | 0 | 0 | 0 | 0 | | 0 | 0 | 0 | 0 | 0 | 0 | 0 | 0 | 0 | 0 | 0 | 0 | 0 |
| | 0.0087 | 0 | | | 0 | 0 | 0 | 0 | | 0 | 0 | 0 | 0 | 0 | 0 | 0 | 0 | 0 | 0 | 0 | 0 | 0 |
| 78 | 5.6050 | 2 | | | 2 | 3 | 3 | 3 | | 3 | 3 | 3 | 3 | 3 | 3 | 3 | 3 | 3 | 3 | 3 | 3 | 3 |
| 79 | 1.1210 | 2 | | | 3 | 3 | 3 | 3 | | 3 | 3 | 3 | 3 | 3 | 3 | 3 | 3 | 3 | 3 | 3 | 3 | 3 |
| | 0.5605 | 3 | | | 3 | 3 | 3 | 2 | | 3 | 3 | 3 | 3 | 3 | 3 | 3 | 3 | 3 | 3 | 3 | 3 | 3 |
| | 0.2803 | 2 | | | 3 | 3 | 2 | 2 | | 3 | 2 | 3 | 0 | 2 | 3 | 2 | 3 | 3 | 3 | 3 | 3 | 3 |
| | 0.1401 | 0 | | | 2 | 3 | 3 | 2 | | 3 | 2 | 3 | 0 | 1 | 2 | 2 | 3 | 3 | 3 | 3 | 3 | 2 |
| | 0.0701 | 0 | | | 0 | 3 | 1 | 2 | | 3 | 2 | 2 | 0 | 1 | 2 | 1 | 3 | 3 | 3 | 2 | 3 | 1 |
| | 0.0350 | 0 | | | 0 | 3 | 1 | 0 | | 1 | 0 | 0 | 0 | 0 | 2 | 0 | 0 | 3 | 1 | 1 | 3 | 0 |
| | 0.0175 | 0 | | | 0 | 0 | 1 | 0 | | 0 | 0 | 0 | 0 | 0 | 0 | 0 | 0 | 2 | 0 | 0 | 3 | 0 |
| 80 | 5.6050 | 3 | | | 2 | 3 | 3 | 3 | | 3 | 3 | 3 | 3 | 3 | 3 | 3 | 3 | 3 | 3 | 3 | 3 | 3 |
| | 1.1210 | 3 | | | N | 3 | 2 | 2 | | 3 | 2 | 3 | 3 | 3 | 3 | 3 | 3 | 2 | 3 | 2 | 2 | 2 |
| | 0.5605 | 2 | | | 0 | 3 | 1 | 0 | | 3 | 2 | 3 | 3 | 2 | 2 | 3 | 3 | Z | 3 | 2 | N | 1 |
| | 0.2803 | 0 | | | Z | 3 | 1 | 0 | | 3 | 0 | 3 | 3 | 1 | 2 | 3 | 0 | 0 | 3 | 1 | 2 | 0 |
| | 0.1401 | 0 | | | 0 | 3 | 1 | 0 | | 3 | 0 | 3 | 2 | 1 | Z | 3 | 0 | 0 | 3 | 0 | 0 | 0 |
| | 0.0701 | 0 | | | 0 | 3 | 0 | 0 | | 3 | 0 | 2 | 1 | 0 | 3 | 2 | 0 | 0 | 3 | 2 | 0 | 0 |
| | 0.0350 | 0 | | | 0 | 3 | 0 | 0 | | 0 | 0 | 0 | 0 | 0 | 2 | 0 | 0 | 0 | 3 | 1 | 0 | 0 |
| | 0.0175 | 0 | | | 0 | 1 | 1 | 0 | | 0 | 0 | 0 | 0 | 0 | Z | 0 | 0 | 0 | 0 | 0 | 2 | 0 |
| | 0.0087 | 0 | | | 0 | 1 | 1 | 0 | | 0 | 0 | 0 | 0 | 0 | 0 | 0 | 0 | 0 | 0 | 2 | N | 0 |
| 81 | 5.6050 | 3 | | | 0 | 3 | 3 | 3 | | 3 | 2 | 3 | 3 | 3 | 3 | 3 | 3 | 3 | 3 | 3 | 3 | 3 |

TABLE B-continued

| Ex. No. | Rate kg/ha | Sobe | Cotz | Rape | Cobu | Wibw | Mogl | Hese | Jiwe | Vele | Whez | Rice | Grso | Corn | Dobr | Prmi | Bygr | Lacg | Grft | Sube | Colq | Pesw |
|---|---|---|---|---|---|---|---|---|---|---|---|---|---|---|---|---|---|---|---|---|---|---|
| | 1.1210 | 1 | | | N | 0 | 2 | 1 | | 0 | 0 | 3 | 3 | 3 | 2 | 3 | 3 | 3 | 3 | 1 | 2 | 2 |
| | 0.5605 | N | | | N | 0 | N | 1 | | 1 | 0 | 3 | 3 | 0 | 1 | 3 | 3 | 3 | 0 | 0 | 0 | 1 |
| | 0.2803 | 0 | | | 0 | 0 | N | 0 | | 0 | 0 | 2 | 1 | 0 | 0 | 0 | 2 | 3 | 0 | N | 0 | N |
| | 0.1401 | 0 | | | 1 | 0 | N | N | | N | 0 | 2 | 0 | 0 | 0 | N | 0 | 2 | 0 | 0 | 0 | 2 |
| | 0.0701 | 0 | | | N | 0 | 0 | 0 | | 0 | 0 | 0 | 0 | 0 | 0 | 0 | 0 | 1 | 0 | 0 | 0 | 3 |
| | 0.0350 | N | | | 0 | 0 | 0 | 0 | | 0 | 0 | 0 | 0 | 0 | 0 | 0 | 0 | 0 | 0 | 0 | 0 | 1 |
| | 0.0175 | 0 | | | 0 | 0 | 0 | 1 | | 1 | 0 | 3 | 3 | 3 | 3 | 3 | 3 | 3 | 3 | 3 | 3 | 3 |
| | 0.0087 | 0 | | | 2 | 3 | 3 | 3 | | 3 | 3 | 3 | 3 | 3 | 3 | 3 | 3 | 3 | 3 | 3 | 3 | 3 |
| 82 | 5.6050 | 3 | | | 3 | 3 | 3 | 3 | | 3 | 3 | 3 | 3 | 3 | 3 | 3 | 3 | 3 | 3 | 3 | 3 | N |
| | 1.1210 | 3 | | | 0 | 3 | 3 | 3 | 3 | 3 | 3 | 3 | 3 | 3 | 3 | 3 | 3 | 3 | 2 | 3 | 3 | Z |
| | 0.5605 | 3 | | | 0 | 3 | 2 | | | 3 | 0 | 3 | 3 | 0 | 1 | 0 | 0 | 3 | 3 | 2 | 3 | Z |
| | 0.2803 | 3 | | | 3 | 3 | 3 | 3 | | 3 | 3 | 3 | 3 | 3 | 0 | 3 | 3 | 3 | 3 | 3 | 3 | 3 |
| | 0.1401 | 2 | | | 0 | 3 | 3 | 3 | | 3 | 3 | 3 | 3 | 3 | 3 | 3 | 3 | 3 | 3 | 3 | 3 | 3 |
| | 0.0701 | 0 | | | 1 | 3 | 1 | 3 | | 3 | 0 | 3 | 0 | 0 | 1 | 0 | 0 | 0 | 2 | 2 | 2 | 3 |
| | 0.0350 | 0 | | | 0 | 2 | 2 | 0 | | 0 | 0 | 0 | 0 | 0 | 0 | 0 | 0 | 0 | 0 | 0 | N | 1 |
| | 0.0175 | 0 | | | N | 0 | 0 | N | | N | 0 | 0 | 0 | 0 | 0 | 0 | 0 | 0 | 3 | 0 | N | N |
| | 0.0087 | 0 | | | 0 | 3 | 0 | 2 | | 3 | 0 | 3 | 3 | 0 | 0 | 3 | 3 | 3 | 3 | 3 | 3 | 3 |
| 83 | 5.6050 | 0 | | | 0 | 3 | 3 | 2 | | 3 | 0 | 3 | 3 | 3 | 0 | 3 | 3 | 3 | 3 | 3 | 3 | 3 |
| | 1.1210 | 0 | | | 0 | 2 | 3 | 2 | 3 | 3 | 2 | 3 | 3 | 0 | 0 | 3 | 3 | 3 | 2 | 3 | 3 | 3 |
| | 0.5605 | 0 | | | 2 | 2 | 2 | 2 | 3 | 3 | 2 | 3 | 2 | 0 | 0 | 3 | 3 | 3 | 2 | 0 | 3 | 2 |
| | 0.2803 | 0 | | | 0 | 0 | 0 | 0 | 0 | 0 | N | N | 1 | 0 | N | 0 | 0 | 0 | 0 | 0 | N | 3 |
| | 0.1401 | 0 | | | 2 | 0 | 3 | 0 | 0 | 3 | 2 | 2 | 0 | 0 | 3 | 0 | 0 | 0 | 0 | 0 | 3 | 3 |
| | 0.0701 | 0 | | | 0 | 0 | 2 | 0 | 0 | 0 | N | N | 0 | 0 | 2 | 0 | 0 | 0 | 0 | 0 | 3 | 3 |
| | 0.0350 | 0 | | | 0 | 0 | 0 | N | 0 | Z | Z | Z | 0 | N | N | 0 | 0 | 0 | N | 0 | N | N |
| | 0.0087 | 0 | | | 0 | 1 | 0 | 2 | 0 | 3 | 0 | 3 | 3 | 0 | 3 | Z | 0 | 0 | 0 | 3 | 3 | 3 |
| 84 | 5.6050 | 3 | 0 | 3 | 3 | 3 | 3 | 3 | 3 | 3 | 3 | 3 | 3 | 3 | 3 | 3 | 3 | 3 | 3 | 3 | 3 | 3 |
| | 1.1210 | 1 | 0 | 2 | 0 | 3 | 3 | 3 | 1 | 3 | 0 | 3 | 3 | 0 | 2 | 3 | 3 | 3 | 3 | 2 | 3 | 2 |
| | 0.2803 | 0 | N | 1 | 0 | 0 | 2 | 2 | 0 | 0 | 0 | 0 | 0 | 0 | N | 0 | 0 | 0 | 0 | 0 | N | 2 |
| | 0.0701 | N | 1 | 0 | N | Z | 0 | 0 | 1 | 0 | Z | Z | 0 | 0 | 3 | 0 | 0 | 0 | 0 | 0 | 0 | 3 |
| | 0.0175 | N | 0 | 0 | N | Z | 0 | 0 | 0 | 0 | Z | Z | 0 | N | 2 | N | 0 | 0 | 0 | 0 | 0 | 3 |
| 85 | 11.2100 | 3 | Z | 0 | 2 | N | 3 | 3 | 0 | 3 | Z | 3 | 3 | N | N | 3 | 3 | 3 | 3 | 3 | 3 | 3 |
| 86 | 5.6050 | 3 | 1 | 3 | 2 | 1 | 3 | 2 | 1 | 3 | 3 | 3 | 3 | 3 | 3 | 3 | 3 | 3 | 3 | 2 | 3 | 3 |
| | 1.1210 | 0 | 0 | 2 | N | Z | 2 | 0 | 0 | 0 | 3 | 3 | 2 | 0 | 1 | 0 | 0 | 2 | 0 | 0 | 0 | 3 |
| | 0.5605 | 1 | Z | 0 | 2 | Z | 0 | 0 | 0 | 3 | 0 | 0 | 0 | 0 | N | 0 | 0 | 0 | 0 | 0 | 0 | 3 |
| | 0.2803 | 1 | 1 | 0 | N | 1 | 0 | 0 | 0 | 0 | N | 0 | 0 | 0 | 0 | 0 | 0 | 0 | 3 | 0 | 0 | 3 |
| | 0.0701 | 0 | 0 | 0 | Z | N | 0 | N | 0 | 0 | N | N | 0 | 0 | N | 0 | N | N | 1 | 0 | 0 | 1 |
| 87 | 5.6050 | 3 | 2 | 3 | 0 | 3 | 3 | 0 | 3 | 3 | 3 | 3 | 3 | 3 | 3 | 3 | 3 | 3 | 3 | 3 | 3 | 3 |
| | 1.1210 | 0 | 0 | 2 | 0 | 0 | 0 | 0 | 0 | 0 | 0 | 3 | 0 | 0 | 3 | 0 | 0 | 0 | 0 | 0 | 0 | 3 |
| | 0.2803 | Z | 1 | 0 | 0 | 0 | 0 | 0 | 0 | 0 | 0 | 3 | 0 | 0 | 2 | 0 | 0 | 0 | 2 | 0 | 0 | 2 |
| | 0.0701 | 0 | 0 | 0 | 0 | 0 | 0 | 0 | 0 | 0 | 0 | 0 | 0 | 0 | 0 | 0 | 0 | 0 | 0 | 0 | 0 | 0 |
| | 0.0175 | 0 | 0 | 0 | 0 | 0 | 0 | 0 | 0 | 0 | 0 | 3 | 0 | 0 | 0 | 0 | 0 | 0 | 0 | 0 | 0 | 1 |
| 88 | 5.6050 | 3 | 0 | 3 | 0 | 3 | 3 | 0 | 3 | 2 | 2 | 3 | 3 | 3 | 2 | 3 | 3 | 3 | 3 | 2 | 3 | N |
| | 1.1210 | 0 | 0 | 0 | 0 | 0 | 0 | 0 | 0 | 0 | 0 | 3 | 0 | 0 | 0 | 0 | 0 | 0 | 2 | 0 | 0 | 0 |
| | 0.5605 | 0 | 0 | 0 | 0 | 0 | 0 | 0 | 0 | 0 | N | 3 | 0 | 0 | 0 | 0 | 0 | 0 | N | 0 | 0 | 1 |
| | 0.2803 | 0 | 0 | 0 | 0 | 0 | 0 | 0 | 0 | 0 | 0 | 0 | 0 | 0 | 0 | 0 | 0 | 0 | 3 | 0 | 0 | 2 |
| | 0.1401 | 0 | 2 | 0 | 0 | 0 | 0 | 0 | 0 | 0 | 2 | 3 | 0 | 0 | 0 | 0 | N | Z | 3 | 0 | 0 | 0 |
| | 0.0701 | 0 | 2 | 3 | 0 | 3 | 3 | 0 | 3 | 2 | 3 | 3 | 0 | 3 | 0 | 3 | 3 | 3 | 0 | 3 | 3 | 1 |
| 89 | 11.2100 | 3 | 2 | 3 | 0 | 3 | 3 | 1 | 3 | 2 | 3 | 3 | 0 | 3 | 3 | 0 | 0 | 3 | Z | 3 | 3 | 2 |
| | 5.6050 | 3 | 2 | 3 | 0 | 3 | 3 | 1 | 2 | 3 | 3 | 3 | 3 | 3 | 3 | 3 | 3 | 3 | 3 | 3 | 1 | 1 |

TABLE B-continued

| Ex. No. | Rate kg/ha | Sobe | Cotz | Rape | Cobu | Wibw | Mogl | Hese | Jiwe | Vele | Whez | Rice | Grso | Corn | Dobr | Prmi | Bygr | Lacg | Grft | Sube | Colq | Pesw |
|---|---|---|---|---|---|---|---|---|---|---|---|---|---|---|---|---|---|---|---|---|---|
| 91@ | 1.1210 | 3 | - | 1 | - | 0 | - | 1 | 0 | 3 | 2 | 3 | 3 | 1 | 3 | 3 | 3 | 3 | 3 | 3 | 3 | Z |
| @ | 5.6050 | 2 | 0 |  | 0 | 3 | 3 | 3 |  | 0 | 1 | 3 | 3 | 3 | 3 | 3 | 3 | 3 | 3 | 1 | 0 | Z |
| @ | 1.1210 | 0 | 0 |  | 0 | 2 | 1 | 0 |  | 0 | 0 | Z | 2 | 0 | 1 | 2 | 3 | 3 | 3 | 0 | 0 | Z |
| @ | 0.5605 | 0 | 0 |  | 0 | 0 | 1 | 0 |  | 0 | 0 | 3 | 0 | 0 | 0 | 1 | 1 | 2 | 1 | 0 | 0 | Z |
| @ | 0.2803 | 0 | 2 |  | 0 | 0 | 0 | 2 |  | 0 | 0 | 3 | 0 | 0 | 0 | 0 | 0 | 0 | 0 | 0 | 0 | Z |
| @ | 0.1401 | 0 | 0 |  | 0 | 0 | 0 | 0 |  | 0 | 0 | 0 | 0 | 0 | 0 | 0 | 0 | 0 | 0 | 0 | 0 | Z |
| @ | 0.0701 | 0 | 0 |  | 0 | 0 | 0 | 0 |  | 0 | 0 | 0 | 0 | 0 | 0 | 0 | 0 | 0 | 0 |  |  | Z |
| @ | 0.0350 | 0 | 0 |  | Z | 0 | 0 | 0 |  | 0 | 0 | 0 | 0 | 0 | 0 | 0 | 0 | 0 | 0 |  |  |  |
| 92+ | 5.6050 | 3 | 1 | 3 | Z | 3 | 3 | 3 | 3 | 3 | 3 | 3 | 3 | 3 | 3 | 3 | 3 | 3 | 3 |  |  |  |
| + | 1.1210 | 2 | 1 | 3 | Z | 3 | 3 | 3 | 3 | 2 | 3 | 3 | 3 | 0 | 3 | 3 | 3 | 3 | 3 |  |  |  |
| 92+ | 0.2803 | 0 | - | 0 | Z | 1 | - | 0 | 2 | 0 | 0 | 0 | 2 | 0 | 2 | 2 | 0 | 2 | 0 |  |  |  |
| + | 0.0701 | 0 | 2 | 0 | Z | 0 | 0 | 0 | 0 | 0 | 0 | 0 | 0 | 0 | 0 | 0 | 0 | 0 | 0 |  |  |  |
| + | 0.0175 | 0 | 0 | 0 | Z | 0 | 0 | 0 | 0 | 0 | 0 | 0 | 0 | 0 | 0 | 0 | 0 | 0 | 0 |  |  |  |
| + | 0.0087 | 0 | 0 | 0 | Z | 0 | 0 | 0 | 0 | 0 | 0 | 0 | 0 | 0 | 0 | 0 | 0 | 0 | 0 |  |  |  |
| 94+ | 5.6050 | 3 | 0 | 3 | Z | 3 | 3 | 3 | 3 | 3 | 3 | 3 | 3 | 3 | 3 | 3 | 3 | 3 | 3 |  |  |  |
| + | 1.1210 | 3 | 2 | 3 | Z | 3 | 3 | 3 | 3 | 3 | 3 | 3 | 3 | 1 | 3 | 3 | 3 | 3 | 3 |  |  |  |
| + | 0.2803 | 3 | 1 | 2 | Z | 3 | 3 | 3 | 3 | 3 | 3 | 3 | 3 | 2 | 3 | 3 | 3 | 3 | 3 |  |  |  |
| + | 0.0701 | 1 | 0 | 0 | Z | 3 | 3 | 3 | 3 | 3 | 3 | 3 | 3 | 0 | 3 | 3 | 3 | 3 | 3 |  |  |  |
| 94+ | 0.0175 | 0 | 0 | 0 | Z | 3 | 3 | 3 | 3 | 2 | 3 | 3 | 3 | 0 | 3 | 3 | 3 | 3 | 3 |  |  |  |
| + | 0.0087 | 0 | 0 | 0 | 3 | 3 | 3 | 3 | 3 | 0 | 2 | 3 | 3 | 0 | 2 | 2 | 3 | 3 | 3 |  |  |  |
| 95 | 5.6050 | 3 | 3 | 3 | 0 | 3 | 3 | 3 | 3 | 3 | 3 | 3 | 3 | 3 | 3 | 3 | 3 | 3 | 3 |  |  |  |
|  | 1.1210 | 1 | 0 | 3 | 0 | 3 | 3 | 3 | 3 | 3 | 3 | 3 | 3 | 1 | 3 | 3 | 3 | 3 | 3 |  |  |  |
|  | 0.2803 | 0 | 1 | 3 | 0 | 0 | 0 | 3 | 3 | 0 | 0 | 0 | 0 | 0 | 0 | 0 | 0 | 3 | 0 |  |  |  |
|  | 0.0701 | 0 | 0 | 0 | 0 | 2 | 1 | 0 | 2 | 0 | 0 | 0 | 0 | 0 | 0 | 0 | 0 | 0 | 0 |  |  |  |
|  | 0.0175 | 0 | 0 | 0 | 0 | 0 | 0 | 0 | 0 | 0 | 0 | 0 | 0 | 0 | 0 | 0 | 0 | 0 | 0 |  |  |  |
|  | 0.0044 | 0 | 0 | 0 | 0 | 0 | 0 | 0 | 0 | 0 | 0 | 0 | 0 | 0 | 0 | 0 | 0 | 0 | 0 |  |  |  |
| 97 | 5.6050 | 0 | 0 | 3 | 0 | 3 | 3 | 3 | 0 | 3 | 3 | 3 | 3 | 0 | 3 | 3 | 3 | 3 | 3 |  |  |  |
|  | 1.1210 | 1 | 0 | 0 | 0 | 0 | 1 | 1 | 0 | 0 | 0 | 0 | 0 | 0 | 0 | 0 | 0 | 3 | 0 |  |  |  |
|  | 0.2803 | 0 | 0 | 0 | 0 | 0 | 0 | 0 | 0 | 0 | 0 | 0 | 0 | 0 | 0 | 0 | 0 | 0 | 0 |  |  |  |
|  | 0.0701 | 0 | 0 | 0 | 0 | 0 | 0 | 0 | 0 | 0 | 0 | 0 | 0 | 0 | 0 | 0 | 0 | 0 | 0 |  |  |  |
| 99 | 5.6050 | 0 | 0 | 3 | 0 | 3 | 3 | 3 | 3 | 2 | 2 | 3 | 3 | 2 | 3 | 3 | 3 | 3 | 3 |  |  |  |
|  | 1.1210 | 0 | 0 | 0 | 0 | 0 | 0 | 0 | 0 | 0 | 0 | 0 | 0 | 0 | 0 | 0 | 0 | 0 | 0 |  |  |  |
|  | 0.2803 | 0 | 0 | 0 | 0 | 0 | 1 | 0 | 0 | 0 | 3 | 0 | 0 | 0 | 0 | 0 | 0 | 3 | 0 |  |  |  |
| 100 | 5.6050 | 1 | 0 | 0 | 0 | 3 | 0 | 0 | 0 | 0 | 3 | 0 | 3 | 3 | 3 | 3 | 3 | 3 | 3 |  |  |  |
| 100 | 1.1210 | 0 | 0 | 0 | 0 | 0 | 1 | 0 | 0 | 0 | 1 | 0 | 0 | 2 | 2 | 0 | 0 | 0 | 0 |  |  |  |
|  | 0.2803 | Z | 0 | 0 | Z | 0 | 0 | 0 | 0 | 0 | 1 | 0 | 0 | 0 | 0 | 0 | 0 | 0 | 0 |  |  |  |
| 101 | 5.6050 | 0 | 0 | 0 | 0 | 0 | 0 | 0 | 0 | 0 | 1 | 0 | 0 | 1 | 0 | 0 | 1 | 0 | 0 |  |  |  |
|  | 0.0701 | - | Z | - | 0 | 0 | 0 | 0 | 0 | 0 | - | - | - | 0 | - | 0 | - | 1 | - |  |  |  |
|  | 1.1210 | 0 | 0 | - | 0 | 0 | 0 | 0 | 0 | 0 | 0 | 0 | 0 | - | 0 | 0 | 0 | - | - |  |  |  |
| 102+ | 0.2803 | - | Z | 3 | Z | Z | 0 | 0 | 0 | 0 | 0 | 0 | 0 | 0 | 0 | 0 | 0 | 0 | 0 |  |  |  |
| + | 5.6050 | 3 | 0 | 3 | Z | 3 | 3 | 2 | 3 | 3 | 3 | 3 | 3 | 3 | 3 | 3 | 3 | 3 | 3 |  |  |  |
| 102+ | 1.1210 | - | 2 | 0 | Z | 3 | 3 | 2 | 3 | - | - | 3 | - | 3 | 2 | 3 | 3 | 3 | 3 |  |  |  |
| + | 0.2803 | 0 | 0 | 0 | Z | 3 | 3 | 0 | - | 0 | 0 | 3 | 0 | - | 0 | 0 | 0 | 3 | - |  |  |  |
| + | 0.0701 | 0 | 0 | 0 | Z | 0 | 0 | 0 | 0 | 0 | 0 | 0 | 0 | 0 | 0 | 0 | 0 | 0 | - |  |  |  |
| + | 0.0175 | 0 | 0 | 0 | Z | 0 | 0 | 0 | 0 | 0 | 0 | 0 | 0 | 0 | 0 | 0 | 0 | 0 | - |  |  |  |
| + | 0.0087 | 0 | 0 | 0 | Z | 0 | 0 | 0 | 0 | 0 | 0 | 0 | 0 | 0 | 0 | 0 | 0 | - | - |  |  |  |
| 103@ | 5.6050 | 3 | 3 | 0 | 0 | 3 | 3 | 3 | 3 | 3 | 3 | 3 | 3 | 3 | 3 | 3 | 3 | 3 | 3 | 3 | 3 | Z |
| @ | 1.1210 | 2 | 2 | 0 | 0 | 3 | 3 | 3 | - | 2 | 3 | 3 | 3 | 3 | 3 | 3 | 3 | 3 | 3 | 3 | 3 | Z |
| @ | 0.5605 | - | 0 | 0 | 0 | - | 3 | 3 | 0 | - | 2 | 3 | 3 | 0 | 2 | 3 | 3 | 3 | 3 | 3 | 3 | Z |

TABLE B-continued

| Ex. No. | Rate kg/ha | Sobe | Cotz | Rape | Cobu | Wibw | Mogl | Hese | Jiwe | Vele | Whez | Rice | Grso | Corn | Dobr | Prmi | Bygr | Lacg | Grft | Sube | Colq | Pesw |
|---|---|---|---|---|---|---|---|---|---|---|---|---|---|---|---|---|---|---|---|---|---|---|
| @ | 0.2803 | 0 |  |  | 0 | 1 | 3 | 3 |  | 0 | 1 | 3 | 3 | 1 | 0 | 2 | 3 | 3 | 3 | 3 | 3 | N |
| @ | 0.1401 | 1 |  |  | 0 | 0 | 3 | 1 |  | 0 | 0 | 3 | 0 | 0 | 1 | 0 | 3 | 3 | 3 | 3 | 3 | N |
| @ | 0.0701 | 0 |  |  | 1 | 0 | 0 | 1 |  | 0 | 0 | 0 | 0 | 0 | 0 | 0 | 0 | 1 | 1 | 1 | 1 | N |
| @ | 0.0350 | 0 |  |  | 0 | 0 | 0 | 0 |  | 0 | 0 | 0 | 0 | 0 | 0 | 0 | 0 | 0 | 0 | 0 | 0 | N |
| @ | 0.0175 | 0 |  |  | 0 | N | 0 | 0 |  | 0 | 0 | 0 | 0 | 0 | 0 | 0 | 0 | 0 | 0 | 0 | N | N |
| 104@ | 11.2100 | 0 | 0 | 3 | 2 | 1 | 0 | 0 | 2 | 0 | 1 | 3 | 0 | 0 | 0 | 1 | 3 | 3 | 2 | 3 | 3 | Z |
| @ | 5.6050 | 0 | 0 | 0 | N | 0 | 0 | N | 1 | 0 | 0 | 1 | 0 | 0 | 0 | N | 1 | 1 | 1 | 0 | 1 | Z |
| @ | 1.1210 | 0 | 0 | 0 | N | Z | N | 1 | 0 | 0 | 0 | 3 | 0 | 0 | 0 | 3 | 3 | 3 | 3 | 3 | 3 | Z |
| 105 | 11.2100 | 0 | 0 | 0 | 0 | 0 | 0 | 0 | 0 | 0 | 0 | 3 | 0 | 0 | 0 | 3 | 3 | 3 | 3 | 0 | 0 | — |
| | 5.6050 | 0 | 0 | 0 | 0 | 1 | 3 | 0 | 0 | 0 | 0 | 3 | 0 | 0 | 0 | 3 | 3 | 3 | 3 | 3 | 3 | — |
| | 1.1210 | 0 | 0 | 0 | 0 | 0 | 0 | 0 | 0 | 0 | 0 | 3 | 0 | 0 | 0 | 0 | 3 | 3 | 2 | 2 | 0 | — |
| 106 | 5.6050 | 2 | 0 | 3 | 0 | 0 | 3 | 0 | 0 | 0 | 2 | 3 | 3 | 0 | 0 | 3 | 3 | 3 | 3 | 0 | 0 |  |
| | 1.1210 | 0 | 0 | 0 | 0 | 0 | 0 | 0 | 0 | 0 | 0 | 0 | 0 | 0 | 0 | 3 | 3 | 3 | 3 | 0 | 0 |  |
| | 0.5605 | 0 | 0 | 0 | 0 | 0 | 0 | 0 | 0 | 0 | 0 | 0 | 0 | 0 | 0 | 0 | 3 | 2 | 2 | 0 | 0 |  |
| | 0.2803 | 0 | 0 | 0 | 0 | 0 | 0 | 0 | 0 | 0 | 0 | 0 | 0 | 0 | 0 | 0 | 0 | 0 | 0 | 0 | 0 |  |
| | 0.1401 | 0 | 0 | 0 | 0 | 0 | 0 | 0 | 0 | 0 | 0 | 0 | 0 | 0 | 0 | 0 | 0 | 0 | 0 | 0 | 0 |  |
| | 0.0701 | 0 | 0 | 0 | 0 | 0 | 0 | 0 | 0 | 0 | 0 | 0 | 0 | 0 | 0 | 0 | 0 | 0 | 0 | 0 | 0 |  |
| | 0.0351 | 0 | 0 | 0 | 0 | 0 | 0 | 0 | 0 | 0 | 0 | 0 | 0 | 0 | 0 | 0 | 0 | 0 | 0 | 0 | 0 |  |
| | 0.0175 | 0 | 0 | 0 | 0 | 0 | 0 | 0 | 0 | 0 | 0 | 0 | 0 | 0 | 0 | 0 | 0 | 0 | 0 | 0 | 0 |  |
| 107 | 5.6050 | 2 | 0 | 0 | 0 | 3 | 3 | 0 | 3 | 2 | 3 | 3 | 3 | 3 | 3 | 3 | 3 | 3 | 3 | 3 | 3 |  |
| | 1.1210 | 0 | 0 | 1 | 0 | 3 | 0 | 0 | 1 | 1 | 1 | 3 | 0 | 0 | 3 | 3 | 3 | 3 | 3 | 3 | 3 |  |
| | 0.5605 | Z | 0 | 0 | 0 | 3 | 0 | 0 | Z | 0 | 0 | 3 | 0 | 0 | 2 | 0 | 3 | 3 | 3 | 3 | 3 |  |
| | 0.2803 | 0 | 0 | 0 | 0 | 0 | 0 | 0 | Z | 0 | 0 | 2 | 0 | 0 | 0 | 0 | 2 | 2 | 2 | 0 | 0 |  |
| | 0.1401 | 0 | 0 | 0 | 0 | 3 | 0 | 0 | 3 | 0 | 0 | 3 | 0 | 0 | 3 | 0 | 3 | 0 | 0 | 0 | 0 |  |
| 108 | 5.6050 | 3 | 0 | 3 | 0 | 3 | 3 | 3 | 3 | 3 | 3 | 3 | 3 | 3 | 3 | 3 | 3 | 3 | 3 | 3 | 3 |  |
| | 1.1210 | 3 | 0 | 3 | 0 | 0 | 2 | 1 | 2 | 2 | 0 | 2 | 2 | 2 | 2 | 0 | 2 | 0 | 2 | 0 | 0 |  |
| | 0.2803 | 0 | 0 | 0 | 0 | 0 | 0 | 0 | 0 | 0 | 0 | 0 | 0 | 0 | 0 | 0 | 0 | 0 | 0 | 0 | 0 |  |
| | 0.0701 | 0 | 0 | 0 | 0 | 0 | 0 | 0 | 0 | 0 | 0 | 0 | 0 | 0 | 0 | 0 | 0 | 0 | 0 | 0 | 0 |  |
| 108 | 0.0175 | 0 | 0 | 0 | Z | Z | 0 | 0 | Z | 0 | Z | Z | 0 | 0 | Z | Z | Z | Z | Z | 0 | N |  |
| | 0.0087 | 0 | 0 | 0 | 0 | 0 | 0 | 0 | 0 | 0 | 0 | 0 | 0 | 0 | 0 | 0 | 0 | 0 | 0 | 0 | 0 |  |
| 111+ | 5.6050 | 3 | 0 | 3 | 0 | 3 | 3 | 3 | 3 | 3 | 3 | 3 | 3 | 3 | 3 | 3 | 3 | 3 | 3 | 3 | 3 |  |
| + | 1.1210 | 3 | 0 | 3 | 0 | 3 | 3 | 2 | 3 | 3 | 3 | 3 | 3 | 3 | 2 | 3 | 3 | 3 | 3 | 3 | 3 |  |
| + | 0.2803 | 0 | 0 | 0 | 0 | 2 | 3 | 3 | 3 | 3 | 0 | 0 | 3 | 0 | 0 | 0 | 3 | 3 | 3 | 0 | 3 |  |
| + | 0.0701 | Z | 0 | 3 | 0 | 0 | 1 | 3 | 1 | 0 | 1 | 1 | 0 | 1 | 0 | 1 | 0 | 0 | 1 | 1 | 1 |  |
| 112 | 5.6050 | 3 | 0 | 3 | 0 | 3 | 3 | 3 | 3 | 3 | 3 | 3 | 3 | 3 | 3 | 3 | 3 | 3 | 3 | 3 | 3 |  |
| | 1.1210 | 2 | 0 | 2 | 0 | 3 | 3 | 3 | 3 | 3 | 3 | 3 | 3 | 3 | 3 | 3 | 3 | 3 | 3 | 0 | 0 |  |
| | 0.2803 | 1 | 0 | 0 | 0 | 0 | 1 | 1 | 2 | 2 | 0 | 1 | 0 | 0 | 0 | 0 | 3 | 3 | 3 | 0 | 0 |  |
| 112 | 0.0701 | 0 | 0 | 1 | 0 | 0 | 0 | 0 | 0 | 0 | 0 | 0 | 0 | 0 | 0 | 0 | 3 | 3 | 3 | 0 | 0 |  |
| | 0.0175 | 0 | 0 | 0 | 0 | 0 | 0 | 0 | 0 | 0 | 0 | 0 | 0 | 0 | 0 | 0 | 1 | 1 | 0 | 0 | 0 |  |

*CHEZ REPLACING DOBR.
CHEAT GRASS REPLACING DOWNY BROME
@ POOR PESW EMERGENCE.
+ COBU EMERGENCE AND RICE GROWTH VARIABLE
+ COBU POOR THROUGHOUT TEST

POST-EMERGENT HERBICIDE EXAMPLES

Although as has been stated above the compounds of this invention exhibit predominantly pre-emergence activity in greenhouse testing, nevertheless many of these compounds are active post-emergent herbicides. The post-emergent activity is best seen on younger plants treated at the 1½ to 2 leaf stage. In the tests which follow, larger and more developed plants were used.

The post-emergence herbicidal activity of compounds of this invention was demonstrated by greenhouse testing, and the results are shown in the following Table C. The post-emergent herbicidal activity index used in Table C is as follows:

| Plant Response | Index |
|---|---|
| 0-24 inhibition | 0 |
| 25-49 inhibition | 1 |
| 50-74 inhibition | 2 |
| 75-99 inhibition | 3 |
| 100% inhibition | 4 |
| Species not planted | — or a blank |
| Species planted, no data | N |

Where appropriate, footnotes are shown at the end of the table.

As was the case with the pre-emergence data, some of the compounds initially received ratings for plant response directly as percent inhibition in ten percent increments. Where this is the case, the percentage has been converted according to the scale above.

POST-EMERGENCE ACTIVITY ON WEEDS

Top soil was placed in pans having holes in the bottom and compacted to a depth of 0.95 to 1.27 cm. from the top of the pan. A predetermined number of seeds of each of several dicotyledonous and monocotyledonous annual plant species and/or vegetative propagules for the perennial plant species were placed on the soil and pressed into the soil surface. The seeds and/or vegetative propagules were covered with soil and leveled. The pans were then placed on a bench in the greenhouse and watered as needed for germination and growth. After the plants reached the desired age (two to three weeks), each pan (except the control pans) was removed to a spraying chamber and sprayed by means of an atomizer. The spray solution or suspension contained about 0.4% by volume of an emulsifying agent and a sufficient amount of the candidate chemical to give an application rate of the active ingredient of 11.2 kg/ha while applying a total amount of solution or suspension equivalent to 1870 L/Ha (200 gallons /acre). The pans were returned to the greenhouse and watered as before and the injury to the plants as compared to those in control pans was observed at approximately 10–14 days (usually 11 days) and in some instances observed again at 24–28 days (usually 25 days) after spraying. These latter observations are designated by a "pound" sign (#) following the column of example numbers in the Table. The plant species used in this set of tests were the same as those used in the first set of pre-emergence tests, and the plant identifying codes are the same as those shown for Table A.

TABLE C

| Ex. No. | Rate kg/ha | Yens | Anbg | Sejg | Dobr | Bygr | Mogl | Cobu | Vele | Inmu | Wibw | Cath | Colq | Pesw | Rhqg | Rhjg |
|---|---|---|---|---|---|---|---|---|---|---|---|---|---|---|---|---|
| 1 | 11.2100 | 0 | | | 0 | 2 | 1 | 0 | 0 | | | N | 1 | 0 | 0 | 0 |
| 2 | 11.2100 | 0 | | | 0 | 0 | 0 | 0 | 1 | | | 0 | 0 | 0 | 0 | 0 |
| 3 | 11.2100 | 0 | | | 0 | 2 | 2 | 2 | 2 | | | 1 | 0 | 2 | 0 | 0 |
| 4 | 11.2100 | 0 | | | 0 | 0 | 0 | 0 | 1 | | | 0 | 0 | 0 | 0 | 0 |
| 5 | 11.2100 | 0 | | | 0 | 1 | 0 | 0 | 1 | | | 1 | N | 1 | 0 | 0 |
| 6 | 11.2100 | 1 | | | 0 | 1 | 1 | 1 | 1 | | | 0 | 1 | 0 | 0 | 0 |
| 7 | 11.2100 | 0 | | | 0 | 0 | 0 | 0 | 0 | | | 0 | 0 | 0 | 0 | 0 |
| 8 | 11.2100 | 0 | | | 0 | 0 | 0 | 0 | 0 | | | 0 | 0 | 0 | 0 | 0 |
| 9 | 11.2100 | 0 | | | — | 0 | 0 | 0 | 0 | | | 0 | 4 | 0 | 0 | 0 |
| 10 | 11.2100 | 0 | | | 0 | 0 | 0 | 0 | 0 | | | 0 | 0 | 0 | 0 | 0 |
| 11 | 11.2100 | 0 | | | 0 | 0 | 1 | 0 | 0 | | | 0 | 1 | 0 | 0 | 0 |
| 12 | 11.2100 | 0 | | | 0 | 0 | 0 | 0 | 0 | | | 0 | 0 | 0 | 0 | 0 |
| 13 | 11.2100 | 0 | | | 0 | 0 | 0 | 0 | 0 | | | 0 | 0 | 0 | 0 | 0 |
| 14 | 11.2100 | 0 | | | 0 | 0 | 0 | 0 | 0 | | | 0 | 0 | 0 | 0 | 0 |
| 15 | 11.2100 | 0 | | | 0 | 1 | 1 | 1 | 0 | | | 0 | 0 | 0 | 0 | 0 |
| 16 | 11.2100 | 0 | | | 0 | 0 | 0 | 0 | 0 | | | 0 | N | 0 | 0 | 0 |
| 17 | 11.2100 | 0 | | | 0 | 1 | 0 | 1 | 0 | | | 0 | 1 | 1 | 0 | 0 |
| 18 | 11.2100 | 1 | | | 0 | 1 | 1 | 2 | 2 | | | 1 | 1 | 1 | 0 | 0 |
| 19 | 11.2100 | 0 | | | 0 | 0 | 1 | 0 | 0 | | | 0 | 1 | 0 | 0 | 0 |
| 20 | 11.2100 | 0 | | | 0 | 0 | 1 | 0 | 1 | | | 0 | 2 | 1 | 0 | N |
| 21 | 11.2100 | 0 | | | 0 | 0 | 0 | 0 | 0 | | | 0 | 0 | 0 | 0 | 0 |
| 22 | 11.2100 | 0 | | | 0 | 0 | 0 | 0 | 0 | | | 0 | 3 | 0 | 0 | 0 |
| 23 | 11.2100 | 0 | | | 0 | 1 | 1 | 0 | 0 | | | 0 | 1 | 0 | 0 | 0 |
| 24 | 11.2100 | 0 | | | 0 | 0 | 0 | 0 | 0 | | | 0 | 0 | 0 | 0 | 0 |
| 25 | 11.2100 | 0 | | | 0 | 0 | 0 | 0 | 0 | | | 0 | 0 | 0 | 0 | 0 |
| 26 | 11.2100 | 0 | | | 0 | 0 | 0 | 0 | 0 | | | 0 | 0 | 0 | 0 | 0 |
| 27 | 11.2100 | 0 | | | 1 | 1 | 1 | 1 | 1 | | | — | 1 | 0 | 0 | 0 |
| 28 | 11.2100 | 0 | | | 0 | 1 | 1 | 2 | 2 | | | 1 | 2 | 1 | 0 | 0 |
| 29 | 11.2100 | 0 | | | 0 | 0 | 1 | N | 1 | | | 0 | 0 | 0 | 0 | 0 |
| 30 | 11.2100 | 0 | | | 0 | 1 | 1 | 1 | 2 | | | 0 | 1 | 1 | 0 | 0 |
| 31 | 11.2100 | 1 | | | 0 | 0 | 1 | 0 | 1 | | | 1 | N | 1 | 1 | 2 |
| 32 | 11.2100 | 0 | | | 0 | 0 | 1 | 0 | 1 | | | 0 | 1 | 0 | 0 | 0 |
| 33 | 11.2100 | 0 | | | 0 | 0 | 0 | 0 | 0 | | | 0 | N | 0 | 0 | 0 |
| 34 | 11.2100 | 1 | | | 1 | 1 | 1 | 1 | 1 | | | 1 | 0 | 0 | 1 | 0 |
| 35 | 11.2100 | 1 | | | 1 | 1 | 1 | 0 | 1 | | | 0 | 0 | 0 | 1 | 0 |
| 36 | 11.2100 | 0 | | | 0 | 1 | 1 | 1 | 1 | | | 0 | 0 | 0 | 0 | 0 |
| 37 | 11.2100 | 0 | | | 0 | 1 | 1 | 0 | 1 | | | 0 | 0 | 0 | 0 | 0 |
| 38 | 11.2100 | 0 | | | 0 | 1 | 0 | 0 | 0 | | | 0 | 0 | 0 | 0 | 0 |
| 39 | 11.2100 | 0 | | | 0 | 0 | 0 | 0 | 0 | | | 0 | 0 | 0 | 0 | 0 |
| 41 | 11.2100 | 0 | | | 0 | 1 | 1 | 1 | 1 | | | 0 | 0 | 0 | 0 | N |

TABLE C-continued

| Ex. No. | Rate kg/ha | Yens | Anbg | Sejg | Dobr | Bygr | Mogl | Cobu | Vele | Inmu | Wibw | Cath | Colq | Pesw | Rhqg | Rhjg |
|---|---|---|---|---|---|---|---|---|---|---|---|---|---|---|---|---|
| 42 | 11.2100 | 0 | | | 1 | 1 | 1 | 1 | 0 | | | 0 | 0 | 0 | 0 | 3 |
| 43 | 11.2100 | 0 | | | 0 | 0 | 3 | 2 | 1 | | | 0 | 2 | 1 | 0 | 3 |
| 44 | 11.2100 | 0 | | | 0 | 2 | 1 | 0 | 0 | | | 0 | 1 | 0 | 0 | 0 |
| 45 | 11.2100 | 0 | | | — | 0 | 1 | 1 | 1 | | | 0 | 4 | 0 | 0 | 0 |
|  | 11.2100 | 0 | | | — | 0 | 1 | 2 | 2 | | | 0 | 4 | 0 | 0 | 0 |
| 46 | 11.2100 | 1 | | | — | 0 | 0 | 1 | 1 | | | 0 | 0 | 0 | 0 | 1 |
| 47 | 11.2100 | 0 | | | 0 | 0 | 1 | 1 | 0 | | | 0 | 1 | 0 | 0 | 0 |
| 48 | 11.2100 | 0 | | | 0 | 0 | 0 | 1 | 0 | | | 0 | 0 | 0 | 0 | 0 |
| 49 | 11.2100 | 0 | | | 0 | 0 | 0 | 0 | 0 | | | 0 | 3 | 0 | 0 | 0 |
| 50 | 11.2100 | 0 | | | 0 | 0 | 2 | 1 | 0 | | | 0 | 0 | 0 | 0 | 0 |
| 51 | 11.2100 | 0 | | | 0 | 0 | 1 | 0 | 1 | | | 0 | 1 | 0 | 0 | 0 |
| 52 | 11.2100 | 0 | | | 0 | 0 | 0 | 0 | 0 | | | 0 | 1 | 0 | 0 | 0 |
| 53 | 11.2100 | 0 | | | 0 | 0 | 2 | 0 | 1 | | | 0 | 0 | 0 | 0 | 0 |
| 54 | 11.2100 | 0 | | | 0 | 0 | 0 | 0 | 0 | | | 0 | 1 | 0 | 0 | 0 |
| 55 | 11.2100 | 0 | | | 0 | 0 | 2 | 1 | 0 | | | 0 | 0 | 0 | 0 | 0 |
| 56 | 11.2100 | 0 | | | 0 | 0 | 0 | 0 | 0 | | | 0 | 0 | 0 | 0 | 0 |
| 57 | 11.2100 | 0 | | | 0 | 0 | 0 | 0 | 0 | | | 0 | 0 | 0 | 0 | 0 |
| 58 | 11.2100 | 0 | | | 0 | 0 | 0 | 0 | 0 | | | 0 | 0 | 0 | 0 | 0 |
| 59 | 11.2100 | 0 | | | 0 | 2 | 1 | 1 | 0 | | | 0 | 0 | 0 | 0 | 0 |
| 60 | 11.2100 | 0 | | | 0 | 2 | 1 | 1 | 0 | | | 0 | 0 | 0 | 0 | 0 |
| 61 | 11.2100 | 0 | | | 0 | 1 | 0 | 0 | 0 | | | 0 | 0 | 0 | 0 | 0 |
| 62 | 11.2100 | 0 | | | 0 | 1 | 1 | 1 | 1 | | | 0 | 2 | 0 | 0 | 0 |
| 63 | 11.2100 | 0 | | | 0 | 2 | 0 | 1 | 0 | | | 0 | 2 | 0 | 0 | 0 |
| 64 | 11.2100 | 0 | | | 0 | 0 | 0 | 0 | 0 | | | 0 | 0 | 0 | 0 | 0 |
| 65 | 11.2100 | 0 | | | 0 | 0 | 0 | 0 | 0 | | | 0 | 0 | 0 | 0 | 0 |
| 66 | 11.2100 | 0 | | | 0 | 0 | 0 | 0 | 0 | | | 0 | 0 | 0 | 0 | 0 |
| 67 | 11.2100 | 0 | | | 0 | 1 | 1 | 0 | 0 | | | 0 | 2 | 0 | 0 | 0 |
| 68 | 11.2100 | 0 | | | 0 | 0 | 0 | 0 | 0 | | | 0 | 0 | 0 | 0 | 0 |
| 69 | 11.2100 | 1 | | | 0 | 1 | 1 | 0 | 0 | | | 0 | 1 | 0 | 0 | 0 |
| 70 | 11.2100 | 0 | | | 0 | 0 | 0 | 0 | 0 | | | N | 0 | 0 | 0 | 0 |
| 71 | 11.2100 | 0 | | | 0 | 0 | 0 | 0 | 0 | | | 0 | 1 | 0 | 0 | 0 |
| 72 | 11.2100 | 0 | | | 0 | 0 | 0 | 0 | 0 | | | 0 | 0 | 0 | 0 | 0 |
| 73 | 11.2100 | 0 | | | 0 | 0 | 0 | 0 | 0 | | | 0 | 0 | 0 | 0 | 0 |
| 74 | 11.2100 | 0 | | | 0 | 0 | 0 | 0 | 0 | | | 0 | 0 | 0 | 0 | 0 |
| 75 | 11.2100 | 0 | | | 0 | 0 | 0 | 0 | 0 | | | 0 | 0 | 0 | 0 | 0 |
| 76 | 11.2100 | 0 | | | 0 | 0 | 0 | 0 | 0 | | | 0 | 0 | 0 | 0 | 0 |
| 77 | 11.2100 | 0 | | | 0 | 0 | 0 | 0 | 0 | | | 0 | 0 | 0 | 0 | 0 |
| 78* | 11.2100 | 0 | | | 0 | 1 | 0 | 0 | 0 | | | 0 | N | 0 | 0 | 0 |
| 79 | 11.2100 | 0 | | | 0 | 0 | 1 | 0 | 0 | | | 0 | 3 | 0 | 0 | 0 |
| 80 | 11.2100 | 0 | | | 0 | 1 | 1 | 1 | 1 | | | 0 | 3 | 0 | 0 | 0 |
| 81 | 11.2100 | 0 | | | 0 | 1 | 1 | 0 | 1 | | | 1 | 0 | 0 | 0 | N |
| 82 | 11.2100 | 0 | | | 0 | 1 | 1 | 0 | 0 | | | 0 | — | 0 | 0 | 0 |
| 83 | 11.2100 | 1 | | | 0 | 3 | 1 | 1 | 1 | | | N | 2 | 0 | 1 | 0 |
| 84 | 11.2100 | 0 | 0 | 0 | 0 | 0 | 1 | 0 | 1 | 2 | 2 | | | | | |
| 85 | 11.2100 | 0 | 0 | 0 | 0 | 0 | 0 | 0 | 1 | 1 | 2 | | | | | |
| 86 | 11.2100 | 0 | 0 | 0 | 0 | 0 | 0 | 0 | 0 | 1 | 0 | | | | | |
| 87 | 11.2100 | 0 | 0 | 2 | 0 | 2 | 2 | 2 | 2 | 2 | 2 | | | | | |
| 88@ | 11.2100 | 0 | | | 0 | 0 | 1 | 0 | 0 | | | 0 | 0 | 0 | 0 | 0 |
| 89+ | 11.2100 | 0 | | | 0 | 0 | 0 | 0 | 0 | | | 0 | 0 | 0 | 0 | 0 |
| 90 | 11.2100 | 0 | 0 | 2 | 0 | 2 | 0 | 0 | 1 | 0 | 0 | | | | | |
| 91 | 11.2100 | 0 | | | 0 | 0 | 1 | 1 | 1 | | | 0 | 3 | 2 | 1 | 0 |
| 92 | 11.2100 | 0 | 0 | 2 | 0 | 1 | 1 | 0 | 1 | 1 | 1 | | | | | |
| 93+ | 11.2100 | 0 | 0 | 2 | 0 | 2 | 2 | 2 | 2 | 2 | 2 | | | | | |
| 94 | 11.2100 | 0 | 0 | 2 | 0 | 2 | 2 | 0 | 2 | 1 | 2 | | | | | |
| 95 | 11.2100 | 0 | 0 | 2 | 0 | 2 | 2 | 2 | 2 | 1 | 2 | | | | | |
| 96( | 11.2100 | 0 | 0 | 0 | 0 | 2 | 2 | 2 | 2 | 2 | 1 | | | | | |
| 97 | 11.2100 | 0 | 0 | 0 | 0 | 0 | 0 | 1 | 1 | 1 | 1 | | | | | |
| 98 | 11.2100 | 0 | 0 | 2 | 0 | 2 | 2 | 1 | 1 | 1 | 2 | | | | | |
| 99 | 11.2100 | 0 | 0 | 0 | 0 | 2 | 0 | 0 | 1 | 1 | 1 | | | | | |
| 100 | 11.2100 | 0 | 0 | 0 | 0 | 0 | 0 | 0 | 1 | 1 | 1 | | | | | |
| 101 | 11.2100 | 0 | 0 | 0 | 0 | 0 | 0 | 0 | 0 | 1 | 1 | | | | | |
| 102 | 11.2100 | 0 | 0 | 2 | 0 | 2 | 2 | 0 | 2 | 1 | 2 | | | | | |
| 103 | 11.2100 | 0 | | | 0 | 0 | 0 | 1 | 0 | | | 0 | 0 | N | 0 | 0 |
| 104 | 11.2100 | 0 | | | 0 | 0 | 0 | 0 | 0 | | | 0 | 0 | N | 0 | 0 |
| 105 | 11.2100 | 0 | | | 0 | 0 | 1 | 0 | 0 | | | 0 | 0 | N | 0 | 0 |
| 106@ | 11.2100 | 0 | | | 0 | 0 | 1 | 0 | 0 | | | 0 | 1 | 0 | 0 | 0 |
| 107 | 11.2100 | 0 | 0 | 0 | 0 | 0 | 0 | 0 | 0 | 0 | 0 | | | | | |
| 108 | 11.2100 | 0 | 0 | 0 | 0 | 1 | 2 | 0 | 2 | 1 | 2 | | | | | |
| 109( | 11.2100 | 0 | 0 | 2 | 0 | 2 | 2 | 1 | 2 | 2 | 2 | | | | | |
| 110− | 11.2100 | 0 | 0 | 2 | 0 | 2 | 2 | 0 | 2 | 2 | 2 | | | | | |
| 111 | 11.2100 | 0 | 0 | 2 | 0 | 2 | 1 | 0 | 2 | 1 | 2 | | | | | |

TABLE C-continued

| Ex. No. | Rate kg/ha | Yens | Anbg | Sejg | Dobr | Bygr | Mogl | Cobu | Vele | Inmu | Wibw | Cath | Colq | Pesw | Rhqg | Rhjg |
|---|---|---|---|---|---|---|---|---|---|---|---|---|---|---|---|---|
| 112 | 11.2100 | 0 | 0 | 2 | 0 | 2 | 2 | 2 | 1 | 2 | 2 | | | | | |

*POOR LQ GERMINATION.
DAMPING OFF-LQ.
@ POOR SMARTWEED GERMINATION
+ POOR GERMINATION-SW
+ DAMPING OF - IM, WB
( DAMPING OFF- IM, WB
) DAMPING OFF- IM, WB POOR GERMINATION- CB
- DAMPING OFF-IM, WB POOR GERMINATION-CB

POST-EMERGENCE ACTIVITY ON WEEDS AND CROPS

Compounds of this invention were tested for herbicidal activity on weed plants in the presence of crop plants according to the following procedure:

Topsoil (silt loam) is sieved through a screen having 1.27 cm openings. In some of the tests the soil was mixed with fertilizer (1225 g/cu. m of 12/5/9 containing isobutylidene diurea), while in other tests the fertilizer was omitted. This mixture is steam sterilized and then placed in aluminum pans 6.985 cm deep having ten holes in the bottom each 0.635 cm in diameter. The soil mixture is compacted to a depth of 1.27 cm. from the top of the pan. A predetermined number of seeds of each of several dicotyledonous and monocotyledonous annual plant species and/or vegetative propagules for the perennial plant species are placed on the soil and pressed into the soil surface. The seeds and/or vegetative propagules are covered with 1.27 cm of a mixture of 50% topsoil and 50% of a mixture of Canadian sphagnum peat moss, vermiculite and a wetting agent. The pans are then placed on a capillary mat on a greenhouse bench and subirrigated as needed. After the plants reach the desired stage (9 to 14 days, 1 to 3 true leaf stage), each pan (except the control pans) is removed to a spraying chamber and sprayed by means of an atomizer, operating at a spray pressure of 170.3 kPa (10 psig) at the application rates noted in Table D. In the spray solution is an amount of an emulsifying agent mixture (35% butylamine salt of dodecylbenzenesulfonic acid and 65% tall oil condensed with ethylene oxide in the ratio of 11 mols of ethylene oxide/mol of tall oil) to give a spray solution or suspension. The spray solution or suspension contains a sufficient amount of the candidate chemical in order to give application rates of the active ingredient corresponding to those shown in Table D below while applying a total amount of solution or suspension equivalent to 1870 L/Ha (200 gallons/acre). The pans are returned to the greenhouse and watered as before and the injury to the plants as compared to the control pans is observed at approximately 10–14 days (usually 11 days) and in some instances observed again at 24–28 days (usually 25 days) after spraying. These latter observations are designated by a "pound" sign (#) following the column of example numbers in the Table.

In the following Table D the legends used to identify the plant species are the same as those used in the preceeding Table B.

TABLE D

| Ex. No. | Rate kg/ha | Sobe | Cotz | Rape | Cobu | Wibw | Nogl | Hese | Jiwe | Vele | Whez | Rice | Grso | Corn | obr | rmi | ygr | acg | rft | ube | olq | esw |
|---|---|---|---|---|---|---|---|---|---|---|---|---|---|---|---|---|---|---|---|---|---|---|
| 18 | 5.6050 | 2 | | | 1 | 2 | 2 | 2 | | 0 | 2 | 1 | 2 | 2 | 0 | 1 | 2 | 2 | 1 | 1 | 2 | N |
| | 5.6050 | 3 | | | 3 | 3 | 3 | 3 | | 2 | 2 | 1 | 2 | 2 | 1 | 2 | 3 | 2 | 2 | 1 | 2 | N |
| | 5.6050 | 2 | 2 | 2 | 1 | 2 | 2 | 3 | 3 | 3 | 1 | 0 | 3 | 3 | 0 | 2 | 2 | 3 | 2 | | | |
| | 5.6050 | 3 | 2 | 3 | 2 | 3 | 2 | 3 | 3 | 3 | 2 | 1 | 3 | 3 | 2 | 2 | 2 | 3 | 2 | | 2 | N |
| | 1.1210 | 1 | | | 1 | 0 | 1 | 1 | | 2 | 0 | 0 | 1 | 2 | 0 | 1 | 2 | 2 | 1 | 1 | | |
| | 1.1210 | 2 | 2 | 2 | 2 | 2 | 2 | 2 | | 2 | 1 | 0 | 2 | 3 | 0 | 2 | 2 | 3 | 0 | 0 | 2 | N |
| | 1.1210 | 2 | | | 2 | 0 | 3 | 2 | 3 | 3 | 0 | 0 | 2 | 2 | 0 | 2 | 2 | 3 | 1 | 1 | 1 | |
| | 1.1210 | 2 | 2 | 2 | 2 | 2 | 2 | 2 | | 2 | 0 | 0 | 2 | 2 | 0 | 0 | 2 | 2 | 0 | 0 | 1 | N |
| 18 | 0.5605 | 1 | | | 1 | 0 | 1 | 1 | | 0 | 1 | 0 | 0 | 1 | 1 | 0 | 0 | 3 | 1 | 1 | 1 | N |
| | 0.5605 | 1 | | | 2 | 2 | 2 | 2 | | 2 | 0 | 0 | 0 | 0 | 0 | 0 | 2 | 2 | 0 | 0 | 1 | N |
| | 0.2803 | 0 | | | 2 | 0 | 0 | 2 | | 0 | 0 | 0 | 0 | 0 | 0 | 0 | 0 | 0 | 0 | 0 | 1 | |
| | 0.2803 | 0 | 1 | 2 | 1 | 1 | 1 | 0 | | 1 | 0 | 0 | 0 | 0 | 0 | 0 | 0 | 3 | 0 | | 1 | |
| | 0.2803 | 2 | 2 | 3 | 2 | 2 | 2 | 2 | 3 | 2 | 0 | 0 | 0 | 0 | 0 | 0 | 0 | 3 | 0 | 0 | 1 | N |
| | 0.2803 | 2 | 1 | 2 | 2 | 2 | 2 | 2 | 2 | 0 | 0 | 0 | 0 | 0 | 0 | 0 | 0 | 3 | 0 | 0 | 1 | |
| | 0.1401 | 0 | | | 0 | 0 | 0 | 0 | | 1 | 0 | 0 | 0 | 0 | 0 | 0 | 0 | 0 | 0 | | | |
| | 0.1401 | 0 | | | 0 | 0 | 0 | 0 | | 2 | 0 | 0 | 0 | 0 | 0 | 0 | 0 | 3 | 0 | 0 | 1 | |
| 18 | 0.0701 | 1 | 0 | 2 | 0 | 0 | 0 | 0 | | 0 | 0 | 0 | 0 | 0 | 0 | 0 | 0 | 0 | 0 | 0 | 1 | |
| | 0.0701 | 0 | | | 0 | 0 | 2 | 0 | 2 | 2 | 0 | 0 | 0 | 0 | 0 | 0 | 0 | 3 | 0 | 0 | 0 | |
| | 0.0701 | 0 | 1 | 2 | 0 | 0 | 2 | 1 | | 2 | 0 | 0 | 0 | 0 | 0 | 0 | 0 | 0 | 0 | 0 | 0 | |
| 36 | 5.2687 | 2 | 2 | 2 | 2 | 3 | 2 | 2 | 3 | 3 | 0 | 0 | 0 | 3 | 0 | 2 | 2 | 3 | 2 | 0 | 1 | |
| | 5.2687 | 2 | 2 | 3 | 2 | 2 | 2 | 3 | 3 | 3 | 0 | 0 | 0 | 0 | 0 | 2 | 2 | 3 | 2 | 0 | | 0 |
| | 1.1210 | 1 | 1 | 2 | 1 | 2 | 2 | 3 | 2 | 2 | 0 | 0 | 0 | 0 | 0 | 0 | 0 | 3 | 1 | 0 | 0 | |
| | 1.1210 | 2 | 2 | 2 | 2 | 2 | 3 | 2 | 2 | 2 | 1 | 0 | 0 | 3 | 2 | 2 | 2 | 3 | 1 | 0 | 0 | |
| | 0.2803 | 0 | | | 0 | N | 0 | 2 | N | 1 | 0 | 0 | 0 | 1 | 0 | N | 0 | 3 | 1 | 0 | | |
| 36 | 0.2803 | 1 | 2 | 1 | 1 | N | 2 | 0 | Z | 0 | 0 | 0 | 0 | 0 | 0 | 0 | 0 | 3 | 0 | 0 | | |
| | 0.0701 | 0 | | | 0 | Z | 0 | 0 | Z | 0 | 0 | 0 | 0 | 0 | 0 | 0 | 0 | 0 | 0 | 0 | 0 | |
| | 0.0701 | 0 | 1 | 0 | 1 | Z | 2 | 1 | Z | 0 | 0 | 0 | 0 | 1 | 0 | 0 | 2 | 2 | 0 | 0 | 0 | |
| 43 | 5.6050 | 1 | | | 0 | Z | 2 | 0 | 3 | 3 | 0 | 0 | 0 | 0 | 0 | 0 | 0 | 2 | 2 | 2 | 0 | 0 |
| 44 | 1.1210 | 0 | | | 1 | 1 | 0 | 0 | | 0 | 1 | 1 | 0 | 1 | 1 | 0 | 1 | 1 | 1 | 0 | 0 | 0 |
| | 5.3808 | 2 | 2 | 2 | 2 | 2 | 2 | 2 | 3 | 3 | 0 | 2 | 2 | 3 | 2 | 2 | 2 | 3 | 2 | 2 | 3 | 3 |
| | 5.3808 | 2 | 3 | 3 | 2 | 3 | 3 | 3 | 3 | 3 | 0 | 3 | 2 | 3 | 2 | 2 | 2 | 3 | 2 | 1 | 2 | 2 |
| | 1.1210 | 2 | 2 | 2 | 3 | 2 | 2 | 2 | 2 | 2 | 0 | 0 | 2 | 3 | 2 | 2 | 2 | 3 | 3 | 1 | 3 | 0 |
| | 1.1210 | 2 | 2 | 2 | 3 | 2 | 2 | 2 | 2 | 2 | 0 | 0 | 2 | 2 | 2 | 2 | 2 | 3 | 3 | 1 | 2 | 2 |
| 44 | 0.2803 | 1 | 1 | 1 | 3 | 1 | 1 | 1 | 1 | 2 | 0 | 0 | 0 | 2 | 0 | 0 | 0 | 2 | 2 | 1 | 2 | 1 |
| | 0.2803 | 0 | 2 | 0 | 3 | 2 | 1 | 0 | 2 | 0 | 0 | 0 | 0 | 1 | 0 | 0 | 0 | 3 | 3 | 2 | 3 | 0 |
| | 0.0701 | 0 | 1 | 1 | 3 | 1 | 0 | 0 | | 1 | 0 | 0 | 0 | 0 | 0 | 0 | 0 | 2 | 2 | 2 | 2 | 2 |
| | 0.0701 | 0 | | | 2 | 1 | 2 | 2 | | 1 | 0 | 0 | 0 | 2 | 0 | 0 | 0 | 2 | 3 | 1 | 3 | 0 |
| 83 | 11.2100 | | | | 2 | 1 | 3 | 3 | | 3 | 0 | 0 | 2 | 2 | 2 | 1 | 3 | 3 | 3 | 1 | 3 | 2 |
| | 11.2100 | | | | 3 | 1 | 3 | 3 | | 3 | 0 | Z | 2 | 2 | 2 | 2 | 2 | 3 | 2 | 2 | 2 | 0 |
| | 5.6050 | | | | 2 | 0 | 3 | 2 | | 2 | 0 | Z | 0 | 0 | 0 | 0 | 0 | 2 | 3 | 1 | 3 | 2 |
| | 5.6050 | | | | 3 | 1 | 3 | 3 | | 1 | 1 | Z | 0 | 0 | 0 | 0 | 0 | 3 | 3 | 1 | 3 | 0 |
| | 2.8025 | | | | 3 | 1 | 3 | 2 | | 3 | 0 | Z | 0 | 2 | 0 | 0 | 0 | 3 | 2 | 2 | 2 | 1 |
| | 2.8025 | | | | 3 | 0 | 3 | 2 | | 2 | 0 | 0 | 0 | 2 | 0 | 0 | 0 | 2 | 3 | 1 | 2 | 2 |
| | 1.1210 | | | | 2 | 1 | 1 | N | | 1 | 0 | 0 | 0 | 2 | 0 | 0 | 0 | 2 | 2 | 1 | 2 | 0 |
| 83 | 1.1210 | | | | 2 | 1 | 3 | 1 | | 1 | 0 | 0 | 0 | 2 | 0 | 1 | 0 | 2 | 0 | 0 | 3 | 0 |
| | 0.5605 | 0 | | | 2 | 1 | 1 | N | | 1 | 0 | Z | 0 | 1 | 0 | 2 | 1 | 3 | 0 | 0 | 2 | 0 |
| | 0.5605 | 0 | | | 3 | 1 | 1 | 1 | | 0 | 0 | 0 | 0 | 0 | 0 | 0 | 0 | 2 | 0 | 0 | 2 | 0 |
| | 0.2803 | 0 | | | 2 | 0 | 1 | N | | 0 | 0 | Z | 0 | 0 | 0 | 0 | 0 | 3 | 0 | 0 | 3 | 0 |
| | 0.2803 | 0 | | | 2 | 0 | 1 | 1 | | 0 | 0 | 0 | 0 | 0 | 0 | 0 | 0 | 2 | 0 | 0 | 1 | 0 |

As can be seen from the data above, some of the compounds appear to be quite safe on certain crops and can thus be used for selective control of weeds in these crops.

The herbicidal compositions of this invention, including concentrates which require dilution prior to application, may contain at least one active ingredient and an adjuvant in liquid or solid form. The compositions are prepared by admixing the active ingredient with an adjuvant including diluents, extenders, carriers, and conditioning agents to provide compositions in the form of finely-divided particulate solids, granules, pellets, solutions, dispersions or emulsions. Thus, it is believed that the active ingredient could be used with an adjuvant such as a finely-divided solid, a liquid of organic origin, water, a wetting agent, a dispersing agent, an emulsifying agent or any suitable combination of these.

Suitable wetting agents are believed to include alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, polyoxyethylene derivatives of alkylphenols (particularly isooctylphenol and nonylphenol) and polyoxyethylene derivatives of the mono-higher fatty acid esters of hexitol anhydrides (e.g., sorbitan). Preferred dispersants are methyl, cellulose, polyvinyl alcohol, sodium lignin sulfonates, polymeric alkyl naphthalene sulfonates, sodium naphthalene sulfonate, and polymethylene bisnaphthalene sulfonate.

Wettable powders are water-dispersible compositions containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The wettable powders compositions of this invention usually contain from above 0.5 to 60 parts (preferably from 5–20 parts) of active ingredient, from about 0.25 to 25 parts (preferably 1–15 parts) of wetting agent, from about 0.25 to 25 parts (preferably 1.0–15 parts) of dispersant and from 5 to about 95 parts (preferably 5–50 parts) of inert solid extender, all parts being by weight of the total composition. Where required, from about 0.1 to 2.0 parts of the solid inert extender can be replaced by a corrosion inhibitor or anti-foaming agent or both.

Other formulations include dust concentrates comprising from 0.1 to 60% by weight of the active ingredient on a suitable extender; these dusts may be diluted for application at concentrations within the range of from about 0.1–10% by weight.

Aqueous suspensions or emulsions may be prepared by stirring a nonaqueous solution of a water-insoluble active ingredient and an emulsification agent with water until uniform and then homogenizing to give stable emulsion of very finely-divided particles. The resulting concentrated aqueous suspension is characterized by its extremely small particle size, so that when diluted and sprayed, coverage is very uniform. Suitable concentrations of these formulations contain from about 0.1–60% preferably 5–50% by weight of active ingredient, the upper limit being determined by the solubility limit of active ingredient in the solvent.

Concentrates are usually solutions of active ingredient in water-immiscible or partially water-immiscible solvents together with a surface active agent. Suitable solvents for the active ingredient of this invention include dimethylformamide, dimethylsulfoxide, N-methyl-pyrrolidone, hydrocarbons, and water-immiscible ethers, esters, or ketones. However, other high strength liquid concentrates may be formulated by dissolving the active ingredient in a solvent then diluting, e.g., with kerosene, to spray concentration.

The concentrate compositions herein generally contain from about 0.1 to 95 parts (preferably 5–60 parts) active ingredient, about 0.25 to 50 parts (preferably 1–25 parts) surface active agent and where required about 4 to 94 parts solvent, all parts being by weight based on the total weight of emulsifiable oil.

Granules are physically stable particulate compositions comprising active ingredient adhering to or distributed through a basic matrix of an inert, finely-divided particulate extender. In order to aid leaching of the active ingredient from the particulate, a surface active agent such as those listed hereinbefore can be present in the composition. Natural clays, pyrophyllites, illite, and vermiculite are examples of operable classes of particulate mineral extenders. The preferred extenders are the porous, absorptive, preformed particles such as preformed and screened particulate attapulgite or heat expanded, particulate vermiculite and the finely-divided clays such as kaolin clays, hydrated attapulgite or bentonitic clays. These extenders are sprayed or blended with the active ingredient to form the herbicidal granules.

The granular compositions of this invention may contain from about 0.1 to about 30 parts by weight of active ingredient per 100 parts by weight of clay and 0 to about 5 parts by weight of surface active agent per 100 parts by weight of particulate clay.

The compositions of this invention can also contain other additaments, for example, fertilizers, other herbicides, other pesticides, safeners and the like used as adjuvants or in combination with any of the above-described adjuvants. Chemicals useful in combination with the active ingredients of this invention included, for example, triazines, ureas, carbamates, acetamides, acetanilides, uracils, acetic acid or phenol derivatives, thiolcarbamates, triazoles, benzoic acids, nitriles, biphenyl ethers and the like such as:

Heterocyclic Nitrogen/Sulfur Derivatives

2-Chloro-4-ethylamino-6-isopropylamino-s-triazine
2-Chloro-4,6-bis(isopropylamino)-s-triazine
2-Chloro-4,6-bis(ethylamino)-s-triazine
3-Isopropyl-1H-2,1,3-benzothiadiazin-4-(3H)-one 2,2 dioxide
3-Amino-1,2,4-triazole
6,7-Dihydrodipyrido(1,2-α:2',1'-c)-pyrazidiinium salt
5-Bromo-3-isopropyl-6-methyluracil 1,1'-Dimethyl-4,4'-bipyridinium
2-(4-isopropyl-4-methyl-5-oxo-2-imidazolin-2-yl)-3-quinolinecarboxylic acid
Isopropylamine salt of 2-(4-isopropyl-4-methyl-5-oxo-2-imidazolin-2-yl)nicotinic acid
Methyl 6-(4-isopropyl-4-methyl-5-oxo-2-imidazolin-2-yl)-m-toluate and methyl 2-(4-isopropyl-4-methyl-5-oxo-2-imidazolin-2-yl)-p-toluate Ureas N-(4-chlorophenoxy) phenyl-N,N-dimethylurea
N,N-dimethyl-N'-(3-chloro-4-methylphenyl) urea
3-(3,4-dichlorophenyl)-1,1-dimethylurea 1,3-Dimethyl-3-(2-benzothiazolyl) urea
3-(p-Chlorophenyl)-1,1-dimethylurea
1-Butyl-3-(3,4-dichlorophenyl)-1-methylurea
2-Chloro-N[(4-methoxy-6-methyl-3,5-triazin-2-yl) aminocarbonyl]-benzenesulfonamide
Methyl 2-(((((4,6-dimethyl-2-pyrimidinyl)amino)carbonyl)amino)sulfonyl) benzoate
Ethyl 2-[methyl 2-(((((4,6-dimethyl-2-pyrimidinyl)amino)carbonyl)amino)sulfonyl)]benzoate
Methyl-2((4,6-dimethoxy pyrimidin-2-yl)aminocarbonyl)amino sulfonyl methyl) benzoate
Methyl 2-(((((4-methoxy-6-methyl-1,3,5-triazin-2-yl)amino)carbonyl)amino)sulfonyl) benzoate

Carbamates/Thiolcarbamates

2-Chloroallyl diethyldithiocarbamate
S-(4-chlorobenzyl)N,N-diethylthiolcarbamate
Isopropyl N-(3-chlorophenyl) carbamate
S-2,3-dichloroallyl N,N-diisopropylthiolcarbamate
S-N,N-dipropylthiolcarbamate
S-propyl N,N-dipropylthiolcarbamate
S-2,3,3-trichloroallyl N,N-diisopropylthiolcarbamate

Acetamides/Acetanilides/Anilines/Amides

2-Chloro-N,N-diallylacetamide
N,N-dimethyl-2,2-diphenylacetamide
N-(2,4-dimethyl-5-[[(trifluoromethyl)sulfonyl]amino]-phenyl]acetamide N-Isopropyl-2-chloroacetanilide
2',6'-Diethyl-N-methoxymethyl-2-chloroacetanilide
2'-Methyl-6'-ethyl-N-(2-methoxyprop-2-yl)-2-chloroacetanilide
α,α,α-Trifluoro-2,6-dinitro-N,N-dipropyl-p-toluidine
N-(1,1-dimethylpropynyl)-3,5-dichlorobenzamide

Acids/Esters/Alcohols 2,2-Dichloropropionic acid
2-Methyl-4-chlorophenoxyacetic acid
2,4-Dichlorophenoxyacetic acid
Methyl-2-[4-(2,4-dichlorophenoxy)phenoxy]propionate
3-Amino-2,5-dichlorobenzoic acid
2-Methoxy-3,6-dichlorobenzoic acid
2,3,6-Trichlorophenylacetic acid
N-1-naphthylphthalamic acid
Sodium 5-[2-chloro-4-(trifluoromethyl)phenoxy]-2-nitrobenzoate
4,6-Dinitro-o-sec-butylphenol N-(phosphonomethyl) glycine and its salts.
Butyl 2-[4-[(5-(trifluoromethyl)-2-pyridinyl)oxy]-phenoxy]-propanoate

Ethers 2,4-Dichlorophenyl-4-nitrophenyl ether
2-Chloro-α,α,α-trifluoro-p-tolyl-3-ethoxy-4-nitrodiphenyl ether
5-(2-chloro-4-trifluoromethylphenoxy)-N-methylsulfonyl 2-nitrobenzamide
1'-(Carboethoxy) ethyl 5-[2-chloro-4-(trifluoromethyl)-phenoxy]-2-nitrobenzoate

Miscellaneous 2,6-Dichlorobenzonitrile
Monosodium acid methanearsonate
Disodium methanearsonate
2-(2-chlorophenyl)methyl-4,4-dimethyl-3-isoxazolidinone
7-oxabicyclo (2.2.1) heptane, 1-methyl-4-(1-methyl ethyl)-2-(2-methylphenylmethoxy)-,exo- Fertilizers useful in combination with the active ingredients include, for example ammonium nitrate, urea, potash and superphosphate. Other useful additaments include materials in which plant organisms take root and grow such as compost, manure, humus, sand and the like.

Herbicidal formulations of the types described above are exemplified in several illustrative embodiments below.

|  | Weight Percent |
|---|---|
| I. Emulsifiable Concentrates | |
| A. Compound of Example No. 3 | 11.0 |
| Free acid of complex organic phosphate or aromatic or aliphatic hydrophobe base (e.g., GAFAC RE-610, registered trademark of GAF Corp.) | 5.59 |
| Polyoxyethylene/polyoxypropylene block copolymer with butanol (e.g., Tergitol XH, registered trademark of Union Carbide Corp.) | 1.11 |
| Phenol | 5.34 |
| Monochlorobenzene | 76.96 |
|  | 100.00 |
| B. Compound of Example No. 14 | 25.00 |
| Free acid of complex organic phosphate of aromatic or aliphatic hydrophobe base (e.g., GAFAC RE-610) | 5.00 |
| Polyoxyethylene/polyoxypropylene block copolymer with butanol (e.g., Tergitol XH) | 1.60 |
| Phenol | 4.75 |
| Monochlorobenzene | 63.65 |
|  | 100.00 |
| II. Flowables | |
| A. Compound of Example No. 24 | 25.00 |
| Methyl cellulose | 0.3 |
| Silica Aerogel | 1.5 |
| Sodium lignosulfonate | 3.5 |
| Sodium N-methyl-N-oleyl taurate | 2.0 |
| Water | 67.7 |
|  | 100.00 |
| B. Compound of Example No. 18 | 45.0 |
| Methyl cellulose | .3 |
| Silica aerogel | 1.5 |
| Sodium lignosulfonate | 3.5 |
| Sodium N-methyl-N-oleyl taurate | 2.0 |
| Water | 47.7 |
|  | 100.00 |
| III. Wettable Powders | |
| A. Compound of Example No. 5 | 25.0 |
| Sodium lignosulfonate | 3.0 |
| Sodium N-methyl-N-oleyl-taurate | 1.0 |
| Amorphous silica (synthetic) | 71.0 |
|  | 100.00 |
| B. Compound of Example 21 | 80.00 |
| Sodium dioctyl sulfosuccinate | 1.25 |
| Calcium lignosulfonate | 2.75 |
| Amorphous silica (synthetic) | 16.00 |
|  | 100.00 |
| C. Compound of Example No. 6 | 10.0 |
| Sodium lignosulfonate | 3.0 |
| Sodium N-methyl-N-oleyl-taurate | 1.0 |
| Kaolinite clay | 86.0 |
|  | 100.00 |
| IV. Dusts | |
| A. Compound of Example No. 13 | 2.0 |
| Attapulgite | 98.0 |
|  | 100.00 |
| B. Compound of Example No. 10 | 60.0 |
| Montmorillonite | 40.0 |
|  | 100.00 |
| C. Compound of Example No. 54 | 30.0 |
| Ethylene glycol | 1.0 |
| Bentonite | 69.0 |

|   | Weight Percent |
|---|---|
| D. Compound of Example No. 62 | 1.0 |
| Diatomaceous earth | 99.0 |
|   | 100.00 |
| V. Granules |   |
| A. Compound of Example No. 52 | 15.0 |
| Granular attapulgite (20/40 mesh) | 85.0 |
|   | 100.00 |
| B. Compound of Example No. 70 | 30.0 |
| Diatomaceous earth (20/40) | 70.0 |
|   | 100.00 |
| C. Compound of Example No. 58 | 1.0 |
| Ethylene glycol | 5.0 |
| Methylene blue | 0.1 |
| Pyrophyllite | 93.9 |
|   | 100.00 |
| D. Compound of Example No. 46 | 5.0 |
| Pyrophyllite (20/40) | 95.0 |
|   | 100.00 |

When operating in accordance with the present invention, effective amounts of the compounds of this invention are applied to the soil containing the seeds, or vegetative propagules or may be incorporated into the soil media in any convenient fashion. The application of liquid and particulate solid compositions to the soil can be carried out by conventional methods, e.g., power dusters, boom and hand sprayers and spray dusters. The compositions can also be applied from airplanes as a dust or a spray because of their effectiveness at low dosages.

The exact amount of active ingredient to be employed is dependent upon various factors, including the plant species and stage of development thereof, the type and condition of soil, the amount of rainfall and the specific compounds employed. In selective preemergence application or to the soil, a dosage of from about 0.02 to about 11.2 kg/ha, preferably from about 0.1 to about 5.60 kg/ha, is usually employed. Lower or higher rates may be required in some instances. One skilled in the art can readily determine from this specification, including the above examples, the optimum rate to be applied in any particular case.

The term "soil" is employed in its broadest sense to be inclusive of all conventional "soils" as defined in *Webster's New International Dictionary*, Second Edition, Unabridged (1961). Thus, the term refers to any substance or media in which vegetation may take root and grow, and includes not only earth but also compost, manure, muck, humus, sand, and the like, adapted to support plant growth.

Although the invention is described with respect to specific modifications, the details thereof are not to be construed as limitations.

We claim:

1. A compound represented by the formula

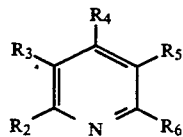

wherein:

$R_3$ is selected from the group consisting of 5,6-dihydro-4H-1,3-oxazin-2yl and 5,6-dihydro-4H-1,3-thiazin-2-yl; each optionally substituted with one or more substituents selected from lower alkyl, alkoxy and trifluoroacetyl;

$R_4$ is selected from $C_1$–$C_4$ straight or branched chain alkyl, $C_3$–$C_4$ cycloalkyl, cycloalkylalkyl, alkylthioalkyl, and bis(alkylthio)alkyl;

$R_5$ or is

or —C≡N where $Z_1$ is O, S, or $NR_7$ where $R_7$ is lower alkyl, and $Z_2$ is selected from alkoxy, alkenoxy, alkynoxy, alkylthio, pyrazolyl, haloalkoxy, cyanoalkoxy, chloro, and —$NHR_8$ where $R_8$ is lower alkyl;

$R_2$ and $R_6$ are independently selected from fluorinated methyl, chlorofluorinated methyl, chlorinated methyl, and lower alkyl, provided that one of $R_2$ and $R_6$ must be fluorinated or chlorofluorinated methyl.

2. A compound according to claim 1 wherein one of $R_2$ and $R_6$ is $CF_3$ and the other is $CF_2H$.

3. A compound according to claim 2 wherein $R_4$ is selected from $C_3$–$C_4$ branched chain alkyl.

4. A compound according to claim 2 wherein $R_4$ is selected from cyclobutyl and cyclopropylmethyl.

5. A compound according to claim 3 wherein $R_5$ is methoxycarbonyl.

6. A compound according to claim 3 wherein $R_5$ is methylthiocarbonyl.

7. A compound according to claim 1 wherein one of $R_2$ and $R_6$ is $CF_3$ and the other is $CF_2Cl$.

8. A compound according to claim 7 wherein $R_4$ is selected from $C_3$–$C_4$ branched chain alkyl.

9. A compound according to claim 7 wherein $R_4$ is selected from cyclobutyl and cyclopropylmethyl.

10. A compound according to claim 8 wherein $R_5$ is methoxycarbonyl.

11. A compound according to claim 8 wherein $R_5$ is methylthiocarbonyl.

12. A method of controlling undesirable vegetation comprising applying thereto a compound represented by the formula

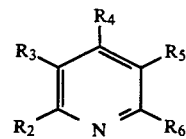

wherein:

$R_3$ is selected from the group consisting of 5,6-dihydro-4H-1,3-oxazin-2yl and 5,6-dihydro-4H-1,3-thiazin-2-yl; each optionally substituted with one or more substituents selected from lower alkyl, alkoxy and trifluoroacetyl;

$R_4$ is selected from $C_1$–$C_4$ straight or branched chain alkyl, $C_3$–$C_4$ cycloalkyl, cycloalkylalkyl, alkylthioalkyl, and bis(alkylthioalkyl);

$R_5$ or is

or —C≡N where $Z_1$ is O, S, or $NR_7$ where $R_7$ is lower alkyl, and $Z_2$ is selected from alkoxy, alkenoxy, alkynoxy, alkylthio, pyrazolyl, haloalkoxy, cycanoalkoxy, chloro, and —$NHR_8$ where $R_8$ is lower alkyl;

$R_2$ and $R_6$ are independently selected from fluorinated methyl, chlorofluorinated methyl, chlorinated methyl, and lower alkyl, provided that one of $R_2$ and $R_6$ must be fluorinated or chlorofluorinated methyl.

13. A method according to claim 12 wherein one of $R_2$ and $R_6$ is $CF_3$ and the other is $CF_2H$.

14. A method according to claim 13 wherein $R_4$ is selected from $C_3$-$C_4$ branched chain alkyl.

15. A method according to claim 13 wherein $R_4$ is selected from cyclobutyl and cyclopropylmethyl.

16. A method according to claim 14 wherein $R_5$ is methoxycarbonyl.

17. A method according to claim 14 wherein $R_5$ is methylthiocarbonyl.

18. A method according to claim 12 wherein one of $R_2$ and $R_6$ is $CF_3$ and the other is $CF_2Cl$.

19. A method according to claim 18 wherein $R_4$ is selected from $C_3$-$C_4$ branched chain alkyl.

20. A method according to claim 18 wherein $R_4$ is selected frm cyclobutyl and cyclopropylmethyl.

21. A method according to claim 19 wherein $R_5$ is methoxycarbonyl.

22. A method according to claim 19 wherein $R_5$ is methylthiocarbonyl.

23. A herbicidal composition comprising an adjuvant and a compound represented by the formula

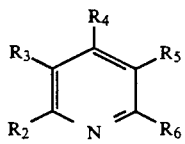

wherein:
$R_3$ is selected from the group consisting of 5,6-dihydro-4H-1,3-oxazin-2-yl and 5,6-dihydro-4H-1,3-thiazin-2-yl; each optionally substituted with one or more substituents selected from lower alkyl, alkoxy and trifluoroacetyl;

$R_4$ is selected from $C_1$-$C_4$ straight or branched chain alkyl, $C_3$-$C_4$ cycloalkyl, cycloalkylalkyl, alkylthioalkyl, and bis(alkylthio)alkyl;

$R_5$ is

or —C≡N where $Z_1$ is O, S, or $NR_7$ where $R_7$ is lower alkyl, and $Z_2$ is selected from alkoxy, alkenoxy, alkynoxy, alkylthio, pyrazolyl, haloalkoxy, cyanoalkoxy, chloro, and —$NHR_8$ where $R_8$ is lower alkyl;

$R_2$ and $R_6$ are independently selected from fluorinated methyl, chlorofluorinated methyl, chlorinated methyl, and lower alkyl, provided that one of $R_2$ and $R_6$ must be fluorinated or chlorofluorinated methyl.

24. A composition according to claim 23 wherein one of $R_2$ and $R_6$ is $CF_3$ and the other is $CF_2H$.

25. A composition according to claim 24 wherein $R_4$ is selected from $C_3$-$C_4$ branched chain alkyl.

26. A composition according to claim 24 wherein $R_4$ is selected from cyclobutyl and cyclopropylmethyl.

27. A composition according to claim 25 wherein $R_5$ is methoxycarbonyl.

28. A composition according to claim 26 wherein $R_5$ is methylthiocarbonyl.

29. A composition according to claim 23 wherein one of $R_2$ and $R_6$ is $CF_3$ and the other is $CF_2Cl$.

30. A composition according to claim 29 wherein $R_4$ is selected from $C_3$-$C_4$ branched chain alkyl.

31. A composition according to claim 29 wherein $R_4$ is selected from cyclobutyl and cyclopropylmethyl.

32. A composition according to claim 30 wherein $R_5$ is methoxycarbonyl.

33. A composition according to claim 30 wherein $R_5$ is methylthiocarbonyl.

34. The compound of claim 6 wherein $R_2$ is difluoromethyl, $R_3$ is 5,6-dihydro-4H-1,3-oxazin-2-yl, $R_4$ is 2-methylpropyl, and $R_6$ is trifluoromethyl.

* * * * *